(12) United States Patent
Shanmugam et al.

(10) Patent No.: US 11,441,187 B2
(45) Date of Patent: Sep. 13, 2022

(54) METHODS OF CHARACTERIZING AND TREATING HIDRADENITIS SUPPURATIVA

(71) Applicant: The George Washington University, Washington, DC (US)

(72) Inventors: Victoria Shanmugam, Great Falls, VA (US); Derek Jones, Washington, DC (US)

(73) Assignee: The George Washington University, Washington, DC (US)

( * ) Notice: Subject to any disclaimer, the term of this patent is extended or adjusted under 35 U.S.C. 154(b) by 149 days.

(21) Appl. No.: 16/593,844

(22) Filed: Oct. 4, 2019

(65) Prior Publication Data

US 2020/0109453 A1 Apr. 9, 2020

Related U.S. Application Data

(60) Provisional application No. 62/741,441, filed on Oct. 4, 2018.

(51) Int. Cl.
| | |
|---|---|
| *C12Q 1/68* | (2018.01) |
| *C12Q 1/6883* | (2018.01) |
| *C12Q 1/6823* | (2018.01) |
| *G16H 50/30* | (2018.01) |
| *C12Q 1/6825* | (2018.01) |
| *A61K 45/06* | (2006.01) |

(52) U.S. Cl.
CPC ......... *C12Q 1/6883* (2013.01); *C12Q 1/6823* (2013.01); *C12Q 1/6825* (2013.01); *G16H 50/30* (2018.01); *A61K 45/06* (2013.01)

(58) Field of Classification Search
None
See application file for complete search history.

(56) References Cited

PUBLICATIONS

Blok et al. Gene expression profiling of skin and blood in hidradenitis suppurativa. British Journal of Dermatology; 2016; 174: pp. 1392-1394. (Year: 2016).*
Blok et al. Gene expression profiling of skin and blood in hidradenitis suppurativa. British Journal of Dermatology; 2016; 174: pp. 1392-1394. Supplemental Table S1. (Year: 2016).*
Dickinson-Blok. Hidradenitis suppurativa: From pathogenesis to emerging treatment options (Thesis); University of Groningen, The Netherland; Sep. 2015; p. 1-152. ISBN: 978-90-367-8142-8, ISBN: 978-90-367-8141-1 (e-version). (Year: 2015).*
Kimball, et al. Assessing the validity, responsiveness and meaningfulness of the Hidradenitis Suppurativa Clinical Response (HiSCR) as the clinical endpoint for hidradenitis suppurativa treatment. British Journal of Dermatology; 2014; 171: 1434-1442. (Year: 2014).*
Dickinson-Blok, Hidradenitis suppurativa: From pathogenesis to emerging treatment options; University of Groningen, The Netherland; 2015; p. 1-152. ISBN: 978-90-367-8142-8, ISBN: 978-90-367-8141-1 (e-version). (Year: 2015).*
Blok et al. British Journal of Dermatology; 2016; 174: pp. 1392-1394. (Year: 2016).*
Kimball, et al. British Journal of Dermatology; 2014; 171: 1434-1442. (Year: 2014).*
Banerjee et al., "Interferon-gamma (IFN-gamma) is Elevated in Wound Exudate from Hidradenitis Suppurativa", Immunological Investigations. 2017, vol. 46, No. 2, 149-158.
Jones et al., "Inherent differences in keratinocyte function in hidradenitis suppurativa: Evidence for the role of IL-22 in disease pathogenesis," Immunological Investigations, 2018, vol. 47, No. 1, 57-70.
Shanmugam et al., "Longitudinal observational study of hidradenitis suppurativa: impact of surgical intervention with adjunctive biologic therapy," International Journal of Dermatology, 2018, 57, 62-69.
Boortalary et al., "Prevalence of positive QuantiFERON gold in-tube testing in hidradenitis suppurativa," Journal of Dermatological Treatment, 2018, vol. 29, No. 6, 637-640.
Mulani et al., "Prevalence of antinuclear antibodies in hidradenitis suppurativa," International Journal of Rheumatic Diseases, 2018, 21:1018-1022.
Choi et al., "Co-occurrence of anaerobes in human chronic wounds," Microbial Ecology, 2019, 77:808-820.
Shanmugam et al., "Transcriptome patterns in hidradenitis suppurativa: support for the role of antimicrobial peptides and interferon pathways in disease pathogenesis," Clinical and Experimental Dermatology, Mar. 2019, pp. 1-11.
Edfors et al., "Gene-specific correlation of RNA and protein levels in human cells and tissues," Molecular Systems Biology, 2016, 12:883, pp. 1-10.
Harris et al., "Research electronic data capture (REDCap)—A metadata-driven methodology and workflow process for providing translational research informatics support," Journal of Biomedical Informatics, 2009, 42, 377-381.
Fan et al., "BeadArray™-based solutions for enabling the promise of pharmacogenomics," BioTechniques Oct. 2005, 39: 583-588.
Ritchie et al., "limma powers differential expression analyses for RNA-sequencing and microarray studies," Nucleic Acids Research, 2015, vol. 43, No. 7, pp. 2-13.
Dunning et al., "beadarray: R classes and methods for Illumina bead-based data," Bioinformatics, 2007, vol. 23, No. 16, pp. 2183-2184.
Phipson et al., "Robust Hyperparameter Estimation Protects Against Hypervariable Genes and Improves Power to Detect Differential Expression," Ann Appl Stat., Jun. 2016, 10(2): 946-63.
Johnson et al., "Adjusting batch effects in microarray expression data using empirical Bayes methods," Biostatistics, 2007, 8, 1, pp. 118-127.
Krämer et al., "Causal analysis approaches in Ingenuity Pathway Analysis," Bioinformatics, 2014, vol. 30, No. 4, pp. 523-530.

* cited by examiner

*Primary Examiner* — Jeanine A Goldberg
*Assistant Examiner* — Wahwah T Johnson
(74) *Attorney, Agent, or Firm* — Kory D. Christensen

(57) ABSTRACT

Disclosures herein encompass methods of treating a subject with moderate to severe hidradenitis suppurativa (HS) encompassing the determination of differential gene expression to characterize HS severity followed by administration of a treatment specific for the stage of HS severity characterized in the subject.

18 Claims, 2 Drawing Sheets

METHODS OF CHARACTERIZING AND TREATING HIDRADENITIS SUPPURATIVA

CROSS REFERENCE TO RELATED APPLICATION

This application claims the benefit of U.S. Provisional Application No. 62/741,441, filed on Oct. 4, 2018, the disclosure of which is hereby incorporated by reference in its entirety.

GOVERNMENTAL RIGHTS

This invention was made with government support under R01NR013888 and UL1TR000075 awarded by the National Institutes of Health. The government has certain rights in the invention.

FIELD

The disclosures herein encompass methods of treating a subject with moderate to severe hidradenitis suppurativa (HS) encompassing the determination of differential gene expression to characterize HS severity followed by administration of a treatment specific for the stage of HS severity characterized in the subject.

BACKGROUND

Hidradenitis suppurativa (HS) is a recurrent, chronic inflammatory disease of the apocrine sweat glands and presenting with painful nodules, abscesses, sinus tracts, and scarring. The primary defect in HS pathophysiology involves follicular occlusion of the folliculopilosebaceous unit, followed by follicular rupture, and immune responses (perifollicular lympho-histiocytic inflammation), finally leading to the development of clinical HS lesions. In addition to being a painful disease, HS has a destructive impact on the subject's quality of life.

Early diagnosis is very important for HS subjects in order to ensure the best possible course of treatment; however, the disease is frequently misdiagnosed, underdiagnosed, and there is often a diagnostic delay, which averages about seven years. Early diagnosis and treatment can prevent HS from worsening, reducing the significant physical and emotional toll of the diseases.

There is no known cure for HS. Treatment depends on what clinical stage a subject is at and the severity of their condition. Mild HS can usually be managed with home remedies whereas moderate and severe cases of HS may require one or more medications. Once HS disease severity is diagnosed, a subject can be administered the appropriate treatment for that particular clinical stage and, as such, prevent disease progression.

SUMMARY

In an aspect, the disclosure provides methods of treating a subject with moderate to severe hidradenitis suppurativa (HS), the methods encompassing: a) determining an gene expression level of S100A7, S100A8, S100A9, STAT1, NFATC3, BTK, CXCR4, CD86, CD247, CD3D, HLA-DMA, HLS-DMB, IL6, IL4R, CD79A, CCL27, dermcidin, IL-37 or a combination thereof in a biological sample of a human subject; b) characterizing HS severity by comparing the subject's gene expression levels of S100A7, S100A8, S100A9, STAT1, NFATC3, BTK, CXCR4, CD86, CD247, CD3D, HLA-DMA, HLS-DMB, IL6, IL4R, CD79A, CCL27, dermcidin, IL-37 or combination thereof to a sample that does not have HS, wherein HS severity is characterized as moderate to severe when the expression level of S100A7, S100A8, S100A9, STAT1, NFATC3, BTK, CXCR4, CD86, CD247, CD3D, HLA-DMA, HLS-DMB, IL6, IL4R, or CD79A is increased in the subject compared to the sample that does not have HS, and the expression level of dermcidin or IL-37 is decreased in the subject compared to the sample that does not have HS; and c) administering an antibiotic, a retinoid, a steroid hormone, an anti-inflammatory, or a combination thereof to a subject characterized as having moderate to severe HS. In some aspects, HS severity is characterized as moderate to severe by methods disclosed herein when the expression level of at least two genes selected from a group encompassing S100A7, S100A8, S100A9, STAT1, NFATC3, BTK, CXCR4, CD86, CD247, CD3D, HLA-DMA, HLS-DMB, IL6, IL4R, or CD79A is increased in the subject compared to the sample that does not have HS, and the expression level of dermcidin and IL-37 is decreased in the subject compared to the sample that does not have HS. In other aspects, HS severity is characterized as moderate to severe by methods disclosed herein when the expression level of S100A8 and S100A9 is increased in the subject compared to the sample that does not have HS.

In some aspects, methods disclosed herein treat a subject characterized with moderate to severe HS encompasses administering an anti-inflammatory. In some aspects, the an anti-inflammatory administered is a tumor necrosis factor inhibitor, an interleukin-1 inhibitor, a Janus kinase (JAK) inhibitor, an interleukin-17 inhibitor, an interleukin-23 inhibitor, a Complement component 5a (C5a) inhibitor, or a combination thereof.

In some aspects, methods disclosed herein ameliorate at least one symptom of moderate to severe HS after administering an antibiotic, a retinoid, a steroid hormone, an anti-inflammatory, or a combination thereof to a subject characterized with moderate to severe HS. In other aspects, methods disclosed herein decrease the Dermatology Quality of Life Index (DQLI) score after administering an antibiotic, a retinoid, a steroid hormone, an anti-inflammatory, or a combination thereof to a subject characterized with moderate to severe HS. In other aspects, methods disclosed herein decrease the abscess and inflammatory nodule count (AN count) after administering an antibiotic, a retinoid, a steroid hormone, an anti-inflammatory, or a combination thereof to a subject characterized with moderate to severe HS. In other aspects, methods disclosed herein inhibit progression of the severity of HS after administering an antibiotic, a retinoid, a steroid hormone, an anti-inflammatory, or a combination thereof to a subject characterized with moderate to severe HS.

In some aspects, methods disclosed herein treat a subject by characterizing HS severity using methods that encompass a) obtaining a biological sample of a human subject; b) determining the gene expression level of S100A7, S100A8, S100A9, STAT1, NFATC3, BTK, CXCR4, CD86, CD247, CD3D, HLA-DMA, HLS-DMB, IL6, IL4R, CD79A, CCL27, dermcidin, IL-37 or a combination thereof in the biological sample by contacting the biological sample with a bead, wherein the bead comprises at least one oligonucleotide sequence complementary to S100A7, S100A8, S100A9, STAT1, NFATC3, BTK, CXCR4, CD86, CD247, CD3D, HLA-DMA, HLS-DMB, IL6, IL4R, CD79A, CCL27, dermcidin,or IL-37; c) detecting binding between S100A7, S100A8, S100A9, STAT1, NFATC3, BTK, CXCR4, CD86, CD247, CD3D, HLA-DMA, HLS-DMB, IL6, IL4R, CD79A, CCL27, dermcidin,or IL-37 in the biological sample to the bead comprising least one oligonucleotide sequence complementary to S100A7, S100A8, S100A9, STAT1, NFATC3, BTK, CXCR4, CD86, CD247, CD3D, HLA-DMA, HLS-DMB, IL6, IL4R, CD79A, CCL27, dermcidin,or IL-37, wherein detection of a bound oligonucleotide is measured using a fluorescent label; and d) characterizing HS severity as moderate to severe when the expression level of S100A7, S100A8, S100A9, STAT1, NFATC3, BTK, CXCR4, CD86, CD247, CD3D, HLA-DMA, HLS-DMB, IL6, IL4R, or CD79A is increased in the subject compared to the sample that does not have HS.

In another aspect, the disclosure provides methods of treating a subject with moderate to severe hidradenitis suppurativa (HS), the methods encompassing: a) determining an gene expression level of S100A7, S100A8, S100A9, STAT1, NFATC3, BTK, CXCR4, CD86, CD247, CD3D, HLA-DMA, HLS-DMB, IL6, IL4R, CD79A, CCL27, dermcidin, IL-37 or a combination thereof in a biological sample of a human subject; b) characterizing HS severity by comparing the subject's gene expression levels of S100A7, S100A8, S100A9, STAT1, NFATC3, BTK, CXCR4, CD86, CD247, CD3D, HLA-DMA, HLS-DMB, IL6, IL4R, CD79A, CCL27, dermcidin, IL-37 or combination thereof to a sample that does not have HS, wherein HS severity is characterized as moderate to severe when the expression level of S100A8 is increase at least 2-fold and the expression level of S100A9 is increased at least 2-fold in the subject compared to the sample that does not have HS, and the expression level of dermcidin is decreased at least 3-fold and the expression level of IL-37 is decreased at least 2-fold in the subject compared to the sample that does not have HS; and c) administering an antibiotic, a retinoid, a steroid hormone, an anti-inflammatory, or a combination thereof to a subject characterized as having moderate to severe HS.

In some aspects, methods disclosed herein treat a subject characterized with moderate to severe HS encompasses administering an anti-inflammatory. In some aspects, the an anti-inflammatory administered is a tumor necrosis factor inhibitor, an interleukin-1 inhibitor, a Janus kinase (JAK) inhibitor, an interleukin-17 inhibitor, an interleukin-23 inhibitor, a Complement component 5a (C5a) inhibitor, or a combination thereof.

In some aspects, methods disclosed herein ameliorate at least one symptom of moderate to severe HS after administering an antibiotic, a retinoid, a steroid hormone, an anti-inflammatory, or a combination thereof to a subject characterized with moderate to severe HS. In other aspects, methods disclosed herein decrease the Dermatology Quality of Life Index (DQLI) score after administering an antibiotic, a retinoid, a steroid hormone, an anti-inflammatory, or a combination thereof to a subject characterized with moderate to severe HS. In other aspects, methods disclosed herein decrease the abscess and inflammatory nodule count (AN count) after administering an antibiotic, a retinoid, a steroid hormone, an anti-inflammatory, or a combination thereof to a subject characterized with moderate to severe HS. In other aspects, methods disclosed herein inhibit progression of the severity of HS after administering an antibiotic, a retinoid, a steroid hormone, an anti-inflammatory, or a combination thereof to a subject characterized with moderate to severe HS.

In some aspects, methods disclosed herein treat a subject by characterizing HS severity using methods that encompass a) obtaining a biological sample of a human subject; b) determining the gene expression level of S100A7, S100A8, S100A9, STAT1, NFATC3, BTK, CXCR4, CD86, CD247, CD3D, HLA-DMA, HLS-DMB, IL6, IL4R, CD79A, CCL27, dermcidin, IL-37 or a combination thereof in the biological sample by contacting the biological sample with a bead, wherein the bead comprises at least one oligonucleotide sequence complementary to S100A7, S100A8, S100A9, STAT1, NFATC3, BTK, CXCR4, CD86, CD247, CD3D, HLA-DMA, HLS-DMB, IL6, IL4R, CD79A, CCL27, dermcidin,or IL-37; c) detecting binding between S100A7, S100A8, S100A9, STAT1, NFATC3, BTK, CXCR4, CD86, CD247, CD3D, HLA-DMA, HLS-DMB, IL6, IL4R, CD79A, CCL27, dermcidin,or IL-37 in the biological sample to the bead comprising least one oligonucleotide sequence complementary to S100A7, S100A8, S100A9, STAT1, NFATC3, BTK, CXCR4, CD86, CD247, CD3D, HLA-DMA, HLS-DMB, IL6, IL4R, CD79A, CCL27, dermcidin,or IL-37, wherein detection of a bound oligonucleotide is measured using a fluorescent label; and d) characterizing HS severity as moderate to severe when the expression level of S100A7, S100A8, S100A9, STAT1, NFATC3, BTK, CXCR4, CD86, CD247, CD3D, HLA-DMA, HLS-DMB, IL6, IL4R, or CD79A is increased in the subject compared to the sample that does not have HS.

DETAILED DESCRIPTION

Figure 1:
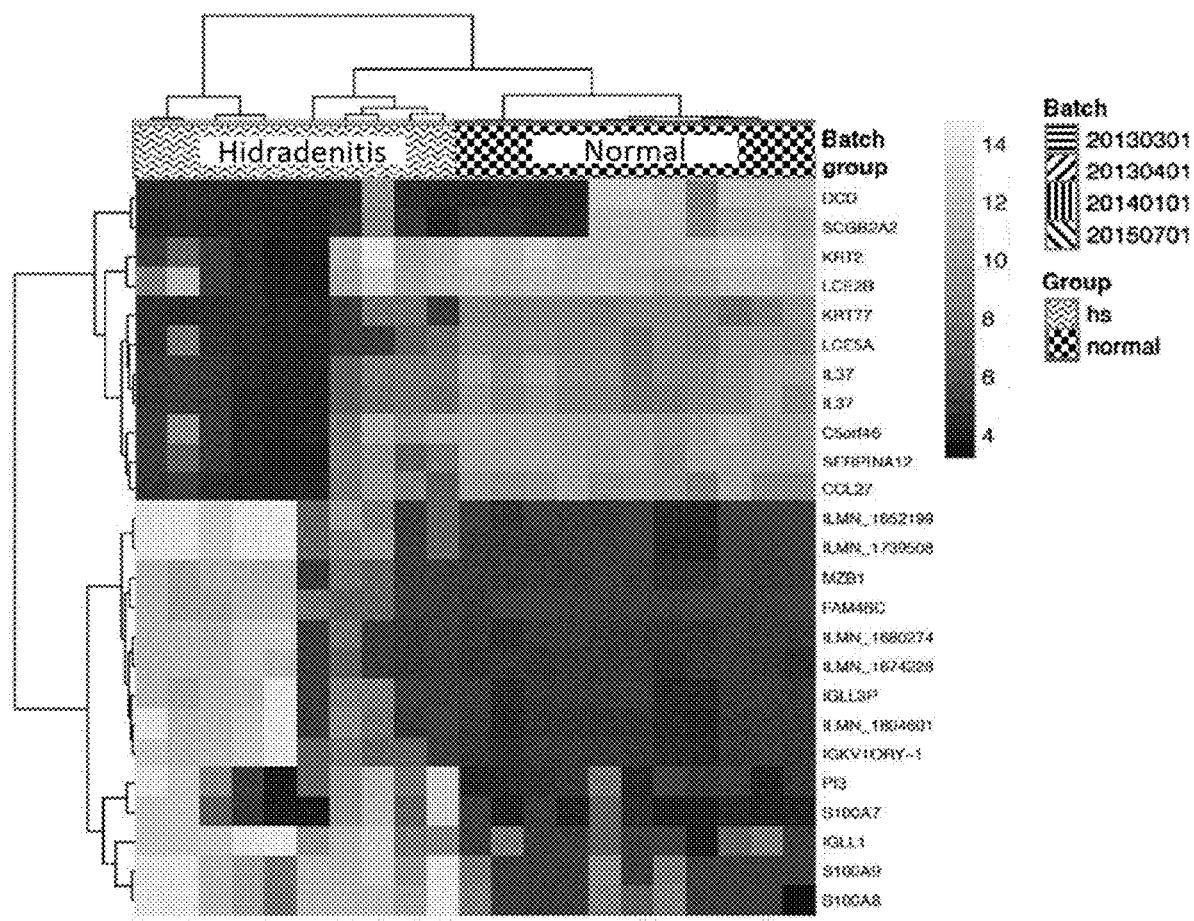
FIG. 1 depicts an image of a heat map reflecting the differential gene expression in hidradenitis suppurativa (HS) and healthy (normal) samples as measured by microarray analysis. Normalized expression values for 25 significant differentially expressed genes with the greatest absolute fold change are plotted in a low-to-high scale (blue-yellow-red). Unsupervised hierarchical clustering of genes (rows) and samples (columns) are also shown.

The present disclosure is based in part on the surprising discovery by the inventors that differentiation of gene expression (and subsequent protein expression) profiles can be used in hidradenitis suppurativa (HS) treatment regimens by accurately detecting HS as early as possible, thereby preventing disease progression, and informing the physician of potential clinical-stage dependent treatment that can be administered to the HS subject. As used herein, it is understood that "hidradenitis suppurativa" is synonymous with "acne inversa" or "AI" and these terms can be used interchangeably throughout the disclosure.

Aspects of the disclosure include methods of treating a subject having or suspected of having HS by assessing the subject's gene and/or protein expression profile, diagnosing the subject with HS and/or detecting the level of HS severity, and administering the appropriate treatment for the level of HS severity. In some embodiments, treatment after gene and/or protein expression profiling as disclosed herein may be administration of one or more home remedies, one or more pharmaceutical compositions, one or more radiological therapies, one or more surgical procedures, or a combination thereof. As used herein, the term "home remedies"

refers to an action and/or administration of a product that does not require a physician's prescription. In some other embodiments, treatment after gene and/or protein expression profiling as disclosed herein may prevent HS progression. In other embodiments, treatment after gene and/or protein expression profiling as disclosed herein may ameliorate one or more symptoms of a dermatological pathology associated with HS in a subject. In still other embodiments, treatment after gene and/or protein expression profiling as disclosed herein may reduce risk of recurrence in a subject diagnosed with HS following a surgical procedure.

I. Gene and Protein Expression Profiles

In general, methods disclosed herein include obtaining a gene expression profile and/or a protein expression profile from a subject having or suspected of having HS from at least one sample collected from said subject. As used herein, the term "gene expression profile" refers to a pattern of genes expressed in a sample at the transcription level. It is well known in the field that differential gene expression correlates to differential protein expression. (Edfors F et al., *Mol Syst Biol*. 2016; 12(10):883, the disclosures of which are incorporated herein). As such, methods disclosed herein also include obtaining a protein expression profile from a subject having or suspected of having HS from at least one sample collected from said subject.

As used herein, a suitable subject includes a mammal, a human, a livestock animal, a companion animal, a lab animal, or a zoological animal. In some embodiments, a subject may be a rodent, e.g., a mouse, a rat, a guinea pig, etc. In other embodiments, a subject may be a livestock animal. Non-limiting examples of suitable livestock animals may include pigs, cows, horses, goats, sheep, llamas and alpacas. In yet other embodiments, a subject may be a companion animal. Non-limiting examples of companion animals may include pets such as dogs, cats, rabbits, and birds. In yet other embodiments, a subject may be a zoological animal. As used herein, a "zoological animal" refers to an animal that may be found in a zoo. Such animals may include non-human primates, large cats, wolves, and bears. In other embodiments, the animal is a laboratory animal. Non-limiting examples of a laboratory animal may include rodents, canines, felines, and non-human primates. In some embodiments, the animal is a rodent. Non-limiting examples of rodents may include mice, rats, guinea pigs, etc. In preferred embodiments, the subject is a human.

In some embodiments, a gene expression profile and/or a protein expression profile can be obtained using at least one sample from a subject. In some aspects, at least one sample can be obtained from a subject who has not been diagnosed with hidradenitis suppurativa (HS). In other aspects, at least one sample can be obtained from a subject who has been diagnosed with HS. In still other aspects, at least one sample can be obtained from a subject who presents with at least one symptom of HS. Non-limiting symptoms of HS include presence of small pitted areas of skin containing blackheads, solitary or multiple isolated abscess formation without scarring or sinus tracts, painful, red, bumps or lesions that enlarge, break open, and drain pus that may have an unpleasant odor, leaking bumps or sores that heal very slowly, recur over time, and lead to scarring and sinus tracts, diffuse or broad involvement across a regional area with multiple interconnected sinus tracts and abscesses. As used herein, the term "sinus tracts" refers to a narrow opening or passageway underneath the skin that can extend in any direction through soft tissue and can result in dead space with potential for abscess formation. A sinus tract may also be referred to as a "tunneling wound." In yet other aspects, at least one sample can be obtained from a subject who presents with at least one symptom of HS in at least one intertriginous area. Non-limiting examples of intertriginous areas include the axillae, groin, and perineal areas of the subject's body. In other aspects, at least one sample can be obtained from a subject who has HS and the disease has been classified into one of the three stages of Hurley Staging. As used herein, "Hurley Staging" refers to a classification system used by medical professionals to assign a severity level to HS. A description of Hurley Staging is provided in Table 1. In some aspects, at least one sample can be obtained from a subject who has mild, moderate, or severe HS.

TABLE 1

| Hurley Stage Description | | |
|---|---|---|
| | Severity of HS | Description of Symptoms |
| Stage I | Mild | Solitary or multiple isolated abscess formation without scarring or sinus tracts. |
| Stage II | Moderate | Recurrent abscesses, single or multiple widely separated lesions with sinus tract formation. |
| Stage III | Severe | Diffuse or broad involvement across a regional area with multiple interconnected sinus tracts and abscesses. |

In other aspects, at least one sample can be obtained from a subject who has HS and disease activity has been assigned a modified Hidradenitis Sartorius Score (HSS). Modified Hidradenitis Sartorius Score (HSS) is a measure of HS activity and can be used to assess disease activity at baseline and thereafter. To assign a subject a HSS score, a score of 3 points is assigned for each anatomic region involved; 1 point per region is given for presence of nodules and 6 points for fistulae; the longest distance between lesions or size of the lesion is scored categorically (<5 cm (1 point), 5-10 cm (3 points) and >10 cm (9 points)); and whether lesions are separated by normal skin (0 points) or not (9 points). Regional scores are summed to achieve a total modified HSS. The upper limit of the scale is open. HS activity can be considered high if a subject has a HSS score greater than 60. HS activity can be considered moderate if a subject has a HSS score between 20 and 60. HS activity can be considered low if a subject has a HSS score less than 20. In some aspects, at least one sample can be obtained from a subject diagnosed with HS with a HSS score of at least 1, at least 10, at least 20, at least 40, at least 60, at least 80, or at least 100. In some aspects, at least one sample can be obtained from a subject diagnosed with HS with low disease activity, moderate disease activity, or high disease activity.

In other aspects, at least one sample can be obtained from a subject who has and a baseline abscess and inflammatory nodule count (AN count). As used herein, a baseline AN count is 3 or more abscesses and/or inflammatory nodules and a draining fistula count of 20 or fewer. In some aspects, an AN count can be associated with patient-reported quality of life and pain level.

In some other aspects, at least one sample can be obtained from a subject who presents with at least one symptom of HS and has been diagnosed with at least one comorbidity. Non-limiting examples of comorbidities include metabolic syndrome, cardiovascular disease (CVD), thyroid disease, arthropathy, an inflammatory skin condition, squamous cell carcinoma, polycystic ovary syndrome (PCOS), pyoderma gangrenosum, and inflammatory bowel disease. As used herein, metabolic syndrome can encompass elevated cholesterol and blood lipids, diabetes, obesity, or a combination thereof. As used herein, CVD can encompass hypertension, coronary artery disease, heart attack, heart failure, heart valve disease, congenital heart disease, cardiomyopathy, pericardial disease, aorta disease, vascular disease, or a combination thereof. As used herein, thyroid disease can encompass hyperthyroidism, hypothyroidism, Hashimoto's disease, Graves' disease, goiter, thyroid nodules, or a combination thereof. As used herein, an arthropathy can encompass psoriatic arthritis, rheumatoid arthritis, reactive arthritis, synovitis, spondyloarthropathy, or a combination thereof. As sued herein, an inflammatory skin condition can encompass acne, acne conglobata, pilonidal disease, dissecting cellulitis, or a combination thereof. As used herein, an inflammatory bowel disease can encompass ulcerative colitis, Crohn's disease, or a combination thereof.

In some aspects, a sample obtained from a subject to obtain a gene expression profile and/or a protein expression profile as disclosed herein may be a tissue sample, a blood sample, a plasma sample, a hair sample, venous tissues, cartilage, a sperm sample, a skin sample, an amniotic fluid sample, a buccal sample, saliva, urine, serum, sputum, bone marrow or a combination thereof. In some aspects, a sample obtained from a subject to obtain a gene expression profile and/or a protein expression profile as disclosed herein may be a tissue sample. Non-limiting methods for collection of a tissue sample include microdissection, laser capture, biopsy, abdominoplasty, debridement, a punch biopsy, or a combination thereof. In some aspects, debridement may be excisional, selective, non-selective, or a combination thereof. As used herein, the term "excisional debridement" refers to the sharp removal of tissue at the wound margin or at the wound base until viable tissue is removed. As used herein, the term "selective debridement" refers to the removal of nonviable tissue. As used herein, the term "non-selective debridement" refers to the gradual removal of nonviable tissue. In some aspects, depth of debridement may be skin, fascia, subcutaneous tissue, soft tissue, muscle, or bone. Non-limiting examples of techniques suitable for debridement include use of a high pressure waterjet with/without suction, scissors, scalpel and forceps. In some aspects, the total affected area may be collected as a sample. In other aspects, multiple tissue samples may be collected from different areas on the subject's body.

In some aspects, a sample obtained from a subject to obtain a gene expression profile and/or a protein expression profile as disclosed herein may be stored at about 25° C. to about −80° C. for up to about 1 day to about 2 years, about 1 week to about 1 year, or about 1 month to about 6 months. In other aspects, a sample obtained from a subject may be immediately processed to obtain a gene expression profile and/or a protein expression profile as disclosed herein. In some other aspects, a sample obtained from a subject may be processed to obtain a gene expression profile as disclosed herein. In still other aspects, a sample obtained from a subject may be processed to obtain a protein expression profile as disclosed herein. Non-limiting examples of sample preparation methods can be found in art, for example in Gallagher & Wiley, (2012). CURRENT PROTOCOLS ESSENTIAL LABORATORY TECHNIQUES. Hoboken, N.J.: Wiley-Blackwell, the disclosures of which are incorporated herein.

In some embodiments, a gene expression profile as disclosed herein can be obtained from a sample by high-density expression array, DNA microarray, polymerase chain reaction (PCR), reverse transcriptase PCR (RT-PCR), real-time quantitative reverse transcription PCR (qRT-PCR), serial analysis of gene expression (SAGE), Spotted cDNA arrays, GeneChip, spotted oligo arrays, bead arrays, RNA Seq, tiling array, northern blotting, hybridization microarray, in situ hybridization, or a combination thereof. In some aspects, a gene expression profile as disclosed herein can be obtained by any known or future method suitable to assess gene expression. In some embodiments, a protein expression profile as disclosed herein can be obtained from a sample by Western blotting, enzyme-linked immunosorbent assay (ELISA), mass spectrometry, HPLC, flow cytometry, fluorescence-activated cell sorting (FACS), liquid chromatography-mass spectrometry (LC/MS), immunoelectrophoresis, translation complex profile sequencing (TCP-seq), protein microarray, protein chip, capture arrays, reverse phase protein microarray (RPPA), two-dimensional gel electrophoresis or (2D-PAGE), functional protein microarrays, electrospray ionization (ESI), matrix-assisted laser desorption/ionization (MALDI), or a combination thereof. In some aspects, a protein expression profile as disclosed herein can be obtained by any known or future method suitable to assess protein expression.

In some aspects, a gene expression profile as disclosed herein can be obtained using a sample from a subject wherein the data is compared to a control sample. In some aspects, a control sample may be from a subject that has not been diagnosed with HS. In other aspects, a control sample may be a tissue sample from a subject diagnosed with HS collected from a region of the body that does not have active HS. In still other aspects, a control sample may be a tissue sample from a subject presenting with at least one HS symptom collected from a region of the body that does not have an active HS symptom. In some aspects, a gene expression profile obtained from a control sample can be compared to a gene expression profile obtained from a subject diagnosed with or suspected of having HS to analyze for differential gene expression. As used herein, the term "differential expression analysis" refers to a method of taking the normalized read count data and performing statistical analysis to discover quantitative changes in expression levels between a subject with HS or suspected of having HS and a control subject. Selection of a method of differential expression analysis suitable for use herein can depend on, but is not limited to, the method of used to obtain the data, experimental design, number of data sets to be compared, or a combination thereof.

In some embodiments, a gene expression profile of a subject with HS or suspected of having HS as disclosed herein may have at least about one gene to at least about 25 genes, at least about 2 genes to at least about 20 genes, or at least about 4 genes to at least about 15 genes differentially expressed compared to a gene expression profile of a subject without HS. In some aspects, a gene expression profile of a subject with HS or suspected of having HS as disclosed herein may have at least about one gene, at least about 2 genes, at least about 4 genes, at least about 6 genes, at least about 8 genes, at least about 10 genes, at least about 15 genes, at least about 20 genes, or at least about 25 genes differentially expressed compared to a gene expression profile of a subject without HS. In some other aspects, a gene expression profile of a subject with HS or suspected of having HS as disclosed herein may have at least about one gene to at least about 25 genes, at least about 2 genes to at least about 20 genes, or at least about 4 genes to at least about 15 genes differentially expressed by about 1-fold to about 10-fold, about 1.5-fold to about 6-fold, or about 2-fold to about 4-fold compared to a gene expression profile of a subject without HS.

In some embodiments, a gene expression profile of a subject with HS or suspected of having HS as disclosed herein may have at least about one gene to at least about 12 genes, at least about 2 genes to at least about 11 genes, or at least about 3 genes to at least about 10 genes with a decrease in expression compared to a gene expression profile of a subject without HS. In some aspects, a gene expression profile of a subject with HS or suspected of having HS as disclosed herein may have at least about one gene, at least about 2 genes, at least about 3 genes, at least about 4 genes, at least about 5 genes, at least about 6 genes, at least about 7 genes, at least about 8 genes, at least about 9 genes, at least about 10 genes, at least about 11 genes, or at least about 12 genes with a decrease in expression compared to a gene expression profile of a subject without HS. In some embodiments, a gene expression profile of a subject with HS or suspected of having HS as disclosed herein may have at least about one gene to at least about 12 genes, at least about 2 genes to at least about 11 genes, or at least about 3 genes to at least about 10 genes with an about 1-fold to about 10-fold, about 1.5-fold to about 6-fold, or about 2-fold to about 4-fold decrease in expression compared to a gene expression profile of a subject without HS.

In some embodiments, a gene with a decrease in expression in a gene expression profile of a subject with HS or suspected of having HS as disclosed herein compared to a gene expression profile of a subject without HS may be dermcidin (DCD), SCGB2A2 (secretoglobin family 2A member 2, also known as Mammaglobin A), keratin 2 (KRT2), keratin 77 (KRT77), LCE2B (Late Cornified Envelope 2B) LCESA (Late Cornified Envelope 5A), C5orf46 (Chromosome 5 Open Reading Frame 46), SERPINA12 (Serpin Family A Member 12), CCL27 (C-C Motif Chemokine Ligand 27), or IL-37 (inerlukein-37). In other aspects, a gene expression profile of a subject with HS or suspected of having HS as disclosed herein may have decreased expression of dermcidin, IL-37, CCL27, Mammaglobin A, keratin 77, or a combination thereof compared to a gene expression profile of a subject without HS. In still other aspects, a gene expression profile of a subject with HS or suspected of having HS as disclosed herein may have an about 1-fold to about 10-fold, about 1.5-fold to about 6-fold, or about 2-fold to about 4-fold decrease in expression of dermcidin, IL-37, CCL27, Mammaglobin A, keratin 77, or a combination thereof compared to a gene expression profile of a subject without HS. In yet still other aspects, a gene expression profile of a subject with HS or suspected of having HS as disclosed herein may have decreased expression of dermcidin, IL-37, and CCL27 compared to a gene expression profile of a subject without HS. In some other aspects, a gene expression profile of a subject with HS or suspected of having HS as disclosed herein may have an about 1-fold to about 10-fold, about 1.5-fold to about 6-fold, or about 2-fold to about 4-fold decrease in expression of dermcidin, IL-37, and CCL27 compared to a gene expression profile of a subject without HS. In other aspects, a gene expression profile of a subject with HS or suspected of having HS as disclosed herein may have decreased expression of dermcidin and IL-37 compared to a gene expression profile of a subject without HS. In some other aspects, a gene expression profile of a subject with HS or suspected of having HS as disclosed herein may have an about 1-fold to about 10-fold, about 1.5-fold to about 6-fold, or about 2-fold to about 4-fold decrease in expression of dermcidin and IL-37 compared to a gene expression profile of a subject without HS.

In some embodiments, a gene expression profile of a subject with HS or suspected of having HS as disclosed herein may have at least about one gene to at least about 15 genes, at least about 2 genes to at least about 14 genes, or at least about 3 genes to at least about 13 genes with an increase in expression compared to a gene expression profile of a subject without HS. In some aspects, a gene expression profile of a subject with HS or suspected of having HS as disclosed herein may have at least about one gene, at least about 2 genes, at least about 3 genes, at least about 4 genes, at least about 5 genes, at least about 6 genes, at least about 7 genes, at least about 8 genes, at least about 9 genes, at least about 10 genes, at least about 11 genes, at least about 12 genes, at least about 13 genes, at least about 14 genes, or at least about 15 genes with an increase in expression compared to a gene expression profile of a subject without HS. In some embodiments, a gene expression profile of a subject with HS or suspected of having HS as disclosed herein may have at least about one gene to at least about 15 genes, at least about 2 genes to at least about 14 genes, or at least about 3 genes to at least about 13 genes with an about 1-fold to about 10-fold, about 1.5-fold to about 6-fold, or about 2-fold to about 4-fold increase in expression compared to a gene expression profile of a subject without HS.

In some embodiments, a gene with an increase in expression in a gene expression profile of a subject with HS or suspected of having HS as disclosed herein compared to a gene expression profile of a subject without HS may be ILMN_1652199, ILMN_1739508, MZB1 (Marginal Zone B And B1 Cell Specific Protein), FAM46C (family with sequence similarity 46, member C), ILMN_1680274, ILMN_1674228, IGLL3P (immunoglobulin lambda like polypeptide 3, pseudogene), ILMN_1804601, IGKV1ORY-1 (Immunoglobulin Kappa Variable 1/ORY-1 (Pseudogene)), PI3 (peptidase inhibitor 3, also known as elafin and skin-derived antileukoprotease (SKALP)), IGLL1 (immunoglobulin lambda like polypeptide 1), S100A7 (S100 calcium binding protein A7), S100A9 (S100 calcium binding protein A9), or S100A8 (S100 calcium binding protein A8). In other aspects, a gene expression profile of a subject with HS or suspected of having HS as disclosed herein may have increased expression of elafin, IGLL1, S100A7, S100A8, S100A9, or a combination thereof compared to a gene expression profile of a subject without HS. In still other aspects, a gene expression profile of a subject with HS or suspected of having HS as disclosed herein may have increased expression of S100A7, S100A8, and S100A9 compared to a gene expression profile of a subject without HS. In some other aspects, a gene expression profile of a subject with HS or suspected of having HS as disclosed herein may have an about 1-fold to about 10-fold, about 1.5-fold to about 6-fold, or about 2-fold to about 4-fold increase in expression of S100A7, S100A8, and S100A9 compared to a gene expression profile of a subject without HS. In other aspects, a gene expression profile of a subject with HS or suspected of having HS as disclosed herein may have increased expression of S100A8 and S100A8 compared to a gene expression profile of a subject without HS. In some other aspects, a gene expression profile of a subject with HS or suspected of having HS as disclosed herein may have an about 1-fold to about 10-fold, about 1.5-fold to about 6-fold, or about 2-fold to about 4-fold increase in expression of S100A8, and S100A8 compared to a gene expression profile of a subject without HS.

In some embodiments, a gene expression profile of a subject with HS or suspected of having HS as disclosed herein compared to a gene expression profile of a subject without HS may have decreased expression of dermcidin, Mammaglobin A, keratin 2, keratin 77, LCE2B, LCE5A, C5orf46, SERPINA12, CCL27, IL-37, or a combination thereof and increased expression of ILMN_1652199, ILMN_1739508, MZB1, FAM46C, ILMN_1680274, ILMN_1674228, IGLL3P, ILMN_1804601, IGKV1ORY-1, elafin, IGLL1, S100A7, S100A8, S100A9, or a combination thereof. In some aspects, a gene expression profile of a subject with HS or suspected of having HS as disclosed herein may have decreased expression of dermcidin, IL-37, CCL27, Mammaglobin A, keratin 77, or a combination thereof and increased expression of elafin, IGLL1, S100A7, S100A8, S100A9, or a combination thereof compared to a gene expression profile of a subject without HS. In other aspects, a gene expression profile of a subject with HS or suspected of having HS as disclosed herein may have an about 1-fold to about 10-fold, about 1.5-fold to about 6-fold, or about 2-fold to about 4-fold decrease in expression of dermcidin, IL-37, CCL27, Mammaglobin A, keratin 77, or a combination thereof and an about 1-fold to about 10-fold, about 1.5-fold to about 6-fold, or about 2-fold to about 4-fold increase in expression of elafin, IGLL1, S100A7, S100A8, S100A9, or a combination thereof compared to a gene expression profile of a subject without HS. In some other aspects, a gene expression profile of a subject with HS or suspected of having HS as disclosed herein may have decreased expression of dermcidin, IL-37, and CCL27 and increased expression of S100A7, S100A8, and S100A9 compared to a gene expression profile of a subject without HS. In some other aspects, a gene expression profile of a subject with HS or suspected of having HS as disclosed herein may have an about 1-fold to about 10-fold, about 1.5-fold to about 6-fold, or about 2-fold to about 4-fold decrease in expression of dermcidin, IL-37, and CCL27 and an about 1-fold to about 10-fold, about 1.5-fold to about 6-fold, or about 2-fold to about 4-fold increase in expression of S100A7, S100A8, and S100A9 compared to a gene expression profile of a subject without HS. In yet other aspects, a gene expression profile of a subject with HS or suspected of having HS as disclosed herein may have decreased expression of dermcidin and IL-37, and increased expression of S100A8, and S100A9 compared to a gene expression profile of a subject without HS. In still other aspects, a gene expression profile of a subject with HS or suspected of having HS as disclosed herein may have an about 1-fold to about 10-fold, about 1.5-fold to about 6-fold, or about 2-fold to about 4-fold decrease in expression of dermcidin and IL-37, and an about 1-fold to about 10-fold, about 1.5-fold to about 6-fold, or about 2-fold to about 4-fold increase in expression of S100A8, and S100A9 compared to a gene expression profile of a subject without HS.

In some embodiments, a gene expression profile of a subject with HS or suspected of having HS as disclosed herein encompassing decreased expression of dermcidin, Mammaglobin A, keratin 2, keratin 77, LCE2B, LCE5A, C5orf46, SERPINA12, CCL27, IL-37, or a combination thereof and increased expression of ILMN_1652199, ILMN_1739508, MZB1, FAM46C, ILMN_1680274, ILMN_1674228, IGLL3P, ILMN_1804601, IGKV1ORY-1, elafin, IGLL1, S100A7, S100A8, S100A9, or a combination thereof compared to a gene expression profile of a subject without HS can be diagnosed as having HS.

In some aspects, a gene expression profile of a subject with HS or suspected of having HS as disclosed herein encompassing decreased expression of dermcidin, Mammaglobin A, keratin 77, CCL27, IL-37, or a combination thereof and increased expression of elafin, S100A7, S100A8, S100A9, or a combination thereof compared to a gene expression profile of a subject without HS can be diagnosed as having HS. In other aspects, a gene expression profile of a subject with HS or suspected of having HS as disclosed herein encompassing a an about 1-fold to about 10-fold, about 1.5-fold to about 6-fold, or about 2-fold to about 4-fold decrease in expression of dermcidin, Mammaglobin A, keratin 77, CCL27, IL-37, or a combination thereof and an about 1-fold to about 10-fold, about 1.5-fold to about 6-fold, or about 2-fold to about 4-fold increase in expression of elafin, S100A7, S100A8, S100A9, or a combination thereof compared to a gene expression profile of a subject without HS can be diagnosed as having HS.

In some other aspects, a gene expression profile of a subject with HS or suspected of having HS as disclosed herein encompassing decreased expression of dermcidin, CCL27 and IL-37 and increased expression of S100A7, S100A8 and S100A9 compared to a gene expression profile of a subject without HS can be diagnosed as having HS. In still some other aspects, a gene expression profile of a subject with HS or suspected of having HS as disclosed herein encompassing a an about 1-fold to about 10-fold, about 1.5-fold to about 6-fold, or about 2-fold to about 4-fold decrease in expression of dermcidin, CCL27 and IL-37 and an about 1-fold to about 10-fold, about 1.5-fold to about 6-fold, or about 2-fold to about 4-fold increase in expression of S100A7, S100A8, and S100A9 compared to a gene expression profile of a subject without HS can be diagnosed as having HS.

In yet some other aspects, a gene expression profile of a subject with HS or suspected of having HS as disclosed herein encompassing decreased expression of dermcidin and IL-37, and increased expression of S100A8 and S100A9 compared to a gene expression profile of a subject without HS can be diagnosed as having HS. In other aspects, a gene expression profile of a subject with HS or suspected of having HS as disclosed herein encompassing an about 1-fold to about 10-fold, about 1.5-fold to about 6-fold, or about 2-fold to about 4-fold decrease in expression of dermcidin and IL-37 and an about 1-fold to about 10-fold, about 1.5-fold to about 6-fold, or about 2-fold to about 4-fold increase in expression of S100A8 and S100A9 compared to a gene expression profile of a subject without HS can be diagnosed as having HS.

In some embodiments, a gene expression profile of a subject with HS or suspected of having HS as disclosed herein encompassing at least about 1.5-fold to about 6-fold decrease in expression of dermcidin, Mammaglobin A, keratin 77, CCL27, IL-37, or a combination thereof and at least about 1.5-fold to about 6-fold increase in expression of S100A8, S100A9, or a combination thereof compared to a gene expression profile of a subject without HS can be diagnosed as having moderate to severe HS. In some aspects, a gene expression profile of a subject with HS or suspected of having HS as disclosed herein encompassing at least about 1.5-fold to about 6-fold decrease in expression of dermcidin, CCL27, IL-37, or a combination thereof and at least about 1.5-fold to about 6-fold increase in expression of S100A8, S100A9, or a combination thereof compared to a gene expression profile of a subject without HS can be diagnosed as having moderate to severe HS. In some aspects, a gene expression profile of a subject with HS or suspected of having HS as disclosed herein encompassing at least about 1.5-fold to about 6-fold decrease in expression of dermcidin, CCL27, IL-37, or a combination thereof and at least about 1.5-fold to about 6-fold increase in expression of S100A8, S100A9, or a combination thereof compared to a gene expression profile of a subject without HS can be diagnosed as having moderate to severe HS. In some other aspects, a gene expression profile of a subject with HS or suspected of having HS as disclosed herein encompassing at least about 1.5-fold to about 6-fold decrease in expression of dermcidin and IL-37 and at least about 1.5-fold to about 6-fold increase in expression of S100A8 and S100A9 compared to a gene expression profile of a subject without HS can be diagnosed as having moderate to severe HS.

In some embodiments, a gene expression profile of a subject with HS or suspected of having HS as disclosed herein encompassing at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS can be diagnosed as having mild to moderate HS.

In some embodiments, a gene expression profile of a subject with HS or suspected of having HS as disclosed herein may encompass an increase in expression of interferon signaling pathway genes compared to a gene expression profile of a subject without HS. In some aspects, a gene expression profile of a subject with HS or suspected of having HS as disclosed herein may encompass an about 40% to about 50% increase in expression of interferon signaling pathway genes compared to a gene expression profile of a subject without HS. In other aspects, a gene expression profile of a subject with HS or suspected of having HS as disclosed herein may encompass an about 40% to about 50% increase in expression of interferon signaling pathway genes selected from the group of IFIT3, OAS1, MX1, PIAS1, TYK2, IFI35, IRF9, PSMB8, BAX, IFNAR2, IFITM2, IRF1, BCL2, IFITM3, STAT2, IFI6, STAT1, IFITM1, and IFNAR1 compared to a gene expression profile of a subject without HS. In some aspects, a gene expression profile of a subject with HS or suspected of having HS as disclosed herein may encompass an about 40% to about 50% increase in expression of interferon signaling pathway genes and an about 5% to about 10% decrease in expression of interferon signaling pathway genes compared to a gene expression profile of a subject without HS.

In some aspects, a gene expression profile of a subject with HS or suspected of having HS as disclosed herein may encompass about a 2-fold to about a 5-fold, about a 2.5-fold to about a 4.5-fold, or about a 3-fold to about a 4-fold increase in expression of IF16, IFI35, IFITM1, IFITM2, IFITM3, IFNAR2, IRF1, MX1, STAT1, or a combination thereof compared to a gene expression profile of a subject without HS. In other aspects, a gene expression profile of a subject with HS or suspected of having HS as disclosed herein may encompass about a 2.5-fold to about 5-fold, about 2.7-fold to about 4.7-fold, or about 3-fold to about 4.5-fold increase in expression of IFITM1, IFNAR2, IRF1, STAT1, or a combination thereof compared to a gene expression profile of a subject without HS. In some other aspects, a gene expression profile of a subject with HS or suspected of having HS as disclosed herein may encompass about a 2-fold to about a 4-fold, about a 1.5-fold to about a 3.5-fold, or about a 1-fold to about a 3-fold decrease in expression of BCL2, PIAS1, or a combination thereof compared to a gene expression profile of a subject without HS.

In some embodiments, a subject with HS or suspected of having HS with a gene expression profile encompassing about a 2-fold to about a 5-fold, about a 2.5-fold to about a 4.5-fold, or about a 3-fold to about a 4-fold increase in expression of IF16, IFI35, IFITM1, IFITM2, IFITM3, IFNAR2, IRF1, MX1, STAT1, or a combination thereof compared to a gene expression profile of a subject without HS and about a 4-fold, about a 1.5-fold to about a 3.5-fold, or about a 1-fold to about a 3-fold decrease in expression of BCL2, PIAS1, or a combination thereof compared to a gene expression profile of a subject without HS may be diagnosed with HS. In some aspects, a subject with HS or suspected of having HS with a gene expression profile encompassing about a 2.5-fold to about a 5-fold, about 2.7-fold to about 4.7-fold, or about a 3-fold to about a 4.5-fold increase in expression of IFITM1, IFNAR2, IRF1, STAT1, or a combination thereof compared to a gene expression profile of a subject without HS and about a 4-fold, about a 1.5-fold to about a 3.5-fold, or about a 1-fold to about a 3-fold decrease in expression of BCL2, PIAS1, or a combination thereof compared to a gene expression profile of a subject without HS may be diagnosed with moderate to severe HS.

In some embodiments, a gene expression profile of a subject with HS or suspected of having HS as disclosed herein may encompass an increase in expression of leucocyte extravasation signaling genes compared to a gene expression profile of a subject without HS. In some aspects, a gene expression profile of a subject with HS or suspected of having HS as disclosed herein may encompass an about 10% to about 20% increase in expression of leucocyte extravasation signaling pathway genes compared to a gene expression profile of a subject without HS. In other aspects, a gene expression profile of a subject with HS or suspected of having HS as disclosed herein may encompass an about 10% to about 20% increase in expression of leucocyte extravasation signaling pathway genes selected from the group of MAP2K4, RAC2, MYL6, MMP3, PIK3R1, WASL, CXCL12, PIK3CG, EZR, CYBA, CYBB, ARHGAP12, IRS2, ITGA4, ITK, PRKCQ, THY1, NCF4, TLR9, MMP27, NCF1, CLDN23, MMP23B, CLDN8, RAP1GAP, ICAM3, PLCG2, PECAM1, VAV1, PIK3CD, CLDN14, ACTN4, ARHGAP1, CLDN11, CTNNA1, RAPGEF4, TIMP1, SIPA1, ACTN1, VCAM1, MMP28, CXCR4, GRB2, ACTB, ARHGAP4, GNAI1, PIK3C2G, BTK, GNAI2, ITGB2, WIPF1, ARHGAP9, WAS, CLDN1, MMP9, CTNND1, and MSN compared to a gene expression profile of a subject without HS. In some aspects, a gene expression profile of a subject with HS or suspected of having HS as disclosed herein may encompass an about 10% to about 20% increase in expression of leucocyte extravasation signaling pathway genes and an about 5% to about 10% decrease in expression of leucocyte extravasation signaling pathway genes compared to a gene expression profile of a subject without HS.

In some aspects, a gene expression profile of a subject with HS or suspected of having HS as disclosed herein may encompass about a 2-fold to about a 15-fold, about a 2.5-fold to about a 10-fold, or about a 3-fold to about a 8-fold increase in expression of ITGB2, CYBA, RAC2, THY1, VCAM1, PECAM1, PLCG2, ICAM3, WAS, MMP9, CXCL12, BTK, MMP3, CXCR4, or a combination thereof compared to a gene expression profile of a subject without HS. In other aspects, a gene expression profile of a subject with HS or suspected of having HS as disclosed herein may encompass about a 4-fold to about 15-fold, about 5-fold to about 14-fold, or about 6-fold to about 13-fold increase in expression of CYBA, THY1, MMP9, MMP3, or a combination thereof compared to a gene expression profile of a subject without HS. In some other aspects, a gene expression profile of a subject with HS or suspected of having HS as disclosed herein may encompass about a 2-fold to about a 4-fold, about a 1.5-fold to about a 3.5-fold, or about a 1-fold to about a 3-fold decrease in expression of TIMP1, ARHGAP9, ARHGAP4, or a combination thereof compared to a gene expression profile of a subject without HS.

In some embodiments, a subject with HS or suspected of having HS with a gene expression profile encompassing about a 2-fold to about a 15-fold, about a 2.5-fold to about a 10-fold, or about a 3-fold to about a 8-fold increase in expression of ITGB2, CYBA, RAC2, THY1, VCAM1, PECAM1, PLCG2, ICAM3, WAS, MMP9, CXCL12, BTK, MMP3, CXCR4, or a combination thereof compared to a gene expression profile of a subject without HS and about a 2-fold to about a 4-fold, about a 1.5-fold to about a 3.5-fold, or about a 1-fold to about a 3-fold decrease in expression of TIMP1, ARHGAP9, ARHGAP4, or a combination thereof compared to a gene expression profile of a subject without HS may be diagnosed with HS. In some aspects, a subject with HS or suspected of having HS with a gene expression profile encompassing about a 4-fold to about 15-fold, about 5-fold to about 14-fold, or about 6-fold to about 13-fold increase in expression of CYBA, THY1, MMP9, MMP3, or a combination thereof compared to a gene expression profile of a subject without HS and about a 2-fold to about a 4-fold, about a 1.5-fold to about a 3.5-fold, or about a 1-fold to about a 3-fold decrease in expression of TIMP1, ARHGAP9, ARHGAP4, or a combination thereof compared to a gene expression profile of a subject without HS may be diagnosed with moderate to severe HS.

In some embodiments, a gene expression profile of a subject with HS or suspected of having HS as disclosed herein may encompass an increase in expression of T helper type 1 (Th1) pathway genes compared to a gene expression profile of a subject without HS. In some aspects, a gene expression profile of a subject with HS or suspected of having HS as disclosed herein may encompass an about 20% to about 30% increase in expression of Th1 pathway genes compared to a gene expression profile of a subject without HS. In other aspects, a gene expression profile of a subject with HS or suspected of having HS as disclosed herein may encompass an about 20% to about 30% increase in expression of Th1 genes selected from the group of CD247, SOCS3, NFATC3, PIK3R1, CD4, HLA-DQA1, NCSTN, LGALS9, IL6, CD8A, HLA-DQB2, HLA-DMA, PIK3CG, HLA-DRA, HLA-DMB, IRS2, STAT1, HLA-DPB1, PRKCQ, GRB2, TYK2, PIK3C2G, STAT3, TLR9, CD3D, IRF1, STAT4, ITGB2, ICOS, IL10RB, IL10RA, HLA-DOB, APH1B, CD86, VAV1, PIK3CD, GATA3, mir-21, and IFNAR1 compared to a gene expression profile of a subject without HS. In some aspects, a gene expression profile of a subject with HS or suspected of having HS as disclosed herein may encompass an about 20% to about 30% increase in expression of Th1 pathway genes and an about 5% to about 10% decrease in expression of Th1 pathway genes compared to a gene expression profile of a subject without HS.

In some aspects, a gene expression profile of a subject with HS or suspected of having HS as disclosed herein may encompass about a 2-fold to about a 10-fold, about a 2.5-fold to about a 8-fold, or about a 3-fold to about a 6-fold increase in expression of CD86, CD247, CD3D, HLA-DMA, HLS-DMB, IL6, STAT1, STAT4, or a combination thereof compared to a gene expression profile of a subject without HS. In other aspects, a gene expression profile of a subject with HS or suspected of having HS as disclosed herein may encompass about a 3-fold to about 12-fold, about 4-fold to about 10-fold, or about 6-fold to about 10-fold increase in expression of CD86, CD247, IL6, STAT1, or a combination thereof compared to a gene expression profile of a subject without HS. In some other aspects, a gene expression profile of a subject with HS or suspected of having HS as disclosed herein may encompass about a 2-fold to about a 4-fold, about a 1.5-fold to about a 3.5-fold, or about a 1-fold to about a 3-fold decrease in expression of IRF1, SOCS3, or a combination thereof compared to a gene expression profile of a subject without HS.

In some embodiments, a subject with HS or suspected of having HS with a gene expression profile encompassing about a 2-fold to about a 10-fold, about a 2.5-fold to about a 8-fold, or about a 3-fold to about a 6-fold increase in expression of CD86, CD247, CD3D, HLA-DMA, HLS-DMB, IL6, STAT1, or a combination thereof compared to a gene expression profile of a subject without HS and about a 2-fold to about a 4-fold, about a 1.5-fold to about a 3.5-fold, or about a 1-fold to about a 3-fold decrease in expression of IRF1, SOCS3, or a combination thereof compared to a gene expression profile of a subject without HS may be diagnosed with HS. In some aspects, a subject with HS or suspected of having HS with a gene expression profile encompassing about a 3-fold to about 12-fold, about 4-fold to about 10-fold, or about 6-fold to about 10-fold increase in expression of CD86, CD247, IL6, STAT1, or a combination thereof compared to a gene expression profile of a subject without HS and about a 2-fold to about a 4-fold, about a 1.5-fold to about a 3.5-fold, or about a 1-fold to about a 3-fold decrease in expression of IRF1, SOCS3, or a combination thereof compared to a gene expression profile of a subject without HS may be diagnosed with moderate to severe HS.

In some embodiments, a gene expression profile of a subject with HS or suspected of having HS as disclosed herein may encompass an increase in expression of T helper type 2 (Th2) pathway genes compared to a gene expression profile of a subject without HS. In some aspects, a gene expression profile of a subject with HS or suspected of having HS as disclosed herein may encompass an about 20% to about 30% increase in expression of Th2 pathway genes compared to a gene expression profile of a subject without HS. In other aspects, a gene expression profile of a subject with HS or suspected of having HS as disclosed herein may encompass an about 20% to about 30% increase in expression of Th2 genes selected from the group of CD247, SOCS3, TNFRSF4, IL1RL1, TGFBR3, PIK3R1, CD4, HLA-DQA1, NCSTN, HLA-DQB2, HLA-DMA, PIK3CG, HLA-DRA, HLA-DMB, IRS2, HLA-DPB1, IL4R, JAG2, PRKCQ, CXCR4, GRB2, TYK2, PIK3C2G, TLR9, IL24, CD3D, ACVR1B, STAT4, ITGB2, ICOS, S1PR1, HLA-DOB, APH1B, CD86, VAV1, PIK3CD, GATA3, mir-21, and ACVR2A compared to a gene expression profile of a subject without HS. In some aspects, a gene expression profile of a subject with HS or suspected of having HS as disclosed herein may encompass an about 20% to about 30% increase in expression of Th2 pathway genes and an about 5% to about 10% decrease in expression of Th2 pathway genes compared to a gene expression profile of a subject without HS.

In some aspects, a gene expression profile of a subject with HS or suspected of having HS as disclosed herein may encompass about a 1.5-fold to about a 8-fold, about a 2-fold to about a 6-fold, or about a 2.5-fold to about a 4-fold increase in expression of CD86, CD247, CD3D, CXCR4, IL4R, or a combination thereof compared to a gene expression profile of a subject without HS. In other aspects, a gene expression profile of a subject with HS or suspected of having HS as disclosed herein may encompass about a 2-fold to about 8-fold, about 2.5-fold to about 6-fold, or about 3-fold to about 4-fold increase in expression of CD247, CD3D, CXCR4, IL4R, or a combination thereof compared to a gene expression profile of a subject without HS. In some other aspects, a gene expression profile of a subject with HS or suspected of having HS as disclosed herein may encompass about a 1.5-fold to about a 4-fold, about a 2-fold to about a 3.5-fold, or about a 2.5-fold to about a 3-fold decrease in expression of S1PR1, STAT4, or a combination thereof compared to a gene expression profile of a subject without HS.

In some embodiments, a subject with HS or suspected of having HS with a gene expression profile encompassing about a 1.5-fold to about a 8-fold, about a 2-fold to about a 6-fold, or about a 2.5-fold to about a 4-fold increase in expression of CD86, CD247, CD3D, CXCR4, IL4R, or a combination thereof compared to a gene expression profile of a subject without HS and about a 1.5-fold to about a 4-fold, about a 2-fold to about a 3.5-fold, or about a 2.5-fold to about a 3-fold decrease in expression of S1PR1, STAT4, or a combination thereof compared to a gene expression profile of a subject without HS may be diagnosed with HS. In some aspects, a subject with HS or suspected of having HS with a gene expression profile encompassing about a 2-fold to about 8-fold, about 2.5-fold to about 6-fold, or about 3-fold to about 4-fold increase in expression of CD247, CD3D, CXCR4, IL4R, or a combination thereof compared to a gene expression profile of a subject without HS and about a 1.5-fold to about a 4-fold, about a 2-fold to about a 3.5-fold, or about a 2.5-fold to about a 3-fold decrease in expression of S1PR1, STAT4, or a combination thereof compared to a gene expression profile of a subject without HS may be diagnosed with moderate to severe HS.

In some embodiments, a gene expression profile of a subject with HS or suspected of having HS as disclosed herein may encompass an increase in expression of nuclear factor of activated T-cells (NFAT) pathway genes compared to a gene expression profile of a subject without HS. In some aspects, a gene expression profile of a subject with HS or suspected of having HS as disclosed herein may encompass an about 20% to about 30% increase in expression of NFAT pathway genes compared to a gene expression profile of a subject without HS. In other aspects, a gene expression profile of a subject with HS or suspected of having HS as disclosed herein may encompass an about 20% to about 30% increase in expression of NFAT pathway genes selected from the group of CD247, PLCB2, NFATC3, PIK3R1, CD4, GNA11, HLA-DQA1, FCER1A, FCGR1A, HLA-DMA, PIK3CG, HLA-DRA, HLA-DMB, IRS2, MAP2K1, FCGR3A/FCGR3B, GNG12, FCGR1B, ORAI1, ITK, PRKCQ, CD79B, FCGR2A, ITPR2, GRB2, GNA12, PIK3C2G, GNAI1, CSNK1D, CD79A, TLR9, CD3D, BTK, GNAI2, RCAN1, RRAS2, PLCG2, SYK, ITPR3, LYN, FCER1G, HLA-DOB, CD86, and PIK3CD compared to a gene expression profile of a subject without HS. In some aspects, a gene expression profile of a subject with HS or suspected of having HS as disclosed herein may encompass an about 20% to about 30% increase in expression of NFAT pathway genes and an about 5% to about 10% decrease in expression of NFAT pathway genes compared to a gene expression profile of a subject without HS.

In some aspects, a gene expression profile of a subject with HS or suspected of having HS as disclosed herein may encompass about a 2-fold to about a 15-fold, about a 2.5-fold to about a 10-fold, or about a 3-fold to about a 8-fold increase in expression of BTK, CD86, CD247, CD3D, CD79A, CD79B, FCER1G, FCGR1B, FCGR2A, HLA-DMA, HLA-DMB, PLCG2, or a combination thereof compared to a gene expression profile of a subject without HS. In other aspects, a gene expression profile of a subject with HS or suspected of having HS as disclosed herein may encompass about a 3-fold to about 15-fold, about 4-fold to about 14-fold, or about 5-fold to about 13-fold increase in expression of CD247, CD3D, CD79A, PLCG2, or a combination thereof compared to a gene expression profile of a subject without HS. In some other aspects, a gene expression profile of a subject with HS or suspected of having HS as disclosed herein may encompass about a 1.5-fold to about a 4-fold, about a 2-fold to about a 3.5-fold, or about a 2.5-fold to about a 3-fold decrease in expression of RCAN1 compared to a gene expression profile of a subject without HS.

In some embodiments, a subject with HS or suspected of having HS with a gene expression profile encompassing about a 2-fold to about a 15-fold, about a 2.5-fold to about a 10-fold, or about a 3-fold to about a 8-fold increase in expression of BTK, CD86, CD247, CD3D, CD79A, CD79B, FCER1G, FCGR1B, FCGR2A, HLA-DMA, HLA-DMB, PLCG2, or a combination thereof compared to a gene expression profile of a subject without HS and about a 1.5-fold to about a 4-fold, about a 2-fold to about a 3.5-fold, or about a 2.5-fold to about a 3-fold decrease in expression of RCAN1 compared to a gene expression profile of a subject without HS may be diagnosed with HS. In some aspects, a subject with HS or suspected of having HS with a gene expression profile encompassing about a 3-fold to about 15-fold, about 4-fold to about 14-fold, or about 5-fold to about 13-fold increase in expression of CD247, CD3D, CD79A, PLCG2, or a combination thereof compared to a gene expression profile of a subject without HS and about a 1.5-fold to about a 4-fold, about a 2-fold to about a 3.5-fold, or about a 2.5-fold to about a 3-fold decrease in expression of RCAN1 compared to a gene expression profile of a subject without HS may be diagnosed with moderate to severe HS.

In some embodiments, a subject with HS or suspected of having HS with a gene expression profile encompassing about a 1.5-fold to about a 15-fold, about a 2-fold to about a 14 fold, or about a 3-fold to about a 13-fold increase in expression of S100A7, S100A8, S100A9, IF16, IFI35, IFITM1, IFITM2, IFITM3, IFNAR2, IRF1, NFATC3, MX1, STAT1, ITGB2, CYBA, RAC2, THY1, VCAM1, PECAM1, PLCG2, ICAM3, WAS, MMP9, CXCL12, BTK, MMP3, CXCR4, CD86, CD247, CD3D, HLA-DMA, HLS-DMB, IL6, IL4R, BTK, CD79A, CD79B, FCER1G, FCGR1B, FCGR2A, PLCG2, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, Mammaglobin A, keratin 77, CCL27, IL-37, BCL2, PIAS1, TIMP1, ARHGAP9, ARHGAP4, IRF1, SOCS3, S1PR1, STAT4, RCAN1, or a combination thereof compared to a gene expression profile of a subject without HS may be diagnosed with HS. In some aspects, a subject with HS or suspected of having HS with a gene expression profile encompassing about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS may be diagnosed with moderate severe HS.

In some embodiments, a gene expression profile of a subject with HS or suspected of having HS as disclosed herein may encompass an increase in expression of tyrosine-protein kinase Tec signaling pathway genes compared to a gene expression profile of a subject without HS. In some aspects, a gene expression profile of a subject with HS or suspected of having HS as disclosed herein may encompass an about 10% to about 20% increase in expression of tyrosine-protein kinase Tec signaling pathway genes compared to a gene expression profile of a subject without HS. In other aspects, a gene expression profile of a subject with HS or suspected of having HS as disclosed herein may encompass an about 10% to about 20% increase in expression of tyrosine-protein kinase Tec signaling pathway genes selected from the group of MAP2K4, PIK3R1, GNA11, FCER1A, TNFSF10, RHOG, RHOT1, PIK3CG, IRS2, STAT1, GNG12, FGR, ITGA4, ITK, RND2, TNFRSF21, PAK4, PRKCQ, PAK6, GRB2, GNA12, ACTB, TYK2, TNFRSF10B, GNAI1, PIK3C2G, STAT3, TLR9, BTK, GNAI2, STAT4, RHOV, WAS, PLCG2, TNFRSF25, PAK2, LYN, FCER1G, VAV1, STAT2, and PIK3CD compared to a gene expression profile of a subject without HS. In some aspects, a gene expression profile of a subject with HS or suspected of having HS as disclosed herein may encompass an about 10% to about 20% increase in expression of tyrosine-protein kinase Tec signaling pathway genes and an about 5% to about 10% decrease in expression of tyrosine-protein kinase Tec signaling pathway genes compared to a gene expression profile of a subject without HS.

In some embodiments, a gene expression profile of a subject with HS or suspected of having HS as disclosed herein may encompass an increase in expression of dendritic cell maturation pathway genes compared to a gene expression profile of a subject without HS. In some aspects, a gene expression profile of a subject with HS or suspected of having HS as disclosed herein may encompass an about 10% to about 20% increase in expression of dendritic cell maturation pathway genes compared to a gene expression profile of a subject without HS. In other aspects, a gene expression profile of a subject with HS or suspected of having HS as disclosed herein may encompass an about 10% to about 20% increase in expression of dendritic cell maturation pathway genes selected from the group of MAP2K4, PLCB2, LEPR, IL32, PIK3R1, HLA-DQA1, LTB, IL1F10, IL6, PLCH2, FCGR1A, PLCD3, IL1RL2, HLA-DMA, PIK3CG, HLA-DRA, HLA-DMB, IRS2, TNFRSF1B, IL23A, STAT1, FCGR3A/FCGR3B, FCGR1B, FCGR2A, MYD88, TYROBP, GRB2, PIK3C2G, IL36A, IL37, TLR9, STAT4, PLCG2, FSCN1, FCER1G, HLA-DOB, IL1B, CD86, STAT2, PIK3CD, IRF8, CCR7, and IFNAR1 compared to a gene expression profile of a subject without HS. In some aspects, a gene expression profile of a subject with HS or suspected of having HS as disclosed herein may encompass an about 10% to about 20% increase in expression of dendritic cell maturation pathway genes and an about 5% to about 10% decrease in expression of dendritic cell maturation pathway genes compared to a gene expression profile of a subject without HS.

In some embodiments, a gene expression profile of a subject with HS or suspected of having HS as disclosed herein may encompass an increase in expression of neuro-inflammation signaling pathway genes compared to a gene expression profile of a subject without HS. In some aspects, a gene expression profile of a subject with HS or suspected of having HS as disclosed herein may encompass an about 10% to about 20% increase in expression of neuro-inflammation signaling pathway genes compared to a gene expression profile of a subject without HS. In other aspects, a gene expression profile of a subject with HS or suspected of having HS as disclosed herein may encompass an about 10% to about 20% increase in expression of neuro-inflammation signaling pathway genes selected from the group of MAP2K4, MMP3, NFATC3, TGFBR3, PIK3R1, TLR8, CXCL12, NCSTN, IL6, CXCL10, SOD2, PIK3CG, CYBB, IRS2, CXCL8, CASP3, TYK2, TLR9, ACVR1B, IRF7, PLCG2, SYK, KCNJS, GAD1, MAPT, SLC6A1, APH1B, CD86, PIK3CD, KLK1, SNCA, KLK3, HLA-DQA1, SLC1A3, CCL5, BCL2, GABRB3, CCL2, HLA-DMA, GABRA6, HLA-DRA, IL34, HLA-DMB, CASP1, TLR7, STAT1, NFE2L2, VCAM1, TYROBP, MYD88, GRB2, PIK3C2G, GABRE, APP, GABRP, PLA2G4A, HLA-DOB, IL1B, MMP9, ACVR2A, and BIRC2 compared to a gene expression profile of a subject without HS. In some aspects, a gene expression profile of a subject with HS or suspected of having HS as disclosed herein may encompass an about 10% to about 20% increase in expression of neuro-inflammation signaling pathway genes and an about 5% to about 10% decrease in expression of neuro-inflammation signaling pathway genes compared to a gene expression profile of a subject without HS.

In some embodiments, a gene expression profile of a subject with HS or suspected of having HS as disclosed herein may encompass an increase in expression of JAK/STAT signaling pathway genes compared to a gene expression profile of a subject without HS. In some aspects, a gene expression profile of a subject with HS or suspected of having HS as disclosed herein may encompass an about 15% to about 25% increase in expression of JAK/STAT signaling pathway genes compared to a gene expression profile of a subject without HS. In other aspects, a gene expression profile of a subject with HS or suspected of having HS as disclosed herein may encompass an about 15% to about 25% increase in expression JAK/STAT signaling pathway genes selected from the group of SOCS3, PTPN6, GRB2, PIK3R1, SOCS6, PIAS1, TYK2, PIK3C2G, STAT3, IL6, TLR9, STAT4, SHC1, BCL2L1, PIAS3, RRAS2, PIK3CG, PIK3CD, IRS2, STAT2, STAT1, and MAP2K1 compared to a gene expression profile of a subject without HS. In some aspects, a gene expression profile of a subject with HS or suspected of having HS as disclosed herein may encompass an about 15% to about 25% increase in expression of JAK/STAT signaling pathway genes and an about 5% to about 10% decrease in expression of JAK/STAT signaling pathway genes compared to a gene expression profile of a subject without HS.

In some embodiments, a gene expression profile of a subject with HS or suspected of having HS as disclosed herein may encompass an increase in expression of Oncostatin M signaling pathway genes compared to a gene expression profile of a subject without HS. In some aspects, a gene expression profile of a subject with HS or suspected of having HS as disclosed herein may encompass an about 30% to about 40% increase in expression of Oncostatin M signaling pathway genes compared to a gene expression profile of a subject without HS. In other aspects, a gene expression profile of a subject with HS or suspected of having HS as disclosed herein may encompass an about 30% to about 40% increase in expression Oncostatin M signaling pathway genes selected from the group of MT2A, SHC1, EPAS1, RRAS2, MMP3, GRB2, TYK2, OSMR, PLAU, STAT3, STAT1, and MAP2K1 compared to a gene expression profile of a subject without HS. In some aspects, a gene expression profile of a subject with HS or suspected of having HS as disclosed herein may encompass an about 30% to about 40% increase in expression of Oncostatin M signaling pathway genes and an about less than 0.5% decrease in expression of Oncostatin M signaling pathway genes compared to a gene expression profile of a subject without HS. In other aspects, a gene expression profile of a subject with HS or suspected of having HS as disclosed herein may encompass an about 30% to about 40% increase in expression of Oncostatin M signaling pathway genes and no decrease in expression of Oncostatin M signaling pathway genes compared to a gene expression profile of a subject without HS.

In some embodiments, a gene expression profile of a subject with HS or suspected of having HS as disclosed herein may encompass an increase in expression of FcγRIIB signaling pathway genes that exert on inhibitory effect on B cells compared to a gene expression profile of a subject without HS. As used herein, "FcγRIIB" refers an inhibitory IgG FcR in the classical FcR family with a tyrosine-based inhibitory motif. In some aspects, a gene expression profile of a subject with HS or suspected of having HS as disclosed herein may encompass an about 20% to about 30% increase in expression of FcγRIIB signaling pathway genes that exert on inhibitory effect on B cells compared to a gene expression profile of a subject without HS. In other aspects, a gene expression profile of a subject with HS or suspected of having HS as disclosed herein may encompass an about 20% to about 30% increase in expression FcγRIIB signaling pathway genes that exert on inhibitory effect on B cells selected from the group of MAP2K4, CD79B, GRB2, PIK3R1, PIK3C2G, CD79A, TLR9, BTK, SHC1, RRAS2, PIK3CG, PLCG2, and SYK compared to a gene expression profile of a subject without HS. In some aspects, a gene expression profile of a subject with HS or suspected of having HS as disclosed herein may encompass an about 20% to about 30% increase in expression of FcγRIIB signaling pathway genes that exert on inhibitory effect on B cells and an about 5% to about 10% decrease in expression of FcγRIIB signaling pathway genes that exert on inhibitory effect on B cells compared to a gene expression profile of a subject without HS.

In some embodiments, a gene expression profile of a subject with HS or suspected of having HS as disclosed herein may encompass an increase in expression of IL-6 signaling pathway genes compared to a gene expression profile of a subject without HS. In some aspects, a gene expression profile of a subject with HS or suspected of having HS as disclosed herein may encompass an about 10% to about 20% increase in expression of IL-6 signaling pathway genes compared to a gene expression profile of a subject without HS. In other aspects, a gene expression profile of a subject with HS or suspected of having HS as disclosed herein may encompass an about 10% to about 20% increase in expression of IL-6 signaling pathway genes selected from the group of MAP2K4, HSPB3, SOCS3, IL1RL1, PIK3R1, IL1F10, IL6, SHC1, IL1RL2, PIK3CG, MAP3K7, IRS2, MAPKAPK2, TNFRSF1B, MAP2K1, MCL1, CXCL8, TNFAIP6, GRB2, IL36A, PIK3C2G, IL37, STAT3, TLR9, IL18RAP, RRAS2, IL1B, CD14, PIK3CD, and A2M compared to a gene expression profile of a subject without HS. In some aspects, a gene expression profile of a subject with HS or suspected of having HS as disclosed herein may encompass an about 10% to about 20% increase in expression of IL-6 signaling pathway genes and an about 5% to about 10% decrease in expression of IL-6 signaling pathway genes compared to a gene expression profile of a subject without HS.

In some embodiments, a gene expression profile of a subject with HS or suspected of having HS as disclosed herein may encompass an increase in expression of genes that stimulate production of nitric oxide (NO) and reactive oxygen species (ROS) in macrophages compared to a gene expression profile of a subject without HS. In some aspects, a gene expression profile of a subject with HS or suspected of having HS as disclosed herein may encompass an about 10% to about 20% increase in expression of genes that stimulate production of NO and ROS in macrophages compared to a gene expression profile of a subject without HS. In other aspects, a gene expression profile of a subject with HS or suspected of having HS as disclosed herein may encompass an about 10% to about 20% increase in expression of genes that stimulate production of NO and ROS in macrophages selected from the group of MAP2K4, PPP2R2A, PIK3R1, PPP1CB, MAP3K5, PPP1R14B, LYS, RHOG, RHOT1, CYBA, PIK3CG, PPM1L, CYBB, MAP3K7, SERPINA1, S100A8, IRS2, STAT1, TNFRSF1B, MAP2K1, RND2, PPP1R14C, PTPN6, PRKCQ, MAP3K6, GRB2, TYK2, PIK3C2G, NCF4, TLR9, IRF1, APOL1, RHOV, NCF1, PLCG2, PPP2R2B, CAT, PIK3CD, IRF8, MAP3K3, and APOD compared to a gene expression profile of a subject without HS. In some aspects, a gene expression profile of a subject with HS or suspected of having HS as disclosed herein may encompass an about 10% to about 20% increase in expression of genes that stimulate production of NO and ROS in macrophages and an about 5% to about 10% decrease in expression of genes that stimulate production of NO and ROS in macrophages compared to a gene expression profile of a subject without HS.

In some embodiments, a gene expression profile of a subject with HS or suspected of having HS as disclosed herein may encompass an increase in expression of TREM1 (Triggering Receptor Expressed On Myeloid Cells 1) signaling pathway genes compared to a gene expression profile of a subject without HS. In some aspects, a gene expression profile of a subject with HS or suspected of having HS as disclosed herein may encompass an about 20% to about 30% increase in expression of TREM1 signaling pathway genes compared to a gene expression profile of a subject without HS. In other aspects, a gene expression profile of a subject with HS or suspected of having HS as disclosed herein may encompass an about 20% to about 30% increase in expression of TREM1 signaling pathway genes selected from the group of SIGIRR, CXCL8, GRB2, TYROBP, IL1RL1, MYD88, LAT2, TLR8, STAT3, IL6, TLR9, NLRP9, CCL2, PLCG2, TLR7, CASP1, CD86, IL1B, and ITGAX compared to a gene expression profile of a subject without HS. In some aspects, a gene expression profile of a subject with HS or suspected of having HS as disclosed herein may encompass an about 20% to about 30% increase in expression of TREM1 signaling pathway genes and an about 0.1% to about 5% decrease in expression of TREM1 signaling pathway genes compared to a gene expression profile of a subject without HS.

In some embodiments, a gene expression profile of a subject with HS or suspected of having HS as disclosed herein may encompass an increase in expression of Ribosomal protein S6 kinase beta-1 (S6K1 also known as p70S6 kinase (p70S6K)) signaling pathway genes compared to a gene expression profile of a subject without HS. In some aspects, a gene expression profile of a subject with HS or suspected of having HS as disclosed herein may encompass an about 10% to about 20% increase in expression of p70S6K signaling pathway genes compared to a gene expression profile of a subject without HS. In other aspects, a gene expression profile of a subject with HS or suspected of having HS as disclosed herein may encompass an about 10% to about 20% increase in expression of p70S6K signaling pathway genes selected from the group of PLCB2, PPP2R2A, PIK3R1, PLCH2, SHC1, PLCD3, PIK3CG, PPM1L, IRS2, MAP2K1, EGFR, IL4R, PRKCQ, CD79B, GRB2, GNAI1, PIK3C2G, CD79A, TLR9, GNAI2, RPS6, BTK, RRAS2, MAPT, SYK, PLCG2, PPP2R2B, LYN, and PIK3CD compared to a gene expression profile of a subject without HS. In some aspects, a gene expression profile of a subject with HS or suspected of having HS as disclosed herein may encompass an about 10% to about 20% increase in expression of p70S6K signaling pathway genes and an about 5% to about 10% decrease in expression of p70S6K signaling pathway genes compared to a gene expression profile of a subject without HS.

In some embodiments, a gene expression profile of a subject with HS or suspected of having HS as disclosed herein may encompass an increase in expression of Inducible Costimulator (ICOS) and ICOS Ligand (ICOSL) signaling pathway genes compared to a gene expression profile of a subject without HS. In some aspects, a gene expression profile of a subject with HS or suspected of having HS as disclosed herein may encompass an about 10% to about 20% increase in expression of ICOS/ICOSL signaling pathway genes compared to a gene expression profile of a subject without HS. In other aspects, a gene expression profile of a subject with HS or suspected of having HS as disclosed herein may encompass an about 10% to about 20% increase in expression of ICOS/ICOSL signaling pathway genes selected from the group of CD247, PRKCQ, NFATC3, GRB2, ITPR2, CSK, CD4, PIK3R1, PIK3C2G, HLA-DQA1, TLR9, CD3D, PTPRC, SHC1, HLA-DMA, PIK3CG, ITPR3, HLA-DRA, ICOS, HLA-DMB, FCER1G, HLA-DOB, VAV1, IRS2, PIK3CD, PLEKHA1, and ITK compared to a gene expression profile of a subject without HS. In some aspects, a gene expression profile of a subject with HS or suspected of having HS as disclosed herein may encompass an about 10% to about 20% increase in expression of ICOS/ICOSL signaling pathway genes and an about 5% to about 10% decrease in expression of ICOS/ICOSL signaling pathway genes compared to a gene expression profile of a subject without HS.

In some embodiments, a gene expression profile of a subject with HS or suspected of having HS as disclosed herein may encompass an increase in expression of PKCθ signaling pathway genes in T cells compared to a gene expression profile of a subject without HS. In some aspects, a gene expression profile of a subject with HS or suspected of having HS as disclosed herein may encompass an about 10% to about 20% increase in expression of PKCθ signaling pathway genes in T cells compared to a gene expression profile of a subject without HS. In other aspects, a gene expression profile of a subject with HS or suspected of having HS as disclosed herein may encompass an about 10% to about 20% increase in expression of PKCθ signaling pathway genes in T cells selected from the group of CD247, MAP2K4, RAC2, NFATC3, PIK3R1, CD4, HLA-DQA1, MAP3K5, HLA-DMA, PIK3CG, HLA-DMB, HLA-DRA, MAP3K7, IRS2, PRKCQ, MAP3K6, GRB2, PIK3C2G, TLR9, CD3D, RRAS2, PLCG2, FCER1G, CD86, HLA-DOB, PIK3CD, VAV1, and MAP3K3 compared to a gene expression profile of a subject without HS. In some aspects, a gene expression profile of a subject with HS or suspected of having HS as disclosed herein may encompass an about 10% to about 20% increase in expression of PKCθ signaling pathway genes in T cells and an about 5% to about 10% decrease in expression of PKCθ signaling pathway genes in T cells compared to a gene expression profile of a subject without HS.

In some embodiments, a gene expression profile of a subject with HS or suspected of having HS as disclosed herein may encompass an increase in expression of bacterial and/or viral pattern recognition receptor genes compared to a gene expression profile of a subject without HS. In some aspects, a gene expression profile of a subject with HS or suspected of having HS as disclosed herein may encompass an about 10% to about 20% increase in expression of bacterial and/or viral pattern recognition receptor genes compared to a gene expression profile of a subject without HS. In other aspects, a gene expression profile of a subject with HS or suspected of having HS as disclosed herein may encompass an about 10% to about 20% increase in expression of bacterial and/or viral pattern recognition receptor genes selected from the group of MAP2K4, PIK3R1, TLR8, C1QC, C1QA, IL6, CCL5, C1QB, IFIH1, IL17D, PIK3CG, TLR7, CASP1, IRS2, CXCL8, OAS1, PRKCQ, OAS2, GRB2, MYD88, PIK3C2G, TLR9, IRF7, SYK, PLCG2, IL1B, and PIK3CD compared to a gene expression profile of a subject without HS. In some aspects, a gene expression profile of a subject with HS or suspected of having HS as disclosed herein may encompass an about 10% to about 20% increase in expression of bacterial and/or viral pattern recognition receptor genes and an about 2% to about 8% decrease in expression of bacterial and/or viral pattern recognition receptor genes compared to a gene expression profile of a subject without HS.

In some embodiments, a gene expression profile of a subject with HS or suspected of having HS as disclosed herein may encompass an increase in expression of acute phase response signaling pathway genes compared to a gene expression profile of a subject without HS. In some aspects, a gene expression profile of a subject with HS or suspected of having HS as disclosed herein may encompass an about 10% to about 20% increase in expression of acute phase response signaling pathway genes compared to a gene expression profile of a subject without HS. In other aspects, a gene expression profile of a subject with HS or suspected of having HS as disclosed herein may encompass an about 10% to about 20% increase in expression of acute phase response signaling pathway genes selected from the group of MAP2K4, SOCS3, PIK3R1, SOCS6, IL6, MAP3K5, IL1F10, NR3C1, C1R, SHC1, SOD2, PIK3CG, CFB, MAP3K7, SERPINA1, OSMR, SERPINE1, TNFRSF1B, MAP2K1, MYD88, GRB2, C1S, IL36A, VWF, STAT3, IL37, FTL, RRAS2, IL1B, PIK3CD, A2M, and C2 compared to a gene expression profile of a subject without HS. In some aspects, a gene expression profile of a subject with HS or suspected of having HS as disclosed herein may encompass an about 10% to about 20% increase in expression of acute phase response signaling pathway genes and an about 1% to about 6% decrease in expression of acute phase response signaling pathway genes compared to a gene expression profile of a subject without HS.

In some embodiments, a gene expression profile of a subject with HS or suspected of having HS as disclosed herein may encompass an increase in expression of GP6 (Glycoprotein VI (platelet)) signaling pathway genes compared to a gene expression profile of a subject without HS. In some aspects, a gene expression profile of a subject with HS or suspected of having HS as disclosed herein may encompass an about 10% to about 20% increase in expression of GP6 signaling pathway genes compared to a gene expression profile of a subject without HS. In other aspects, a gene expression profile of a subject with HS or suspected of having HS as disclosed herein may encompass an about 10% to about 20% increase in expression of GP6 signaling pathway genes selected from the group of COL4A5, PIK3R1, COL4A2, COL6A6, COL15A1, COL5A1, RHOG, PIK3CG, LAMB1, IRS2, COL5A2, PRKCQ, COL4A1, APBB 1IP, GRB2, PIK3C2G, LAMC3, TLR9, LAMC2, BTK, COL6A3, SYK, PLCG2, LYN, FCER1G, and PIK3CD compared to a gene expression profile of a subject without HS. In some aspects, a gene expression profile of a subject with HS or suspected of having HS as disclosed herein may encompass an about 10% to about 20% increase in expression of GP6 signaling pathway genes and an about 1% to about 8% decrease in expression of GP6 signaling pathway genes compared to a gene expression profile of a subject without HS.

In some embodiments, a gene expression profile of a subject with HS or suspected of having HS as disclosed herein may encompass an increase in expression of retinoic acid-mediated apoptosis signaling pathway genes compared to a gene expression profile of a subject without HS. In some aspects, a gene expression profile of a subject with HS or suspected of having HS as disclosed herein may encompass an about 10% to about 20% increase in expression of retinoic acid-mediated apoptosis signaling pathway genes compared to a gene expression profile of a subject without HS. In other aspects, a gene expression profile of a subject with HS or suspected of having HS as disclosed herein may encompass an about 10% to about 20% increase in expression of retinoic acid-mediated apoptosis signaling pathway genes selected from the group of CASP3, PARP10, PARP2, TNFRSF10B, ZC3HAV1, TNFSF10, PARP3, PARP9, IRF1, TIPARP, BID, RXRA, IFNAR1, and PARP14 compared to a gene expression profile of a subject without HS. In some aspects, a gene expression profile of a subject with HS or suspected of having HS as disclosed herein may encompass an about 10% to about 20% increase in expression of retinoic acid-mediated apoptosis signaling pathway genes and an about 1% to about 8% decrease in expression of retinoic acid-mediated apoptosis signaling pathway genes compared to a gene expression profile of a subject without HS.

In some embodiments, a gene expression profile of a subject with HS or suspected of having HS as disclosed herein may encompass an increase in expression of genes that contribute to the tumoricidal effects of hepatic natural killer (NK) cells compared to a gene expression profile of a subject without HS. In some aspects, a gene expression profile of a subject with HS or suspected of having HS as disclosed herein may encompass an about 15% to about 35% increase in expression of genes that contribute to the tumoricidal effects of hepatic NK cells compared to a gene expression profile of a subject without HS. In other aspects, a gene expression profile of a subject with HS or suspected of having HS as disclosed herein may encompass an about 15% to about 35% increase in expression of genes that contribute to the tumoricidal effects of hepatic NK cells selected from the group of M6PR, CASP3, GZMB, SRGN, BID, BAX, and AIFM1 compared to a gene expression profile of a subject without HS. In some aspects, a gene expression profile of a subject with HS or suspected of having HS as disclosed herein may encompass an about 15% to about 35% increase in expression of genes that contribute to the tumoricidal effects of hepatic NK cells and about less than 0.5% decrease in expression of genes that contribute to the tumoricidal effects of hepatic NK cells compared to a gene expression profile of a subject without HS. In some other aspects, a gene expression profile of a subject with HS or suspected of having HS as disclosed herein may encompass an about 15% to about 35% increase in expression of genes that contribute to the tumoricidal effects of hepatic NK cells and no decreased expression of genes that contribute to the tumoricidal effects of hepatic NK cells compared to a gene expression profile of a subject without HS.

In some embodiments, a gene expression profile of a subject with HS or suspected of having HS as disclosed herein may encompass an increase in expression of B-cell receptor signaling pathway genes compared to a gene expression profile of a subject without HS. In some aspects, a gene expression profile of a subject with HS or suspected of having HS as disclosed herein may encompass an about 10% to about 20% increase in expression of B-cell receptor signaling pathway genes compared to a gene expression profile of a subject without HS. In other aspects, a gene expression profile of a subject with HS or suspected of having HS as disclosed herein may encompass an about 10% to about 20% increase in expression of B-cell receptor signaling pathway genes selected from the group of MAP2K4, RAC2, NFATC3, PIK3R1, MAP3K5, OCRL, PTPRC, SHC1, PIK3CG, MAP3K7, IRS2, MAP2K1, ETS1, PTPN6, PRKCQ, APBB1IP, CFL1, MAP3K6, CD79B, GRB2, FCGR2A, CSK, PIK3C2G, CD79A, TLR9, BTK, BCL2L1, RRAS2, PLCG2, SYK, LYN, PIK3CD, VAV1, and MAP3K3 compared to a gene expression profile of a subject without HS. In some aspects, a gene expression profile of a subject with HS or suspected of having HS as disclosed herein may encompass an about 10% to about 20% increase in expression of B-cell receptor signaling pathway genes and an about 1% to about 6% decrease in expression of B-cell receptor signaling pathway genes compared to a gene expression profile of a subject without HS.

In some embodiments, a gene expression profile of a subject with HS or suspected of having HS as disclosed herein may encompass an increase in expression of peroxisome proliferator-activated receptor (PPAR) signaling pathway genes compared to a gene expression profile of a subject without HS. In some aspects, a gene expression profile of a subject with HS or suspected of having HS as disclosed herein may encompass an about 10% to about 20% increase in expression of PPAR signaling pathway genes compared to a gene expression profile of a subject without HS. In other aspects, a gene expression profile of a subject with HS or suspected of having HS as disclosed herein may encompass an about 10% to about 20% increase in expression of PPAR signaling pathway genes selected from the group of GRB2, IL1RL1, IL36A, NR1H3, IL1F10, IL37, PDGFC, IL18RAP, SHC1, HSP90B1, RRAS2, IL1RL2, MAP3K7, NCOA1, IL1B, RXRA, TNFRSF1B, MAP2K1, and PPARGC1A compared to a gene expression profile of a subject without HS. In some aspects, a gene expression profile of a subject with HS or suspected of having HS as disclosed herein may encompass an about 10% to about 20% increase in expression of PPAR signaling pathway genes and an about 1% to about 6% decrease in expression of PPAR signaling pathway genes compared to a gene expression profile of a subject without HS.

In some embodiments, a gene expression profile of a subject with HS or suspected of having HS as disclosed herein may encompass an increase in expression of calcium-induced T-cell apoptosis signaling pathway genes compared to a gene expression profile of a subject without HS. In some aspects, a gene expression profile of a subject with HS or suspected of having HS as disclosed herein may encompass an about 10% to about 20% increase in expression of calcium-induced T-cell apoptosis signaling pathway genes compared to a gene expression profile of a subject without HS. In other aspects, a gene expression profile of a subject with HS or suspected of having HS as disclosed herein may encompass an about 10% to about 20% increase in expression of calcium-induced T-cell apoptosis signaling pathway genes selected from the group of CD247, PRKCQ, ITPR2, CD4, HDAC1, HLA-DQA1, CD3D, HLA-DMA, HLA-DRA, ITPR3, HLA-DMB, FCER1G, HLA-DOB, and ORAI1 compared to a gene expression profile of a subject without HS. In some aspects, a gene expression profile of a subject with HS or suspected of having HS as disclosed herein may encompass an about 10% to about 20% increase in expression of calcium-induced T-cell apoptosis signaling pathway genes and an about 1% to about 7% decrease in expression of calcium-induced T-cell apoptosis signaling pathway genes compared to a gene expression profile of a subject without HS In some embodiments, a gene expression profile of a subject with HS or suspected of having HS as disclosed herein may encompass an increase in expression of SAPK/JNK (c-Jun N-terminal kinase (JNK) which is also referred to as stress-activated kinase (SAPK)) signaling pathway genes compared to a gene expression profile of a subject without HS. In some aspects, a gene expression profile of a subject with HS or suspected of having HS as disclosed herein may encompass an about 10% to about 20% increase in expression of SAPK/JNK signaling pathway genes compared to a gene expression profile of a subject without HS. In other aspects, a gene expression profile of a subject with HS or suspected of having HS as disclosed herein may encompass an about 10% to about 20% increase in expression of SAPK/JNK signaling pathway genes selected from the group of MAP2K4, MAP4K2, RAC2, GRB2, NFATC3, GNA12, PIK3R1, PIK3C2G, MAP3K5, TLR9, MAP4K3, SHC1, RRAS2, PIK3CG, MAP3K7, FCER1G, PIK3CD, IRS2, MAP4K1, and MAP3K3 compared to a gene expression profile of a subject without HS. In some aspects, a gene expression profile of a subject with HS or suspected of having HS as disclosed herein may encompass an about 10% to about 20% increase in expression of SAPK/JNK signaling pathway genes and an about 1% to about 7% decrease in expression of SAPK/JNK signaling pathway genes compared to a gene expression profile of a subject without HS.

In some embodiments, a gene expression profile of a subject with HS or suspected of having HS as disclosed herein may encompass an increase in expression of PI3K (Phosphoinositide 3-kinase) signaling pathway genes in B lymphocytes compared to a gene expression profile of a subject without HS. In some aspects, a gene expression profile of a subject with HS or suspected of having HS as disclosed herein may encompass an about 10% to about 18% increase in expression of PI3K signaling pathway genes in B lymphocytes compared to a gene expression profile of a subject without HS. In other aspects, a gene expression profile of a subject with HS or suspected of having HS as disclosed herein may encompass an about 10% to about 18% increase in expression of PI3K signaling pathway genes in B lymphocytes selected from the group of IL4R, PLCB2, CD79B, ATF5, NFATC3, ITPR2, PIK3R1, CD79A, ATF6, PLCH2, PTPRC, BTK, PLCD3, RRAS2, SYK, PIK3CG, PLCG2, ITPR3, LYN, PIK3CD, IRS2, VAV1, PLEKHA1, and MAP2K1 compared to a gene expression profile of a subject without HS. In some aspects, a gene expression profile of a subject with HS or suspected of having HS as disclosed herein may encompass an about 10% to about 18% increase in expression of PI3K signaling pathway genes in B lymphocytes and an about 1% to about 8% decrease in expression of PI3K signaling pathway genes in B lymphocytes compared to a gene expression profile of a subject without HS.

In some embodiments, a gene expression profile of a subject with HS or suspected of having HS as disclosed herein may encompass an increase in expression of telomerase signaling pathway genes compared to a gene expression profile of a subject without HS. In some aspects, a gene expression profile of a subject with HS or suspected of having HS as disclosed herein may encompass an about 10% to about 20% increase in expression of telomerase signaling pathway genes compared to a gene expression profile of a subject without HS. In other aspects, a gene expression profile of a subject with HS or suspected of having HS as disclosed herein may encompass an about 10% to about 20% increase in expression of telomerase signaling pathway genes selected from the group of ETS1, GRB2, PPP2R2A, PIK3R1, HDAC1, PIK3C2G, TLR9, SHC1, RB1, ELF4, HSP90B1, RRAS2, HDAC11, PIK3CG, PPP2R2B, PPM1L, IRS2, PIK3CD, MAP2K1, ELKS, and EGFR compared to a gene expression profile of a subject without HS. In some aspects, a gene expression profile of a subject with HS or suspected of having HS as disclosed herein may encompass an about 10% to about 20% increase in expression of telomerase signaling pathway genes and an about 1% to about 10% decrease in expression of telomerase signaling pathway genes compared to a gene expression profile of a subject without HS.

In some embodiments, a gene expression profile of a subject with HS or suspected of having HS as disclosed herein may encompass one or more genes up regulated by at least one upstream transcriptional regulator with a higher likelihood of activation in a subject with HS or suspected of having HS compared to a subject without HS. In some aspects, an upstream regulator with a higher likelihood of activation in a subject with HS or suspected of having HS compared to a subject without HS can be interferon alpha, interferon gamma (IFNG), lipopolysaccharide, tumor necrosis factor (TNF), oncostatin M (OSM), or a combination thereof. In other aspects, activation of an upstream regulator may have one or more downstream effects depending on the targeted downstream molecule.

In some aspects, a gene expression profile of a subject with HS or suspected of having HS with a higher likelihood of interferon gamma activation compared to a subject without HS may encompass changes in at least one targeted downstream molecule expression. In other aspects, a downstream molecule targeted by interferon gamma activation in a subject with HS or suspected of having HS may be A2M, ABCA6, ABCD3, ACTB, ADA2, ADM, ADORA2B, AIF1, AIF1L, AIM2, ALDH1A3, ALKAL2, ALPL, ANGPTL4, APOBEC3G, APOL1, APP, ARAP2, AUTS2, AZGP1, BAX, BBC3, BCAN, BCL2, BCL2L1, BCL2L2, BCL3, BID, BIRC2, BMF, BST2, BTN3A1, BTN3A2, C1QA, C1QB, C1QC, C1R, C2, CALCOCO2, CALHM6, CASP1, CASP3, CASP4, CAT, CCL2, CCL3L3, CCL5, CCL8, CCNA2, CCND1, CCND2, CCNO, CCR2, CCRL2, CD14, CD163, CD163L1, CD2, CD36, CD38, CD4, CD55, CD68, CD72, CD74, CD86, CDH13, CEBPA, CERS6, CFB, CGAS, CH25H, CHI3L2, CIRBP, CLEC2D, CLIC4, COL5A2, CORO1A, CRLF1, CSK, CTSB, CTSC, CTSZ, CXCL10, CXCL12, CXCL8, CXCL9, CXCR4, CYB5A, CYBA, CYBB, CYLD, CYP11A1, CYP2E1, DEGS1, DLG4, E2F5, EDNRA, EFNB2, EGR3, ENO1, ERBB2, FCER1G, FCGR1A, FCGR1B, FCGR2A, FCGR3A/FCGR3B, FCN1, FTL, FZD2, GAD1, GART, GATA3, GBP1, GBP2, GBP4, GBP5, GCHFR, GLA, GLDN, GNAI2, GSDMD, GZMB, HIF1A, HLA-DMA, HLA-DMB, HLA-DOB, HLA-DQA1, HLA-DRA, HLA-E, IDO1, IFI16, IFI27, IFI30, IFI35, IFI44, IFI6, IFIH1, IFIT2, IFIT3, IFITM1, IFITM2, IFITM3, IGFBP4, IL10RA, IL17D, IL18BP, IL18RAP, IL19, IL1B, IL1RL1, IL22RA1, IL23A, IL32, IL4R, IL6, IL7, IL7R, IRF1, IRF4, IRF7, IRF8, IRF9, IRS2, ISG20, ITGA4, ITGAX, ITGB2, KLF10, KLF4, KLF6, KYNU, LAMC2, LAT2, LGALS3, LGALS3BP, LGALS9, LTB, LY96, LYN, MAP2K1, MARCKSL1, MERTK, MFSD2A, MITF, MMP3, MMP9, MNDA, MST1R, MT1F, MTMR3, MUC1, MX1, MYD88, MYH9, NAMPT, NDRG4, NTF4, NTRK2, NUPR1, OAS1, OAS2, OPTN, P2RY14, PARP9, PARVG, PCDH17, PCTP, PECAM1, PIM2, PLA2G7, PLAU, PLAUR, PLEK, PPARGC1A, PPIA, PPP1R1B, PRDM1, PRKCQ, PSMB10, PSMB8, PSMB9, PSME1, PSME2, PTHLH, PTPN6, RAB27A, RAC2, RARRES3, RB1, RFX5, RORC, S100A7, S100A8, S100A9, SBNO2, SELE, SELL, SELP, SEMA4A, SEPT3, SEPT4, SERPINA1, SERPINE1, SERPINH1, SLAMF1, SLC12A2, SLC15A3, SLC16A3, SLC1A3, SLC29A1, SLC6A1, SLC7A5, SOCS3, SOD2, SP100, SP110, STAT1, STAT2, STAT3, STAT4, SYNM, TAC1, TAP2, TAPBP, TAPBPL, TBC1D10A, TBXAS1, TCIRG1, TGFBR3, THY1, TIMP1, TLR7, TLR8, TLR9, TMEM50B, TNFAIP6, TNFRSF10B, TNFRSF14, TNFRSF1B, TNFRSF9, TNFSF10, TNFSF13B, TPI1, TRIB2, TYMP, TYROBP, UBD, UBE2L6, VCAM1, VIPR1, WARS, WNT5A, ZNF638, ZYX, or a combination thereof.

In some aspects, a gene expression profile of a subject with HS or suspected of having HS with a higher likelihood of lipopolysaccharide activation compared to a subject without HS may encompass changes in at least one targeted downstream molecule expression. In other aspects, a downstream molecule targeted by lipopolysaccharide activation in a subject with HS or suspected of having HS may be ABCC1, ABCC5, ABCF2, ACP5, ACTN4, ACVR2A, ADA, ADM, ADORA2B, AK4, ALCAM, ALDH2, ALOX12, ALOX5, ANGPT2, ANGPTL4, APLNR, APOBEC3F, APOBEC3G, APP, ARHGAP1, ARHGEF3, ARPC1B, AZGP1, BATF, BAX, BCL2, BCL2L1, BCL3, BID, BIRC2, BMP2, BMP4, BTK, CALR, CASP1, CASP3, CASP4, CCL2, CCL21, CCL3L3, CCL5, CCL8, CCNB2, CCND1, CCND2, CCR2, CCR7, CCRL2, CD14, CD163, CD163L1, CD36, CD37, CD38, CD4, CD48, CD53, CD55, CD69, CD74, CD86, CD8A, CD9, CDC42EP4, CDH11, CEBPA, CEMIP, CFB, CFD, CGAS, CH25H, CLDN1, CLIC4, COL4A1, COL4A2, COL5A1, COL5A2, CORO1A, CRTAP, CRYAB, CSF2RA, CSF3R, CTH, CTSB, CTSC, CTSL, CUX2, CXCL10, CXCL12, CXCL13, CXCL14, CXCL8, CXCL9, CXCR4, CYB5A, CYBA, CYBB, CYP2E1, CYTIP, DAG1, DHCR24, DLG4, DNAJB11, DNMT1, DRAM1, EFNB2, EGR3, ELANE, ELKS, ENO1, ENPP2, EPHX2, ERCC1, ERP44, ETV3, FCER1G, FES, FLI1, FLOT2, FPR1, FSCN1, GBP1, GBP2, GBP4, GBP5, GCA, GCHFR, GEM, GEMIN4, GLRB, GMFG, GNPAT, GNRH1, GPR183, GSN, GUCY1A3, GZMA, GZMB, GZMH, HESS, HIF1A, HIVEP1, HLA-DMA, HLA-DOB, HLA-DQA1, HMGCS2, HSP90B1, HYOU1, ICAM2, IDO1, IFI16, IFI27, IFI35, IFI44, IFI6, IFIH1, IFIT2, IFIT3, IFITM1, IFITM2, IGFBP4, IGSF6, IL10RA, IL10RB, IL13RA1, IL18RAP, IL19, IL1B, IL23A, IL24, IL32, IL36A, IL4R, IL6, IL7, IL7R, IRF1, IRF4, IRF7, IRF8, IRF9, ISG20, ITGA4, ITGAX, ITGB2, JCHAIN, KANK1, KCNJ15, KCNK5, KIAA1551, KLF10, KLF4, KLF6, KYNU, LAMB1, LASP1, LGALS3, LGALS3BP, LGALS9, LIPA, LIPG, LPIN2, LRBA, LY96, LYN, LYZ, M6PR, MAPT, MARCKS, MARCKSL1, MCL1, MCM5, MCTS1, mir-154, mir-21, MME, MMP23B, MMP3, MMP9, MSC, MSN, MST1R, MT2A, MX1, MYD88, MYH14, MYH9, NAMPT, NCF1, NCOA1, NFIX, NNMT, NOCT, NPTX1, NR1H3, NR3C1, NSFL1C, NUPR1, OAS1, OAS2, ORAI1, OSMR, OXCT1, PCOLCE2, PDE4B, PDIA4, PECAM1, PI3, PIK3CG, PIK3R1, PIM2, PLA2G7, PLAT, PLAU, PLAUR, PLEK, PLEKHA1, PLSCR1, PNPLA1, POU2AF1, PPARGC1A, PPIA, PPP1CB, PPP1R16B, PRDM1, PSMB10, PSMB8, PSMB9, PSME1, PSME2, PTHLH, PTPN7, PTPRCAP, RAB3B, RALGDS, RARRES3, RB1, RCAN1, RFC1, RGS1, RNASE2, RXRA, S100A12, S100A8, S100A9, S1PR1, SAMSN1, SAP18, SAT1, SELE, SELL, SELP, SEPT4, SERPINA1, SERPINB1, SERPINB2, SERPINE1, SERPINH1, SERPINI1, SIGIRR, SLAMF1, SLAMF7, SLC15A3, SLC16A3, SLC1A5, SLC29A1, SLC39A8, SLC3A2, SNX5, SOCS3, SOD2, ST6GAL1, STAP1, STAT1, STAT2, STAT3, STAT4, STIM1, STX4, TAC1, TACC3, TAPBP, TDO2, TGM2, THY1, TIMP1, TIPARP, TLR7, TLR8, TLR9, TMSB10/TMSB4X, TNC, TNFAIP6, TNFRSF1B, TNFRSF4, TNFRSF9, TNFSF10, TNFSF13B, TNIP1, TNNC1, TNNT2, TOLLIP, TPI1, TYMP, TYROBP, UCP2, VAV1, VCAM1, VNN3, VWF, WARS, WEE1, XAF1, XBP1, ZC3H12A, ZNF281, ZYX, or a combination thereof.

In some aspects, a gene expression profile of a subject with HS or suspected of having HS with a higher likelihood of TNF activation compared to a subject without HS may encompass changes in at least one targeted downstream molecule expression. In other aspects, a downstream molecule targeted by TNF activation in a subject with HS or suspected of having HS may be A2M, AATK, ABCC1, ABTB2, ACP5, ACTB, ADGRG6, ADM, ADORA2B, AKAP12, ALCAM, ALDH1A3, ALDH2, ALOX5, ANGPT2, ANGPTL4, ANK3, APBA3, APOL1, APP, ARF4, ARHGAP23, ARHGDIB, ATP2B4, AXIN2, B4GALT1, BAX, BBC3, BBOX1, BCL2, BCL2L1, BCL2L13, BCL2L2, BCL3, BID, BIRC2, BLVRA, BMP2, BMP4, BMPR1A, BST2, BTBD3, BTN3A3, C1QTNF1, CALR, CARD16, CASP1, CASP3, CASP4, CAT, CCDC15, CCL2, CCL27, CCL3L3, CCL5, CCND1, CCND2, CCR2, CCR7, CD14, CD163, CD163L1, CD247, CD36, CD38, CD4, CD5, CD55, CD69, CD86, CDC42EP4, CDH11, CDH13, CEBPA, CEBPG, CERS6, CFB, CFD, CH25H, CHI3L2, CLDN11, CLIC4, COL15A1, CRISPLD2, CRLF1, CRY1, CRYAB, CST7, CTDSPL, CTLA4, CTSB, CTSC, CTSZ, CXCL10, CXCL12, CXCL13, CXCL8, CXCL9, CXCR4, CYBA, CYBB, CYLD, CYP11A1, CYP26B1, CYP2E1, CYTH3, CYTIP, DAG1, DCD, DENND4A, DMD, DNMT1, DUSP6, DVL1, EDAR, EFHD2, EFNA1, EFNB2, EGFR, EGR3, ELKS, ENG, ENPP2, ERBB2, ERCC1, ETS1, EXOSC7, FAM198B, FCER1G, FMO1, FPR1, FRMD6, FSCN1, GBP1, GBP2, GEM, GNAI1, GNAI2, GOSR2, GPX1, GRN, HCN3, HDAC1, HIF1A, HIPK2, HIVEP1, HLA-DRA, HLA-E, HSD11B1, ICAM2, ICOS, IDH2, IDO1, IFI16, IFI27, IFI6, IFIH1, IFIT3, IFITM1, IFNAR2, IGFBP4, IGFBP6, IL10RA, IL17D, IL18BP, IL19, IL1B, IL1F10, IL1RL1, IL1RL2, IL23A, IL24, IL32, IL36A, IL37, IL4R, IL6, IL7, IL7R, IRF1, IRF4, IRF7, IRF8, IRS2, ITGA4, ITGAX, ITGB2, ITPR2, JAG2, KLF10, KLF4, KLF6, KLK3, KLRB1, KRT23, KYNU, L3MBTL3, LAMC2, LFNG, LGALS3, LGALS8, LGALS9, LSS, LTB, LY96, LYN, MAGI1, MAP2K4, MAP3K7, MARCKSL1, MCL1, MECOM, MEOX1, MFSD2A, mir-21, MMP28, MMP3, MMP9, MPC1, MSC, MST1, MST1R, MSX2, MT2A, MUC1, MVP, MX1, MYD88, MYH9, MYL6, NAMPT, NCF1, NCK1, NCOA1, NFE2L2, NNMT, NOCT, NPM3, NR1H3, NR3C1, NRARP, NRROS, OAS1, OAS2, OLFML2B, OPTN, OSMR, PAK2, PARP14, PCP4, PDE4B, PDIA4, PDK3, PDPN, PDZD2, PECAM1, PI3, PIK3CD, PIK3CG, PIM2, PLA2G4A, PLAT, PLAU, PLAUR, PLP1, PLSCR1, PLVAP, PNPLA1, POU2AF1, PPARGC1A, PRDM1, PSMB10, PSMB8, PSMB9, PSME1, PSME2, PTHLH, PTPRC, RARRES2, RARRES3, RB1, RCAN1, RFTN1, RFX2, RFX5, RGS1, RNASE2, RNASE4, RRM2, RXRA, S100A7, S100A8, S100A9, SAT1, SCO2, SEC22B, SELE, SELL, SELP, SERPINB1, SERPINB2, SERPINB8, SERPINE1, SGK1, SLC1A3, SLC27A5, SLC43A2, SLCO2B1, SMPDL3A, SNCG, SNRK, SOCS3, SOD2, SORBS1, ST3GAL6, ST6GAL1, ST8SIA4, STAT1, STAT4, SYVN1, TAC1, TAPBP, TBC1D8, TBXAS1, TCFL5, TFAP2A, TGM2, THY1, TIMP1, TLR7, TLR8, TMEM176B, TMEM40, TNC, TNFAIP6, TNFRSF10B, TNFRSF18, TNFRSF1B, TNFRSF21, TNFRSF4, TNFRSF6B, TNFRSF9, TNFSF10, TNFSF13B, TNIP1, TNNC1, TP53I3, TP53INP1, TYK2, TYMP, UBD, UCP2, VASH1, VCAM1, VIPR1, VMP1, WLS, WNT3A, WNT5A, ZC3H12A, ZYX, or a combination thereof.

In some aspects, a gene expression profile of a subject with HS or suspected of having HS with a higher likelihood of oncostatin M activation compared to a subject without HS may encompass changes in at least one targeted downstream molecule expression. In other aspects, a downstream molecule targeted by oncostatin M activation in a subject with HS or suspected of having HS may be A2M, ABCC1, ABCC5, ACSL5, ADGRG6, AKR1C3, ANGPT2, ARHGEF12, ARHGEF2, ARL4A, ATP2B4, BAIAP2, BBOX1, BCL2, BTC, C1R, C1S, CADM4, CASP4, CAT, CCL2, CCL5, CCND1, CCND2, CDC42EP4, CEBPA, CH25H, CHI3L2, CLIP1, CRLF1, CRY1, CST6, CTSL, CXCL10, CXCL12, CXCL13, CXCL8, DEGS1, DHCR24, DNAJC3, DNM1L, EPCAM, EPHB6, ERBB3, EXOSC10, FOXN3, GART, GAS7, GBP1, GBP2, GCA, GFPT1, GNS, GPNMB, HIF1A, HSD11B1, HSPA2, HSPB3, IFI35, IGFBP6, IL13RA1, IL1B, IL32, IL4R, IL6, IL7, IRF1, IRF7, IRF9, ISG20, KLF10, KLK1, KRT2, LCE2B, LY6G6C, MAP2, MARCKS, MGLL, MMP3, MMP9, MOAP1, MPDU1, MSC, MT2A, MX1, MYD88, NAMPT, NMT2, OAS1, OSMR, P2RY10, PAK2, PDPN, PGGT1B, PI3, PKIG, PLA2G4A, PLAU, PLLP, PRDM1, PRR4, PSMB8, PSMB9, PTP4A1, PTPN21, PTPRZ1, PYGL, RAB31, RAB4A, RNASE4, RORA, RUNX1, S100A12, S100A7, S100A8, S100A9, SEL1L, SELE, SELP, SEPT9, SERPINA1, SERPINB1, SERPINB8, SERPINE1, SLC16A3, SMAD5, SOCS3, SON, STAT1, STAT3, TAP2, TAPBP, TDO2, TIMP1, TNC, TNNC1, TYMP, TYRO3, UBE2L6, USP46, USP9X, VCAM1, WNT5A, ZC3HAV1, or a combination thereof.

II. Administration of Treatment

In general, methods disclosed herein include treating a subject having or suspected of having HS by assessing the subject's gene and/or protein expression profile, diagnosing the subject with HS and/or detecting the level of HS severity, and administering the appropriate treatment for the level of HS severity. In some other embodiments, treatment after gene and/or protein expression profiling a subject having or suspected of having HS as disclosed herein may prevent HS progression. In other embodiments, treatment after gene and/or protein expression profiling a subject having or suspected of having HS as disclosed herein may ameliorate one or more symptoms of a dermatological pathology associated with HS in a subject. In still other embodiments, treatment after gene and/or protein expression profiling a subject having or suspected of having HS as disclosed herein may reduce risk of recurrence in a subject diagnosed with HS following a surgical procedure. In some embodiments, treatment after gene and/or protein expression profiling a subject having or suspected of having HS as disclosed herein may be administration of one or more home remedies, one or more pharmaceutical compositions, one or more radiological therapies, one or more surgical procedures, or a combination thereof.

In some embodiments, treatment after gene and/or protein expression profiling a subject having or suspected of having HS as disclosed herein may be administration of one or more home remedies. Non-limiting examples of home remedies suitable for treatment after gene and/or protein expression profiling a subject having or suspected of having HS as disclosed herein include warm baths, applying warm compresses to the affected area for at least about 5 to about 15 minutes, applying at least one topical cleansing agent to the affected area, administering at least one over the counter (OTC) anti-inflammatory medication, wearing loose fitting clothing, maintaining a Body Mass Index (BMI) under about 27, under about 26, under about 25 ($kg/m^2$). As used herein, BMI is a measure of body fat based on height and weight that applies to adult men and women wherein a BMI under 18.5 $kg/m^2$ is classified as underweight, between 18.5 $kg/m^2$ to 24.9 $kg/m^2$ is classified as normal weight, between 25 $kg/m^2$ to 29.9 $kg/m^2$ is classified as overweight, and over 30 $kg/m^2$ is classified as obese. Non-limiting examples of topical cleansing agents suitable for application to the affected area of a subject disclosed herein include any antibacterial soaps, antiseptics, and acne washes known to reduce and/or kill bacteria. Non-limiting examples of OTC anti-inflammatory medications suitable for administration to a subject disclosed herein include ibuprofen, naproxen, celecoxib, and the like.

In some embodiments, administration of one or more home remedies may be administered to treat mild HS after gene and/or protein expression profiling a subject having or suspected of having HS as disclosed herein. In some aspects, administration of one or more home remedies may be administered to treat mild HS after determination that a gene expression profile of a subject with HS or suspected of having HS as disclosed herein encompasses decreased expression of dermcidin, Mammaglobin A, or a combination thereof, increased expression of S100A8, S100A9, or a combination thereof, and no change in gene expression of IL-37, CCL27 or a combination thereof compared to a gene expression profile of a subject without HS. In some other aspects, administration of one or more home remedies may be administered to treat mild HS after determination that a gene expression profile of a subject with HS or suspected of having HS as disclosed herein encompasses at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS.

In some embodiments, administration of one or more home remedies may prevent mild HS progression into moderate or severe HS after determination that a gene expression profile of a subject with HS or suspected of having HS as disclosed herein encompasses decreased expression of dermcidin, Mammaglobin A, or a combination thereof, increased expression of S100A8, S100A9, or a combination thereof, and no change in gene expression of IL-37, CCL27 or a combination thereof compared to a gene expression profile of a subject without HS. In some aspects, administration of one or more home remedies may prevent mild HS progression into moderate or severe HS after determination that a gene expression profile of a subject with HS or suspected of having HS as disclosed herein encompasses at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS.

In some embodiments, administration of one or more home remedies may ameliorate one or more symptoms of a dermatological pathology associated with mild HS after determination that a gene expression profile of a subject with HS or suspected of having HS as disclosed herein encompasses decreased expression of dermcidin, Mammaglobin A, or a combination thereof, increased expression of S100A8, S100A9, or a combination thereof, and no change in gene expression of IL-37, CCL27 or a combination thereof compared to a gene expression profile of a subject without HS. In some aspects, administration of one or more home remedies may ameliorate one or more symptoms of a dermatological pathology associated with mild HS after determination that a gene expression profile of a subject with HS or suspected of having HS as disclosed herein encompasses at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS.

In some embodiments, administration of one or more home remedies may decrease activity of mild HS after determination that a gene expression profile of a subject with HS or suspected of having HS as disclosed herein encompasses decreased expression of dermcidin, Mammaglobin A, or a combination thereof, increased expression of S100A8, S100A9, or a combination thereof, and no change in gene expression of IL-37, CCL27 or a combination thereof compared to a gene expression profile of a subject without HS. In some aspects, administration of one or more home remedies may decrease activity of mild HS after determination that a gene expression profile of a subject with HS or suspected of as disclosed herein encompasses at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS. In other aspects, administration of one or more home remedies may decrease a HSS score that is less than about 20 after determination that a gene expression profile of a subject with HS or suspected of having HS as disclosed herein encompasses decreased expression of dermcidin, Mammaglobin A, or a combination thereof, increased expression of S100A8, S100A9, or a combination thereof, and no change in gene expression of IL-37, CCL27 or a combination thereof compared to a gene expression profile of a subject without HS. In some other aspects, administration of one or more home remedies may decrease a HSS score that is less than about 20 by about 1% to about 75%, about 5% to about 50%, or about 10% to about 25% after determination that a gene expression profile of a subject with HS or suspected of having HS as disclosed herein encompasses decreased expression of dermcidin, Mammaglobin A, or a combination thereof, increased expression of S100A8, S100A9, or a combination thereof, and no change in gene expression of IL-37, CCL27 or a combination thereof compared to a gene expression profile of a subject without HS. In yet other aspects, administration of one or more home remedies may decrease a HSS score that is less than about 20 after determination that a gene expression profile of a subject with HS or suspected of having HS as disclosed herein encompasses at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS. In still other aspects, administration of one or more home remedies may decrease a HSS score that is less than about 20 by about 1% to about 75%, about 5% to about 50%, or about 10% to about 25% after determination that a gene expression profile of a subject with HS or suspected of having HS as disclosed herein encompasses at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS.

In other aspects, administration of one or more home remedies may decrease abscess and inflammatory nodule count (AN count) after determination that a gene expression profile of a subject with HS or suspected of having HS as disclosed herein encompasses decreased expression of dermcidin, Mammaglobin A, or a combination thereof, increased expression of S100A8, S100A9, or a combination thereof, and no change in gene expression of IL-37, CCL27 or a combination thereof compared to a gene expression profile of a subject without HS. In still other aspects, administration of one or more home remedies may decrease AN count by about 1% to about 75%, about 5% to about 50%, or about 10% to about 25% after determination that a gene expression profile of a subject with HS or suspected of having HS as disclosed herein encompasses decreased expression of dermcidin, Mammaglobin A, or a combination thereof, increased expression of S100A8, S100A9, or a combination thereof, and no change in gene expression of IL-37, CCL27 or a combination thereof compared to a gene expression profile of a subject without HS. In yet other aspects, administration of one or more home remedies may decrease AN count after determination that a gene expression profile of a subject with HS or suspected of having HS as disclosed herein encompasses at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS. In still other aspects, administration of one or more home remedies may decrease AN count by about 1% to about 75%, about 5% to about 50%, or about 10% to about 25% after determination that a gene expression profile of a subject with HS or suspected of having HS as disclosed herein encompasses at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS.

In other embodiments, administration of one or more home remedies may decrease Dermatology Quality of Life Index (DQLI) score after determination that a gene expression profile of a subject with HS or suspected of having HS as disclosed herein encompasses decreased expression of dermcidin, Mammaglobin A, or a combination thereof, increased expression of S100A8, S100A9, or a combination thereof, and no change in gene expression of IL-37, CCL27 or a combination thereof compared to a gene expression profile of a subject without HS. Table 2 is an example of a DQLI questionnaire provided to a subjects with the instructions to score each response from 0 (absence) to 3 (intense problem).

TABLE 2

Example of a DQLI questionnaire

| Question | Score |
|---|---|
| 1. How itchy, sore, painful or stinging has your skin condition been? | |
| 2. How embarrassed or self-conscious have you been because of your skin? | |
| 3. How much has your skin interfered with you going shopping or looking after your home or garden? | |
| 4. How much has your skin influenced the clothes you wear? | |
| 5. How much has your skin affected your social or leisure activities? | |
| 6. How much has your skin made it difficult for you to do any sport? | |
| 7. Has your skin prevented you from working or studying? | |
| 8. How much has your skin created problems with your partner or any of your close friends or relatives? | |
| 9. How much has your skin caused any sexual difficulties? | |
| 10. How much of a problem has the treatment for your skin been? | |

In still other aspects, administration of one or more home remedies may decrease a DQLI score by about 1% to about 75%, about 5% to about 50%, or about 10% to about 25% after determination that a gene expression profile of a subject with HS or suspected of having HS as disclosed herein encompasses decreased expression of dermcidin, Mammaglobin A, or a combination thereof, increased expression of S100A8, S100A9, or a combination thereof, and no change in gene expression of IL-37, CCL27 or a combination thereof compared to a gene expression profile of a subject without HS. In yet other aspects, administration of one or more home remedies may decrease a DQLI score after determination that a gene expression profile of a subject with HS or suspected of having HS as disclosed herein encompasses at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS. In still other aspects, administration of one or more home remedies may a DQLI score by about 1% to about 75%, about 5% to about 50%, or about 10% to about 25% after determination that a gene expression profile of a subject with HS or suspected of having HS as disclosed herein encompasses at least about 1.5-fold to about 6-fold decrease in expression of dermcidin, Mammaglobin A, or a combination thereof, at least about 1.5-fold to about 6-fold increase in expression of S100A8, S100A9, or a combination thereof, and no change in gene expression of IL-37, CCL27 or a combination thereof compared to a gene expression profile of a subject without HS.

In some embodiments, treatment after gene and/or protein expression profiling a subject having or suspected of having HS as disclosed herein may be administration of one or more pharmaceutical compositions, one or more radiological therapies, one or more surgical procedures, or a combination thereof. In some aspects, a pharmaceutical composition suitable for use disclosed herein may be an antibiotic, a retinoid, a steroid hormone, an anti-inflammatory, or a combination thereof. Non-limiting examples of antibiotics suitable for use disclosed herein include amoxicillin, azithromycin, chloramphenicol, cephalexin, ciprofloxacin, clindamycin, erythromycin, metronidazole, trimethoprim-sulfamethoxazole, fluconazole, itraconazole, voriconazole, doxycycline, minocycline, levofloxacin, moxifloxacin, and linezolid. In some aspects, an antibiotic suitable for use as disclosed herein may be classified as a penicillin, a cephalosporin, a macrolide, a fluoroquinolone, a sulfonamide, a tetracycline, or an aminoglycoside. In some other aspects, administration of a retinoid suitable for use as disclosed herein may be oral, topical, or a combination thereof. In still other aspects, a steroid hormone suitable for use as disclosed herein may be corticosteroid, spironolactone, or the like. In some aspects, an anti-inflammatory suitable for use as disclosed herein may be a biologic, a small molecule, or a combination thereof. As used herein, the term "biologic" refers to a pharmaceutical composition produced from living organisms or contain components of living organisms. Non-limiting examples of biologics include recombinant proteins, tissues, genes, allergens, cells, blood components, blood, and vaccines. In some aspects, a biologic used as an anti-inflammatory suitable for use as disclosed herein may be a monoclonal antibody, a recombinant protein, or a combination thereof.

In some embodiments, administration of at least one antibiotic, at least one retinoid, at least one steroid hormone, at least one anti-inflammatory, or a combination thereof may be administered to treat moderate to severe HS after gene and/or protein expression profiling a subject having or suspected of having HS as disclosed herein. In some aspects, administration of at least one antibiotic, at least one retinoid, at least one steroid hormone, at least one anti-inflammatory, or a combination thereof may be administered to treat moderate to severe HS after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In some embodiments, administration of a surgical procedure may be administered to treat moderate to severe HS after gene and/or protein expression profiling a subject having or suspected of having HS as disclosed herein. In some aspects, administration of a surgical procedure may be administered to treat moderate to severe HS after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In some embodiments, administration of at least one antibiotic, at least one retinoid, at least one steroid hormone, at least one anti-inflammatory, or a combination thereof after a surgical procedure may prevent symptom reoccurrence in moderate to severe HS after gene and/or protein expression profiling a subject having or suspected of having HS as disclosed herein. In some aspects, administration of at least one antibiotic, at least one retinoid, at least one steroid hormone, at least one anti-inflammatory, or a combination thereof after a surgical procedure may prevent symptom reoccurrence in moderate to severe HS after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In some embodiments, administration of radiation therapy may be administered to treat moderate to severe HS after gene and/or protein expression profiling a subject having or suspected of having HS as disclosed herein. In some aspects, administration of radiation therapy may be administered to treat moderate to severe HS after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In some embodiments, administration of at least one antibiotic, at least one retinoid, at least one steroid hormone, at least one anti-inflammatory, at least one surgical procedure, radiation therapy or a combination thereof may be administered to prevent progression of moderate HS to severe HS after gene and/or protein expression profiling a subject having or suspected of having HS as disclosed herein. In some aspects, administration of at least one antibiotic, at least one retinoid, at least one steroid hormone, at least one anti-inflammatory, at least one surgical procedure, radiation therapy or a combination thereof may be administered to prevent progression of moderate HS to severe HS after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In some embodiments, administration of at least one antibiotic, at least one retinoid, at least one steroid hormone, at least one anti-inflammatory, at least one surgical procedure, radiation therapy or a combination thereof may ameliorate one or more symptoms of a dermatological pathology associated with moderate to severe HS after determination that a gene expression profile of a subject with HS or suspected of having HS as disclosed herein encompasses increased in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and a decrease in expression of dermcidin, IL-37, or a combination thereof compared to a gene expression profile of a subject without HS. In some aspects, administration of at least one antibiotic, at least one retinoid, at least one steroid hormone, at least one anti-inflammatory, at least one surgical procedure, radiation therapy or a combination thereof may ameliorate one or more symptoms of a dermatological pathology associated with moderate to severe HS after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In some embodiments, administration of at least one antibiotic, at least one retinoid, at least one steroid hormone, at least one anti-inflammatory, at least one surgical procedure, radiation therapy or a combination thereof may decrease activity of moderate to severe HS after determination that a gene expression profile of a subject with HS or suspected of having HS as disclosed herein encompasses increased expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about decreased expression of dermcidin, IL-37, or a combination thereof compared to a gene expression profile of a subject without HS. In some aspects, administration of at least one antibiotic, at least one retinoid, at least one steroid hormone, at least one anti-inflammatory, at least one surgical procedure, radiation therapy or a combination thereof may decrease activity of moderate to severe HS after determination that a gene expression profile of a subject with HS or suspected of as disclosed herein encompasses at least about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In other aspects, administration of at least one antibiotic, at least one retinoid, at least one steroid hormone, at least one anti-inflammatory, at least one surgical procedure, radiation therapy or a combination thereof may decrease a HSS score that is more than about 20 after determination that a gene expression profile of a subject with HS or suspected of having HS as disclosed herein encompasses increased expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and decreased expression of dermcidin, IL-37, or a combination thereof compared to a gene expression profile of a subject without HS. In some other aspects, administration of at least one antibiotic, at least one retinoid, at least one steroid hormone, at least one anti-inflammatory, at least one surgical procedure, radiation therapy or a combination thereof may decrease a HSS score that is more than about 20 after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In some other aspects, at least one antibiotic, at least one retinoid, at least one steroid hormone, at least one anti-inflammatory, at least one surgical procedure, radiation therapy or a combination thereof may decrease a HSS score that is more than about 20 by about 1% to about 75%, about 5% to about 50%, or about 10% to about 25% after determination that a gene expression profile of a subject with HS or suspected of having HS as disclosed herein encompasses increased expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and decreased expression of dermcidin, IL-37, or a combination thereof compared to a gene expression profile of a subject without HS. In still some other aspects, at least one antibiotic, at least one retinoid, at least one steroid hormone, at least one anti-inflammatory, at least one surgical procedure, radiation therapy or a combination thereof may decrease a HSS score that is more than about 20 by about 1% to about 75%, about 5% to about 50%, or about 10% to about 25% after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In some aspects, administration of at least one antibiotic, at least one retinoid, at least one steroid hormone, at least one anti-inflammatory, at least one surgical procedure, radiation therapy or a combination thereof may decrease abscess and inflammatory nodule count (AN count) after determination that a gene expression profile of a subject with HS or suspected of having HS as disclosed herein encompasses increased expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and decreased expression of dermcidin, IL-37, or a combination thereof compared to a gene expression profile of a subject without HS. In other aspects, administration of at least one antibiotic, at least one retinoid, at least one steroid hormone, at least one anti-inflammatory, at least one surgical procedure, radiation therapy or a combination thereof may decrease abscess and inflammatory nodule count (AN count) after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In yet other aspects, administration of at least one antibiotic, at least one retinoid, at least one steroid hormone, at least one anti-inflammatory, at least one surgical procedure, radiation therapy or a combination thereof may decrease AN count by about 1% to about 75%, about 5% to about 50%, or about 10% to about 25% after determination that a gene expression profile of a subject with HS or suspected of having HS as disclosed herein encompasses increased expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and decreased expression of dermcidin, IL-37, or a combination thereof compared to a gene expression profile of a subject without HS. In still other aspects, administration of at least one antibiotic, at least one retinoid, at least one steroid hormone, at least one anti-inflammatory, at least one surgical procedure, radiation therapy or a combination thereof may decrease AN count by about 1% to about 75%, about 5% to about 50%, or about 10% to about 25% after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In some aspects, administration of at least one antibiotic, at least one retinoid, at least one steroid hormone, at least one anti-inflammatory, at least one surgical procedure, radiation therapy or a combination there may decrease Dermatology Quality of Life Index (DQLI) score after determination that a gene expression profile of a subject with HS or suspected of having HS as disclosed herein encompasses increased expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and decreased expression of dermcidin, IL-37, or a combination thereof compared to a gene expression profile of a subject without HS. In other aspects, administration of at least one antibiotic, at least one retinoid, at least one steroid hormone, at least one anti-inflammatory, at least one surgical procedure, radiation therapy or a combination there may decrease DQLI score after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In yet other aspects, administration of at least one antibiotic, at least one retinoid, at least one steroid hormone, at least one anti-inflammatory, at least one surgical procedure, radiation therapy or a combination thereof may decrease a DQLI score by about 1% to about 75%, about 5% to about 50%, or about 10% to about 25% after determination that a gene expression profile of a subject with HS or suspected of having HS as disclosed herein encompasses increased expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and decreased expression of dermcidin, IL-37, or a combination thereof compared to a gene expression profile of a subject without HS. In still other aspects, administration of at least one antibiotic, at least one retinoid, at least one steroid hormone, at least one anti-inflammatory, at least one surgical procedure, radiation therapy or a combination thereof may decrease a DQLI score by about 1% to about 75%, about 5% to about 50%, or about 10% to about 25% after determination that a gene expression profile of a subject with HS or suspected of having HS as disclosed herein encompasses about a 1.5-fold to about a 15-fold, about a 2-fold to about a 14 fold, or about a 3-fold to about a 13-fold increase in expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and about a 1.5-fold to about 6-fold, about a 2-fold to about a 5-fold, or about a 2.5-fold to about a 4-fold decrease in expression of dermcidin, IL-37, or a combination thereof compared to a gene expression profile of a subject without HS.

In some embodiments, a radiation therapy suitable for use as disclosed herein may be delivered externally, internally, or a combination thereof. In some aspects, external radiation therapy may be localized by directing high-energy X-rays at the affected region. In other aspects, internal radiation therapy (also referred to as brachytherapy) may be localized by placing radioactive sources, such as radioactive seeds, inside the body near the affected region. In some other aspects, radiation therapy may be skin-directed radiotherapy. As used herein, the term "skin-directed radiotherapy" refers to localized administration of external radiation to the skin. In still other aspects, skin-directed radiotherapy may be administered at least once a day for about a week, for about 2 weeks, or about 3 weeks. In other aspects, skin-directed radiotherapy may be administered at least once a day every other day for about a week, for about 2 weeks, or about 3 weeks. In some other aspects, skin-directed radiotherapy may be administered in at least 2 fractions, at least 3 fractions, at least 4 fractions, at least 5 fractions, at least 6 fractions, or at least 7 fractions. In some aspects, fractions can be administered consecutively. In other aspects, fractions can be administered every 48 hours. In still other aspects, total prescription dose of radiation therapy may be about 0.5 gray (gy) to about 10 gy, about 1 gy to about 8 gy, or about 2 gy to about 6 gy. In some aspects, total prescription dose of radiation therapy may be about 0.5 gy, about 1 gy, about 2 gy, about 3 gy, about 4 gy, about 5 gy, about 6 gy, about 7 gy, about 8 gy, about 9 gy, or about 10 gy. In some other aspects, total prescription dose of radiation therapy may be about 2.5 gy, about 3.5 gy, about 4.5 gy, about 5.5 gy, about 6.5 gy, or about 7.5 gy. In some aspects, total prescription dose of radiation therapy may be administered in equal fractions of about 1 gy to about 5 gy or about 2 gy to about 4 gy. In other aspects, total prescription dose of radiation therapy may be administered in equal fractions of about 1 gy, about 1.5 gy, about 2 gy, about 2.5 gy, or about 3 gy.

In some embodiments, a surgical procedure suitable for use as disclosed herein may be cryoinsufflation, incision and drainage, deroofing, skin tissue—saving excision with electrosurgical peeling, wide surgical excision, skin closure, or a combination thereof. In some aspects, a closure method suitable for use as disclosed herein may be healing by secondary intention, primary (suture-based) closure, skin grafts, skin flaps, or a combination thereof. In other aspects, a skin flap suitable for used as disclosed herein may be a fasciacutaneous flap, parascapular fasciacutaneous flap, local transposition flap, or a combination thereof. A surgical procedure suitable for use as disclosed herein may be used on an affected region about 5 cm² to about 2000 cm², about 10 cm² to about 1800 cm², or about 15 cm² to about 1600 cm².

In some embodiments, an anti-inflammatory suitable for use as disclosed herein may be a tumor necrosis factor inhibitor, an interleukin-1 inhibitor, a Janus kinase (JAK) inhibitor, an interleukin-17 inhibitor, an IL-23 inhibitor, a Complement component 5a (C5a) inhibitor, or a combination thereof. In some aspects, a tumor necrosis factor inhibitor suitable for use as disclosed herein may be etanercept, infliximab, adalimumab, or a combination thereof. In some preferred aspects, a tumor necrosis factor inhibitor suitable for use as disclosed herein may be etanercept, adalimumab, or a combination thereof.

In some aspects, an interleukin-1 (IL1) inhibitor suitable for use as disclosed herein may be an interleukin-1 receptor antagonist, an interleukin-1 antagonist, or a combination thereof. In some other aspects, an interleukin-1 inhibitor suitable for use as disclosed herein may be a broad interleukin-1 inhibitor, a specific interleukin-1 alpha inhibitor, a specific interleukin-1 beta inhibitor, or a combination thereof. In still other aspects, an interleukin-1 inhibitor suitable for use as disclosed herein may be anakinra, bermekimab, canakinumab, rilonacept, or a combination thereof. In some preferred aspects, an interleukin-1 inhibitor suitable for use as disclosed herein may be anakinra, bermekimab, or a combination thereof.

In some aspects, a JAK inhibitor suitable for use as disclosed herein may be a broad JAK inhibitor, a specific JAK 1 inhibitor, a specific JAK2 inhibitor, a specific JAK3 inhibitor, or a combination thereof. In some other aspects, a JAK inhibitor suitable for use as disclosed herein may be Tofacitinib, Ruxolitinib (INCB18424), Baricitinib (INCB28050), INCB54707, Peficitinib (ASP015K), Decernotinib (VX-509), Filgotinib (GLPG0634), Solcitinib, Itacitinib (INCB039110), Momelotinib (CYT387), Upadacitinib (ABT-494), Abrocitinib (PF-04965842), AC-430, R348, R723, BMS911543, AZD1480, CEP33779, or a combination thereof. In some preferred aspects, a JAK inhibitor suitable for use as disclosed herein may be INCB54707.

In some aspects, an interleukin-17 (IL17) inhibitor suitable for use as disclosed herein may be an interleukin-17 receptor antagonist, an interleukin-17 antagonist, or a combination thereof. In some other aspects, an interleukin-17 inhibitor suitable for use as disclosed herein may be a broad interleukin-17 inhibitor, a specific interleukin-17RA inhibitor, a specific interleukin-17RB inhibitor, or a combination thereof. In some other aspects, an interleukin-17 inhibitor suitable for use as disclosed herein may be secukinumab, brodalumab, ixekizumab, bimekizumab, CJM112, or a combination thereof. In some preferred aspects, in interleukin-17 inhibitor suitable for use as disclosed herein may be secukinumab, brodalumab, or a combination thereof.

In some aspects, an interleukin-23 (IL23) inhibitor suitable for use as disclosed herein may be an interleukin-23 receptor antagonist, an interleukin-23 antagonist, an inhibitor of the interleukin-23 shared IL-12/23p40 subunit, or a combination thereof. In some other aspects, an interleukin-23 inhibitor suitable for use as disclosed herein may be ustekinumab, risankizumab, guselkumab, tildrakizumab, briakinumab, or a combination thereof. In some preferred aspects, an interleukin-23 inhibitor suitable for use as disclosed herein may be risankizumab, guselkumab, or a combination thereof.

In some aspects, a complement component 5a (C5a) inhibitor suitable for use as disclosed herein may be an C5a inhibitory peptide, a monoclonal antibody, a small molecule, or a combination thereof. In some aspects, a C5a inhibitor suitable for use as disclosed herein may be eculizumab, CCX168, PMX53, MP-435, or a combination thereof. In some preferred aspects, a C5a inhibitor suitable for use as disclosed herein may be eculizumab, CCX168, or a combination thereof.

In various embodiments, the dose of a pharmaceutical compositions disclosed herein to be administered is not particularly limited, and may be appropriately chosen depending on conditions such as a purpose of preventive and/or therapeutic treatment, a type of a disease, the body weight or age of a subject, severity of a disease and the like. In other embodiments, administration of a dose of a pharmaceutical composition disclosed herein may comprise an effective amount of the composition disclosed herein. As used herein, the term "effective amount" refers to an amount of administered composition that treats a subject with HS or suspected of having HS as disclosed herein that has a gene expression profile encompassing increased expression of S100A7, S100A8, S100A9, STAT1, NFATC3, BTK, CXCR4, CD86, CD247, CD3D, HLA-DMA, HLS-DMB, IL6, IL4R, CD79A, or a combination thereof compared to a gene expression profile of a subject without HS and decreased expression of dermcidin, IL-37, or a combination thereof compared to a gene expression profile of a subject without HS.

In some aspects, a pharmaceutical composition suited for use as disclosed herein can be a biologic. In some other aspects, a biologic suited for use as disclosed herein may be etanercept, infliximab, adalimumab, anakinra, bermekimab, canakinumab, rilonacept, secukinumab, brodalumab, ixekizumab, bimekizumab, CJM112, ustekinumab, risankizumab, guselkumab, tildrakizumab, briakinumab, eculizumab, or a combiantion thereof. In some instances, the biologic as disclosed herein can be administered to a subject at a dose of about 1 mg/kg to about 3 mg/kg, about 3 mg/kg to about 4 mg/kg, about 4 mg/kg to about 8 mg/kg, about 8 mg/kg to about 12 mg/kg, about 12 mg/kg to about 16 mg/kg, about 16 mg/kg to about 20 mg/kg, about 20 mg/kg to about 24 mg/kg, about 24 mg/kg to about 28 mg/kg, or about 28 mg/kg to about 32 mg/kg (e.g., about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, about 30 mg/kg, about 31 mg/kg, or about 32 mg/kg) once every two to four weeks (e.g., every two, three, or four weeks). In one embodiment, a biologic as disclosed herein is administered every 2 weeks. In one embodiment, a biologic as disclosed herein is administered every 2 weeks intravenously, e.g., for 3 months. In some instances, biologic as disclosed herein can be administered to a subject at a dose of 1 mg/kg to 3 mg/kg, 3 mg/kg to 4 mg/kg, 4 mg/kg to 8 mg/kg, 8 mg/kg to 12 mg/kg, 12 mg/kg to 16 mg/kg, 16 mg/kg to 20 mg/kg, 20 mg/kg to 24 mg/kg, 24 mg/kg to 28 mg/kg, or 28 mg/kg to 32 mg/kg (e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, or 32 mg/kg) once every two to four weeks (e.g., every two, three, or four weeks).

In some aspects, a pharmaceutical composition suited for use as disclosed herein can be a small molecule. In some aspects, a pharmaceutical composition suited for use as disclosed herein can be in an oral dosage form. In other aspects, a small molecule may be an antibiotic, Tofacitinib, Ruxolitinib (INCB18424), Baricitinib (INCB28050), INCB54707, Peficitinib (ASP015K), Decernotinib (VX-509), Filgotinib (GLPG0634), Solcitinib, Itacitinib (INCB039110), Momelotinib (CYT387), Upadacitinib (ABT-494), Abrocitinib (PF-04965842), AC-430, R348, R723, BMS911543, AZD1480, CEP33779, or a combination thereof. In some aspects, a small molecule suited for use as disclosed herein can be can be administered to a subject at a dose of about 0.5 mg to about 1500 mg, about 1 mg to about 1000 mg, about 2 mg to about 750 mg, about 3 mg to about 500 mg, about 4 mg to about 250 mg, or about 5 mg to about 100 mg once a day, twice a day, or three times a day. In some other aspects, a small molecule suited for use as disclosed herein can be can be administered to a subject at a dose of about 0.5 mg, about 1 mg, about 2 mg, about 3 mg, about 4 mg, about 5 mg, about 10 mg, about 25 mg, about 50 mg, about 100 mg, about 250 mg, about 500 mg, or about 1000 mg once a day, twice a day, or three times a day. In some aspects, a JAK inhibitor suited for use as disclosed herein can be can be administered to a subject at a dose of about 1 mg to about 250 mg, about 2 mg to about 200 mg, about 3 mg to about 150 mg, about 4 mg to about 100 mg, about 5 mg to about 50 mg, or about 10 mag to about 20 mg once a day, twice a day, or three times a day.

The present disclosure may further encompass a kit, wherein the kit includes at least one component that can be used in a method of determining a gene expression profile and/or protein expression profile of a subject with HS or suspected of having HS as disclosed herein. In various embodiments, a kit may further include at least one pharmaceutical composition suitable for treating moderate to severe HS as disclosed herein. In other embodiments, a kit may include at least one component that can be used in a bead array technology for determining a gene expression profile and/or protein expression profile of a subject with HS or suspected of having HS as disclosed herein bead array technology.

EXAMPLES

The following examples are included to demonstrate preferred embodiments of the disclosure. It should be appreciated by those of skill in the art that the techniques disclosed in the examples that follow represent techniques discovered by the inventors to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Example 1

Participant Selection, Specimen Collection, and Specimen Processing. Hidradenitis suppurativa (HS) (n=10) were enrolled in the Wound Etiology and Healing (WE-HEAL) Study, a biospecimen and data repository designed for studying HS and chronic wounds. Demographic data, baseline medical comorbidities (including diabetes, autoimmune disease, cardiovascular and renal disease and smoking exposure) and laboratory data were abstracted from the electronic health record and stored using REDCap. (Harris P A et al., *J Biomed Inform* 2009; 42: 377-81, the disclosures of which are incorporated herein). Clinical data, including disease activity scores (Hurley stage, active nodule count, modified Hidradenitis Sartorius Score), surgical interventions and medication exposures were collected at each visit. A rheumatologist, who was fully trained in HS outcome measures and had over 8 years of experience managing subjects with HS, performed the clinical scoring of HS lesions for this study. Specimens of normal human skin (n=11) were collected from abdominoplasty procedures for use in the healthy control (HC) group. Demographic characteristics were not available for the HCs, but they were all healthy individuals undergoing elective abdominoplasty. They had no history of skin disease and no underlying malignancy.

Specimens were collected from HS subjects by debridement (n=10) and abdominoplasty (n=11). Demographic characteristics and disease activity scores of the HS subjects are provided below in Table 3.

TABLE 3

Demographic characteristics and disease activity scores for the subjects with hidradenitis suppurativa.

| Parameter | Subjects (n = 10) |
|---|---|
| Age, years | 35.33 ± 10.82 |
| Female sex, n (%) | 4 (40) |
| African American, n (%) | 6 (60) |
| Body mass index, kg/m$^2$ | 37.08 ± 8.72 |
| Never-smokers, n (%) | 8 (80) |
| Hurley stage III, n (%) | 7 (70) |
| Hidradenitis Sartorius Score (HSS) | 63 ± 37.27 |
| Visual Analogue Scale (VAS) pain score | 5.55 ± 2.79 |

Of the HS specimens, seven were collected from groin and pubic lesions and three were from HS in other locations. To minimize differences in cellular and molecular components related to anatomical sampling location, 12 mm punch biopsy samples were taken from the en bloc specimens, ensuring that the biopsies were taken from active HS lesions within the HS specimens and from areas including hair follicles from the HC specimens.

Immediately after removal, all specimens were transported to the laboratory for processing. Punch biopsy samples were immersed in RNA-later solution (QIAGEN, Hilden, Germany) at room temperature for 4 hours, transferred to 4° C. for 24-48 hours and subsequently cryopreserved at −80° C. Total RNA was extracted using a commercial kit (RNeasy Fibrous Tissue Kit; QIAGEN). After extraction, RNA integrity was assessed using an automated analyzer (Bioanalyzer 2100; Agilent Technologies, Santa Clara, Calif., USA) and samples with an RNA integrity number of ≥7 were used for analysis. RNA (1 μg) was amplified, labeled with biotin, purified and then hybridized to microarray chips (Human HT-12 v4 Expression BeadChips; Illumina Inc. San Diego, Calif., USA). (Fan J et al., *Biotechniques* 2005; 39: 583-8, the disclosures of which are incorporated herein). BeadChips were scanned (HiScanSQ system; Illumina Inc.) and fluorescence emission by cyanine C3 was quantitatively detected for analysis.

Example 2

Microarray Data Analysis Identifies Differentially Expressed Genes in Control and HS Specimens. Raw Bead-Chip data were analyzed using the limma package (Ritchie M E et al. Nucleic Acids Res 2015; 43: e47, the disclosures of which are incorporated herein) and beadarray package (Dunning M J et al., *Bioinformatics* 2007; 23: 2183-4, the disclosures of which are incorporated herein). Raw signal intensity data were background-corrected using negative control probes followed by quantile normalization. (Phipson B et al., *Ann Appl Stat* 2016; 10: 946-63, the disclosures of which are incorporated herein).

Probes were filtered using two criteria: the quality grade assigned to the probe by Illumina and the detection probabilities calculated by comparing the summarized intensity with negative control probes. Probes with 'Perfect' or 'Good' quality grades that exceeded a detection probability threshold of <0.05 in at least three samples were used in the analysis; all other probes were discarded. Principal component analysis of the normalized data was used to identify batch effects, and adjustment for batch effects was performed using the ComBat method in the SVA package. (Johnson W E et al., *Biostatistics* 2007; 8: 118-27, the disclosures of which are incorporated herein). Microarray data from this study have been deposited in National Center for Biotechnology Information (NCBI)'s Gene Expression Omnibus, accessible through Gene Expression Omnibus (GEO) accession number GSE128637.

Differentially expressed genes were detected by fitting genewise linear models to the normalized expression data (limma) at a false discovery rate (FDR) of <0.05 and an absolute log two-fold change≥abs(log FC)≥1.00 (equivalent to two-fold changes). The FDR and fold change cut-offs were selected based on our desired tolerance for false positives. As the genes identified as differentially expressed are further modelled using a web-based software (Ingenuity Pathway Analysis (IPA); QIAGEN, Redwood City, Calif., USA), which takes into account the FDR and fold change, we chose more relaxed cut-offs for these values to maximize sensitivity. Differentially expressed genes were modelled using IPA, and the upstream regulator analysis of IPA was performed to identify upstream regulators and their status (activated or inhibited), based on observed gene expression changes in the dataset. (Kramer A et al., *Bioinformatics* 2014; 30: 523-30, the disclosures of which are incorporated herein).

In the comparison of HS with HC skin, 436 genes were overexpressed and 363 genes were underexpressed in subjects with HS compared with the healthy control (HC) group (FDR<0.05, abs(log FC)≥1.00). The top 25 differentially expressed genes are listed in Table 4.

TABLE 4

Top differentially expressed genes

| Genes with an average decrease in expression across all HS specimens compared across all HC specimens | Genes with an average increase in expression across all HS specimens compared across all HC specimens |
|---|---|
| DCD (dermcidin) | ILMN_1652199 |
| SCGB2A2 (secretoglobin family 2A member 2) | ILMN_1739508 |
| KRT2 (keratin 2) | MZB1 (Marginal Zone B And B1 Cell Specific Protein) |
| LCE2B (Late Cornified Envelope 2B) | FAM46C (family with sequence similarity 46, member C) |
| KRT77 (keratin 77) | ILMN_1680274 |
| LCE5A (Late Cornified Envelope 5A) | ILMN_1674228 |
| IL37 (inerlukein-37) | IGLL3P (immunoglobulin lambda like polypeptide 3, pseudogene) |
| C5orf46 (Chromosome 5 Open Reading Frame 46) | ILMN_1804601 |
| SERPINA12 (Serpin Family A Member 12) | IGKV1ORY-1 (Immunoglobulin Kappa Variable 1/ORY-1 (Pseudogene)) |
| CCL27 (C-C Motif Chemokine Ligand 27) | PI3 (elafin) |
| | S100A7 (S100 calcium binding protein A7) |
| | IGLL1 (immunoglobulin lambda like polypeptide 1) |
| | S100A9 (S100 calcium binding protein A9) |
| | S100A8 (S100 calcium binding protein A8) |

The gene with the greatest fold change in the HS samples compared with control samples was dermcidin (DCD), an antimicrobial peptide normally found in human sweat. This molecule was significantly downregulated in the HS specimens compared with HC specimens (expression log ratio −3.93, expression P=0.04) (FIG. 1). Additionally, IL-37, a cytokine that is a natural suppressor of innate immune responses, was also found to be one of the top 25 differentially expressed genes (FIG. 1). IL-37 was significantly downregulated in the HS compared with the HC specimens (expression log ratio −3.29, expression P<0.001).

Unsupervised two-dimensional hierarchical clustering was performed on the top 25 differentially expressed genes (FIG. 1). Data show two subject subgroups among the HS subject samples (FIG. 1).

Example 3

Ingenuity pathway analysis of HS and control samples for differential expression of canonical pathways. Canonical pathway analysis was performed using the microarray dataset obtained in Example 2, to identify biological functions and pathways associated with HS. Those with P<0.05 (Fisher exact test) were considered to be statistically significant. The IPA observed differences in gene expression between the HS and normal skin samples. The Z score was used as a statistical measure of the match between the expected relationship direction and the observed gene expression. A Z score of >2 or <−2 was considered significant.

Significant differential expression was seen in 30 canonical pathways in the HS samples compared with normal skin based on a −log(P) cut-off of 1.3 and a Z score activation prediction cut-off of >2 or <−2 (Table 5). The top five pathways were selected for additional study.

TABLE 5

Top 30 canonical pathways in which the HS microarray dataset significantly differed from normal control skin. Data were based on a −log(P-value) cut-off of 1.3 and a Z score activation prediction are of >2 or <−2. Data are ranked by −log(P-value).

| | Ingenuity canonical pathways | −log (P) | Ratio | Z score | Down-regulated | No change | Up-regulated | No overlap | Molecules |
|---|---|---|---|---|---|---|---|---|---|
| 1 | Interferon signaling | 7.87 | 0.528 | 4.24 | 2/36 (6%) | 0/36 (0%) | 17/36 (47%) | 17/36 (47%) | IFIT3, OAS1, MX1, PIAS1, TYK2, IFI35, IRF9, PSMB8, BAX, IFNAR2, IFITM2, IRF1, BCL2, IFITM3, STAT2, IFI6, STAT1, IFITM1, IFNAR1 |
| 2 | Leucocyte extravasation signaling | 7.4 | 0.27 | 2.10 | 19/211 (9%) | 0/211 (0%) | 38/211 (18%) | 154/211 (73%) | MAP2K4, RAC2, MYL6, MMP3, PIK3R1, WASL, CXCL12, PIK3CG, EZR, CYBA, CYBB, ARHGAP12, IRS2, ITGA4, ITK, PRKCQ, THY1, NCF4, TLR9, MMP27, NCF1, CLDN23, MMP23B, CLDN8, RAP1GAP, ICAM3, PLCG2, PECAM1, VAV1, PIK3CD, CLDN14, ACTN4, ARHGAP1, CLDN11, CTNNA1, RAPGEF4, TIMP1, SIPA1, ACTN1, VCAM1, MMP28, CXCR4, GRB2, ACTB, ARHGAP4, GNAI1, PIK3C2G, BTK, GNAI2, ITGB2, WIPF1, ARHGAP9, WAS, CLDN1, MMP9, CTNND1, MSN |
| 3 | Th1 pathway | 6.07 | 0.289 | 3.77 | 6/135 (4%) | 0/135 (0%) | 33/135 (24%) | 96/135 (71%) | CD247, SOCS3, NFATC3, PIK3R1, CD4, HLA-DQA1, NCSTN, LGALS9, IL6, CD8A, HLA-DQB2, HLA-DMA, PIK3CG, HLA-DRA, HLA-DMB, IRS2, STAT1, HLA-DPB1, PRKCQ, GRB2, TYK2, PIK3C2G, STAT3, TLR9, CD3D, IRF1, STAT4, ITGB2, ICOS, IL10RB, IL10RA, HLA-DOB, APH1B, CD86, VAV1, PIK3CD, GATA3, mir-21, IFNAR1 |

TABLE 5-continued

Top 30 canonical pathways in which the HS microarray dataset significantly differed from normal control skin. Data were based on a −log(P-value) cut-off of 1.3 and a Z score activation prediction are of >2 or <−2. Data are ranked by −log(P-value).

| | Ingenuity canonical pathways | −log (P) | Ratio | Z score | Down-regulated | No change | Up-regulated | No overlap | Molecules |
|---|---|---|---|---|---|---|---|---|---|
| 4 | Th2 pathway | 4.86 | 0.26 | 2.65 | 9/150 (6%) | 0/150 (0%) | 30/150 (20%) | 111/150 (74%) | CD247, SOCS3, TNFRSF4, IL1RL1, TGFBR3, PIK3R1, CD4, HLA-DQA1, NCSTN, HLA-DQB2, HLA-DMA, PIK3CG, HLA-DRA, HLA-DMB, IRS2, HLA-DPB1, IL4R, JAG2, PRKCQ, CXCR4, GRB2, TYK2, PIK3C2G, TLR9, IL24, CD3D, ACVR1B, STAT4, ITGB2, ICOS, S1PR1, HLA-DOB, APH1B, CD86, VAV1, PIK3CD, GATA3, mir-21, ACVR2A |
| 5 | Role of NFAT in regulation of the immune response | 4.29 | 0.237 | 3.68 | 11/186 (6%) | 0/186 (0%) | 33/186 (18%) | 142/186 (76%) | CD247, PLCB2, NFATC3, PIK3R1, CD4, GNA11, HLA-DQA1, FCER1A, FCGR1A, HLA-DMA, PIK3CG, HLA-DRA, HLA-DMB, IRS2, MAP2K1, FCGR3A/FCGR3B, GNG12, FCGR1B, ORAI1, ITK, PRKCQ, CD79B, FCGR2A, ITPR2, GRB2, GNA12, PIK3C2G, GNAI1, CSNK1D, CD79A, TLR9, CD3D, BTK, GNAI2, RCAN1, RRAS2, PLCG2, SYK, ITPR3, LYN, FCER1G, HLA-DOB, CD86, PIK3CD |
| 6 | Tec kinase signaling | 4.24 | 0.241 | 2.20 | 14/170 (8%) | 0/170 (0%) | 27/170 (16%) | 129/170 (76%) | MAP2K4, PIK3R1, GNA11, FCER1A, TNFSF10, RHOG, RHOT1, PIK3CG, IRS2, STAT1, GNG12, FGR, ITGA4, ITK, RND2, TNFRSF21, PAK4, PRKCQ, PAK6, GRB2, GNA12, ACTB, TYK2, TNFRSF10B, GNAI1, PIK3C2G, STAT3, TLR9, BTK, GNAI2, |

TABLE 5-continued

Top 30 canonical pathways in which the HS microarray dataset significantly differed from normal control skin. Data were based on a −log(P-value) cut-off of 1.3 and a Z score activation prediction are of >2 or <−2. Data are ranked by −log(P-value).

| | Ingenuity canonical pathways | −log (P) | Ratio | Z score | Down-regulated | No change | Up-regulated | No overlap | Molecules |
|---|---|---|---|---|---|---|---|---|---|
| 7 | Dendritic cell maturation | 3.59 | 0.223 | 3.48 | 10/193 (5%) | 0/193 (0%) | 33/193 (17%) | 150/193 (78%) | STAT4, RHOV, WAS, PLCG2, TNFRSF25, PAK2, LYN, FCER1G, VAV1, STAT2, PIK3CD, MAP2K4, PLCB2, LEPR, IL32, PIK3R1, HLA-DQA1, LTB, IL1F10, IL6, PLCH2, FCGR1A, PLCD3, IL1RL2, HLA-DMA, PIK3CG, HLA-DRA, HLA-DMB, IRS2, TNFRSF1B, IL23A, STAT1, FCGR3A/FCGR3B, FCGR1B, FCGR2A, MYD88, TYROBP, GRB2, PIK3C2G, IL36A, IL37, TLR9, STAT4, PLCG2, FSCN1, FCER1G, HLA-DOB, IL1B, CD86, STAT2, PIK3CD, IRF8, CCR7, IFNAR1 |
| 8 | Neuro-inflammation signaling pathway | 3.19 | 0.196 | 3.71 | 19/311 (6%) | 0/311 (0%) | 42/311 (14%) | 250/311 (80%) | MAP2K4, MMP3, NFATC3, TGFBR3, PIK3R1, TLR8, CXCL12, NCSTN, IL6, CXCL10, SOD2, PIK3CG, CYBB, IRS2, CXCL8, CASP3, TYK2, TLR9, ACVR1B, IRF7, PLCG2, SYK, KCNJ5, GAD1, MAPT, SLC6A1, APH1B, CD86, PIK3CD, KLK1, SNCA, KLK3, HLA-DQA1, SLC1A3, CCL5, BCL2, GABRB3, CCL2, HLA-DMA, GABRA6, HLA-DRA, IL34, HLA-DMB, CASP1, TLR7, STAT1, NFE2L2, VCAM1, TYROBP, MYD88, GRB2, PIK3C2G, GABRE, APP, GABRP, PLA2G4A, HLA-DOB, IL1B, MMP9, ACVR2A, BIRC2 |

TABLE 5-continued

Top 30 canonical pathways in which the HS microarray dataset significantly differed from normal control skin. Data were based on a −log(P-value) cut-off of 1.3 and a Z score activation prediction are of >2 or <−2. Data are ranked by −log(P-value).

| | Ingenuity canonical pathways | −log (P) | Ratio | Z score | Down-regulated | No change | Up-regulated | No overlap | Molecules |
|---|---|---|---|---|---|---|---|---|---|
| 9 | JAK/STAT signaling | 3.13 | 0.265 | 2.13 | 5/83 (6%) | 0/83 (0%) | 17/83 (20%) | 61/83 (73%) | SOCS3, PTPN6, GRB2, PIK3R1, SOCS6, PIAS1, TYK2, PIK3C2G, STAT3, IL6, TLR9, STAT4, SHC1, BCL2L1, PIAS3, RRAS2, PIK3CG, PIK3CD, IRS2, STAT2, STAT1, MAP2K1 |
| 10 | Oncostatin M signaling | 3.1 | 0.353 | 3.32 | 0/34 (0%) | 0/34 (0%) | 12/34 (35%) | 22/34 (65%) | MT2A, SHC1, EPAS1, RRAS2, MMP3, GRB2, TYK2, OSMR, PLAU, STAT3, STAT1, MAP2K1 |
| 11 | FcγRIIB signaling in B lymphocytes | 3.08 | 0.302 | 2.00 | 4/53 (8%) | 0/53 (0%) | 12/53 (23%) | 37/53 (70%) | MAP2K4, CD79B, GRB2, PIK3R1, PIK3C2G, CD79A, TLR9, BTK, SHC1, RRAS2, PIK3CG, PLCG2, SYK, LYN, IRS2, PIK3CD |
| 12 | IL-6 signaling | 3.06 | 0.234 | 2.04 | 8/128 (6%) | 0/128 (0%) | 22/128 (17%) | 98/128 (77%) | MAP2K4, HSPB3, SOCS3, IL1RL1, PIK3R1, IL1F10, IL6, SHC1, IL1RL2, PIK3CG, MAP3K7, IRS2, MAPKAPK2, TNFRSF1B, MAP2K1, MCL1, CXCL8, TNFAIP6, GRB2, IL36A, PIK3C2G, IL37, STAT3, TLR9, IL18RAP, RRAS2, IL1B, CD14, PIK3CD, A2M |
| 13 | Production of NO and ROS in macrophages | 2.96 | 0.211 | 3.48 | 16/194 (8%) | 0/194 (0%) | 25/194 (13%) | 153/194 (79%) | MAP2K4, PPP2R2A, PIK3R1, PPP1CB, MAP3K5, PPP1R14B, LYS, RHOG, RHOT1, CYBA, PIK3CG, PPM1L, CYBB, MAP3K7, SERPINA1, S100A8, IRS2, STAT1, TNFRSF1B, MAP2K1, RND2, PPP1R14C, PTPN6, PRKCQ, MAP3K6, GRB2, TYK2, PIK3C2G, NCF4, TLR9, IRF1, APOL1, RHOV, NCF1, PLCG2, PPP2R2B, CAT, PIK3CD, IRF8, MAP3K3, APOD |

TABLE 5-continued

Top 30 canonical pathways in which the HS microarray dataset significantly differed
from normal control skin. Data were based on a −log(P-value) cut-off of 1.3 and
a Z score activation prediction are of >2 or <−2. Data are ranked by −log(P-value).

| | Ingenuity canonical pathways | −log (P) | Ratio | Z score | Down-regulated | No change | Up-regulated | No overlap | Molecules |
|---|---|---|---|---|---|---|---|---|---|
| 14 | TREM1 signaling | 2.54 | 0.253 | 3.44 | 1/75 (1%) | 0/75 (0%) | 18/75 (24%) | 56/75 (75%) | SIGIRR, CXCL8, GRB2, TYROBP, IL1RL1, MYD88, LAT2, TLR8, STAT3, IL6, TLR9, NLRP9, CCL2, PLCG2, TLR7, CASP1, CD86, IL1B, ITGAX |
| 15 | p70S6K signaling | 2.52 | 0.22 | 2.04 | 12/132 (9%) | 0/132 (0%) | 17/132 (13%) | 103/132 (78%) | PLCB2, PPP2R2A, PIK3R1, PLCH2, SHC1, PLCD3, PIK3CG, PPM1L, IRS2, MAP2K1, EGFR, IL4R, PRKCQ, CD79B, GRB2, GNAI1, PIK3C2G, CD79A, TLR9, GNAI2, RPS6, BTK, RRAS2, MAPT, SYK, PLCG2, PPP2R2B, LYN, PIK3CD |
| 16 | iCOS/iCOSL signaling in Th cells | 2.38 | 0.22 | 2.40 | 7/123 (6%) | 0/123 (0%) | 20/123 (16%) | 96/123 (78%) | CD247, PRKCQ, NFATC3, GRB2, ITPR2, CSK, CD4, PIK3R1, PIK3C2G, HLA-DQA1, TLR9, CD3D, PTPRC, SHC1, HLA-DMA, PIK3CG, ITPR3, HLA-DRA, ICOS, HLA-DMB, FCER1G, HLA-DOB, VAV1, IRS2, PIK3CD, PLEKHA1, ITK |
| 17 | PKCθ signaling in T cells | 2.19 | 0.211 | 2.75 | 6/133 (5%) | 0/133 (0%) | 22/133 (17%) | 105/133 (79%) | CD247, MAP2K4, RAC2, NFATC3, PIK3R1, CD4, HLA-DQA1, MAP3K5, HLA-DMA, PIK3CG, HLA-DMB, HLA-DRA, MAP3K7, IRS2, PRKCQ, MAP3K6, GRB2, PIK3C2G, TLR9, CD3D, RRAS2, PLCG2, FCER1G, CD86, HLA-DOB, PIK3CD, VAV1, MAP3K3 |
| 18 | Role of pattern recognition receptors in recognition of bacteria and viruses | 1.76 | 0.197 | 2.84 | 5/137 (4%) | 0/137 (0%) | 22/137 (16%) | 110/137 (80%) | MAP2K4, PIK3R1, TLR8, C1QC, C1QA, IL6, CCL5, C1QB, IFIH1, IL17D, PIK3CG, TLR7, CASP1, IRS2, CXCL8, OAS1, PRKCQ, OAS2, GRB2, MYD88, |

TABLE 5-continued

Top 30 canonical pathways in which the HS microarray dataset significantly differed from normal control skin. Data were based on a −log(P-value) cut-off of 1.3 and a Z score activation prediction are of >2 or <−2. Data are ranked by −log(P-value).

| | Ingenuity canonical pathways | −log (P) | Ratio | Z score | Down-regulated | No change | Up-regulated | No overlap | Molecules |
|---|---|---|---|---|---|---|---|---|---|
| 19 | Acute phase response signaling | 1.7 | 0.188 | 3.27 | 5/170 (3%) | 0/170 (0%) | 27/170 (16%) | 138/170 (81%) | PIK3C2G, TLR9, IRF7, SYK, PLCG2, IL1B, PIK3CD MAP2K4, SOCS3, PIK3R1, SOCS6, IL6, MAP3K5, IL1F10, NR3C1, CIR, SHC1, SOD2, PIK3CG, CFB, MAP3K7, SERPINA1, OSMR, SERPINE1, TNFRSF1B, MAP2K1, MYD88, GRB2, CIS, IL36A, VWF, STAT3, IL37, FTL, RRAS2, IL1B, PIK3CD, A2M, C2 |
| 20 | LPS/IL-1-mediated inhibition of RXR function | 1.69 | 0.18 | 2.14 | 20/222 (9%) | 0/222 (0%) | 20/222 (9%) | 182/222 (82%) | MAP2K4, GSTM5, IL1RL1, IL1F10, HMGCS2, HS3ST3A1, ALDH2, SLC27A5, ACSBG1, UST, IL1RL2, ALDH1A3, ALDH3A2, ACSL5, MAP3K7, ACSL4, FABP7, FMO1, TNFRSF1B, GSTA2, FMO3, MYD88, IL36A, NR1H3, IL37, GSTO1, IL18RAP, LY96, ALDH1L2, SMOX, CAT, NCOA1, CD14, IL1B, ALDH3B1, SLC27A3, HS3ST6, RXRA, MGST3, PPARGC1A |
| 21 | GP6 signaling pathway | 1.63 | 0.194 | 2.75 | 6/134 (4%) | 0/134 (0%) | 20/134 (15%) | 108/134 (81%) | COL4A5, PIK3R1, COL4A2, COL6A6, COL15A1, COL5A1, RHOG, PIK3CG, LAMB1, IRS2, COL5A2, PRKCQ, COL4A1, APBB1IP, GRB2, PIK3C2G, LAMC3, TLR9, LAMC2, BTK, COL6A3, SYK, PLCG2, LYN, FCER1G, PIK3CD |

TABLE 5-continued

Top 30 canonical pathways in which the HS microarray dataset significantly differed
from normal control skin. Data were based on a −log(P-value) cut-off of 1.3 and
a Z score activation prediction are of >2 or <−2. Data are ranked by −log(P-value).

| | Ingenuity canonical pathways | −log (P) | Ratio | Z score | Down-regulated | No change | Up-regulated | No overlap | Molecules |
|---|---|---|---|---|---|---|---|---|---|
| 22 | Retinoic acid-mediated apoptosis signaling | 1.58 | 0.226 | 2.50 | 3/62 (5%) | 0/62 (0%) | 11/62 (18%) | 48/62 (77%) | CASP3, PARP10, PARP2, TNFRSF10B, ZC3HAV1, TNFSF10, PARP3, PARP9, IRF1, TIPARP, BID, RXRA, IFNAR1, PARP14 |
| 23 | Tumouricidal function of hepatic natural killer cells | 1.53 | 0.292 | 2.24 | 0/24 (0%) | 0/24 (0%) | 7/24 (29%) | 17/24 (71%) | M6PR, CASP3, GZMB, SRGN, BID, BAX, AIFM1 |
| 24 | B-cell receptor signaling | 1.45 | 0.178 | 2.48 | 7/191 (4%) | 0/191 (0%) | 27/191 (14%) | 157/191 (82%) | MAP2K4, RAC2, NFATC3, PIK3R1, MAP3K5, OCRL, PTPRC, SHC1, PIK3CG, MAP3K7, IRS2, MAP2K1, ETS1, PTPN6, PRKCQ, APBB1IP, CFL1, MAP3K6, CD79B, GRB2, FCGR2A, CSK, PIK3C2G, CD79A, TLR9, BTK, BCL2L1, RRAS2, PLCG2, SYK, LYN, PIK3CD, VAV1, MAP3K3 |
| 25 | PPAR signaling | 1.44 | 0.2 | −2.52 | 7/95 (7%) | 0/95 (0%) | 12/95 (13%) | 76/95 (80%) | GRB2, IL1RL1, IL36A, NR1H3, IL1F10, IL37, PDGFC, IL18RAP, SHC1, HSP90B1, RRAS2, IL1RL2, MAP3K7, NCOA1, IL1B, RXRA, TNFRSF1B, MAP2K1, PPARGC1A |
| 26 | Thrombopoietin signaling | 1.42 | 0.215 | 2.14 | 3/65 (5%) | 0/65 (0%) | 11/65 (17%) | 51/65 (78%) | SHC1, PRKCQ, RRAS2, GRB2, PLCG2, PIK3CG, PIK3R1, PIK3C2G, PIK3CD, IRS2, STAT3, STAT1, TLR9, MAP2K1 |
| 27 | Calcium-induced T-cell apoptosis | 1.37 | 0.212 | 2.11 | 3/66 (5%) | 0/66 (0%) | 11/66 (17%) | 52/66 (79%) | CD247, PRKCQ, ITPR2, CD4, HDAC1, HLA-DQA1, CD3D, HLA-DMA, HLA-DRA, ITPR3, HLA-DMB, FCER1G, HLA-DOB, ORAI1 |
| 28 | SAPK/JNK signaling | 1.33 | 0.192 | 2.24 | 6/104 (6%) | 0/104 (0%) | 14/104 (13%) | 84/104 (81%) | MAP2K4, MAP4K2, RAC2, GRB2, NFATC3, GNA12, PIK3R1, PIK3C2G, MAP3K5, TLR9, MAP4K3, SHC1, |

TABLE 5-continued

Top 30 canonical pathways in which the HS microarray dataset significantly differed from normal control skin. Data were based on a −log(P-value) cut-off of 1.3 and a Z score activation prediction are of >2 or <−2. Data are ranked by −log(P-value).

| | Ingenuity canonical pathways | −log (P) | Ratio | Z score | Down-regulated | No change | Up-regulated | No overlap | Molecules |
|---|---|---|---|---|---|---|---|---|---|
| 29 | PI3K signaling in B lymphocytes | 1.32 | 0.185 | 2.13 | 8/130 (6%) | 0/130 (0%) | 16/130 (12%) | 106/130 (82%) | RRAS2, PIK3CG, MAP3K7, FCER1G, PIK3CD, IRS2, MAP4K1, MAP3K3 IL4R, PLCB2, CD79B, ATF5, NFATC3, ITPR2, PIK3R1, CD79A, ATF6, PLCH2, PTPRC, BTK, PLCD3, RRAS2, SYK, PIK3CG, PLCG2, ITPR3, LYN, PIK3CD, IRS2, VAV1, PLEKHA1, MAP2K1 |
| 30 | Telomerase signaling | 1.31 | 0.189 | 2.36 | 8/111 (7%) | 0/111 (0%) | 13/111 (12%) | 90/111 (81%) | ETS1, GRB2, PPP2R2A, PIK3R1, HDAC1, PIK3C2G, TLR9, SHC1, RB1, ELF4, HSP90B1, RRAS2, HDAC11, PIK3CG, PPP2R2B, PPM1L, IRS2, PIK3CD, MAP2K1, ELK3, EGFR |

Where FcγRIIB refers to Fcγ receptor IIB; GP6, glycoprotein 6; iCOS, inducible costimulator; iCOSL, inducible costimulator ligand; IL, interleukin; JAK, Janus kinase; JNK, Jun kinase; LPS, lipopolysaccharide; NFAT, nuclear factor of activated T cells; NO, nitric oxide; PI3K, phosphoinositide 3-kinase; PKC, protein kinase C; PPAR, peroxisome proliferator-activated receptor; ROS, reactive oxygen species; RXR, retinoid X receptor; SAPK, stress-activated protein kinase; STAT, signal transducer and activation of T cells; Th, T helper; and TREM1, triggering receptor expressed on myeloid cells 1.

Example 4

Differential gene expression in the Interferon signaling pathway between HS and control samples. Using the microarray dataset obtained in Example 2, functional pathway analysis was used to identify biological functions and pathways associated with HS. Those with P<0.05 (Fisher exact test) were considered to be statistically significant. The IPA observed differences in gene expression between the HS and normal skin samples. The Z score was used as a statistical measure of the match between the expected relationship direction and the observed gene expression. A Z score of >2 or <−2 was considered significant.

Figure 2:
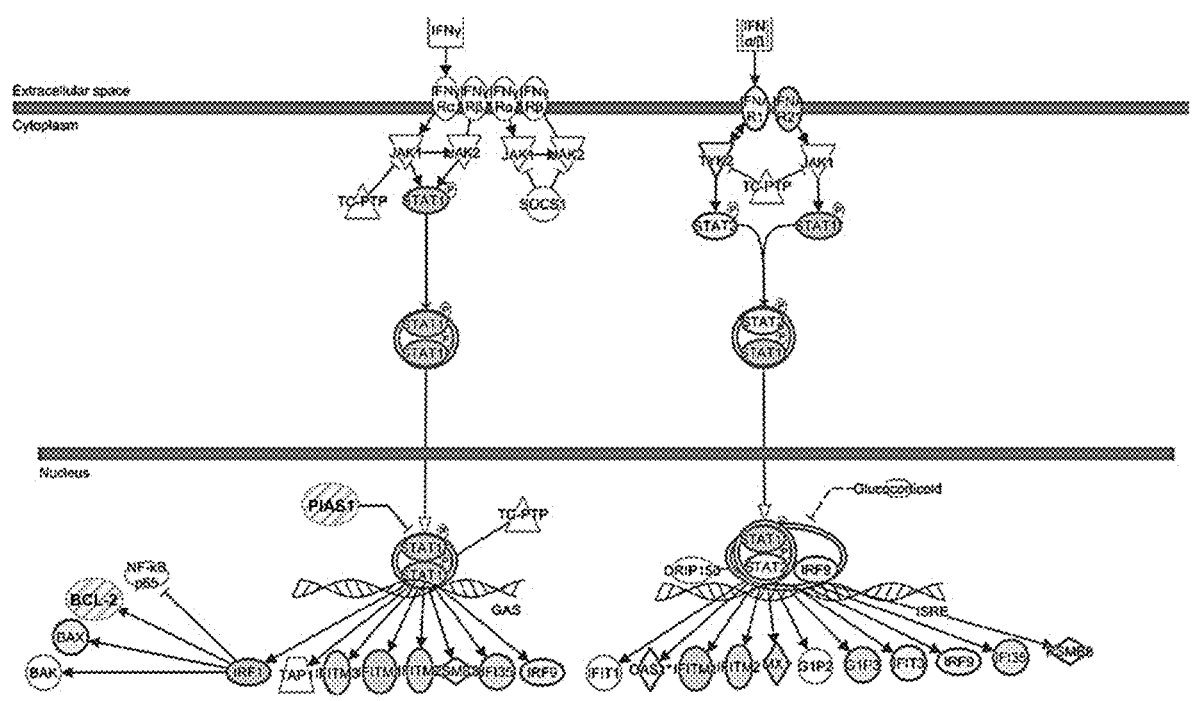
FIG. 2 depicts an image of the key receptors and downstream effectors in the interferon pathway that were upregulated in the hidradenitis suppurativa (HS) samples compared to healthy (normal) samples as measured by microarray analysis. Upregulated molecules are depicted as solid grey objects, downregulated molecules are depicted as grey striped objects, and pathway molecules that were not in the dataset are white. Double outlined shapes indicate groups of molecules.

Based on gene expression in the HS samples, the IFN-signaling pathway demonstrated differential expression of 19 of 36 molecules (Z score 4.24, P<0.001) (Table 6). The observed expression change in HS samples was compared to normal controls with log ratio and p-value. FIG. 2 provides a biological picture of the IFN pathway, showing the key receptors and downstream effectors that are upregulated in the HS samples. These findings predict that the IFN pathway is activated in HS compared with healthy control (HC) skin.

TABLE 6

Differential expression of specific molecules in the interferon pathway. Molecules are ranked by expression intensity.

| Symbol | Entrez Gene Name | Expr p-value | Expr Log Ratio | Expr Intensity/ RPKM/FPKM/ Counts | Expected | Molecule Location | Type of molecule |
|---|---|---|---|---|---|---|---|
| BAX | BCL2 associated X, apoptosis regulator | 0.00795 | 0.785 | 6.831 | Up | Cytoplasm | Transporter |
| IFI6 | interferon alpha inducible protein 6 | 0.00516 | 1.132 | 5.958 | Up | Cytoplasm | Other |

TABLE 6-continued

Differential expression of specific molecules in the interferon pathway. Molecules are ranked by expression intensity.

| Symbol | Entrez Gene Name | Expr p-value | Expr Log Ratio | Expr Intensity/ RPKM/FPKM/ Counts | Expected | Molecule Location | Type of molecule |
|---|---|---|---|---|---|---|---|
| IFI35 | interferon induced protein 35 | 0.00413 | 1.057 | 6.57 | Up | Nucleus | Other |
| IFIT3 | interferon induced protein with tetratricopeptide repeats 3 | 0.0418 | 0.468 | 4.65 | Up | Cytoplasm | Other |
| IFITM1 | interferon induced transmembrane protein 1 | 0.00045 | 1.483 | 8.227 | Up | Plasma Membrane | transmembrane receptor |
| IFITM2 | interferon induced transmembrane protein 2 | 0.00309 | 1.211 | 10.319 | Up | Cytoplasm | Other |
| IFITM3 | interferon induced transmembrane protein 3 | 0.005 | 1.134 | 9.924 | Up | Plasma Membrane | Other |
| IFNAR1 | interferon alpha and beta receptor subunit 1 | 0.0042 | 0.776 | 6.223 | Up | Plasma Membrane | transmembrane receptor |
| IFNAR2 | interferon alpha and beta receptor subunit 2 | 0.00845 | 1.439 | 6.006 | Up | Plasma Membrane | transmembrane receptor |
| IRF1 | interferon regulatory factor 1 | 0.000854 | 1.818 | 7.198 | Up | Nucleus | transcription regulator |
| MX1 | MX dynamin like GTPase 1 | 0.012 | 1.269 | 7.896 | Up | Cytoplasm | Enzyme |
| OAS1 | 2'-5'-oligoadenylate synthetase 1 | 0.0452 | 0.597 | 4.967 | Up | Cytoplasm | Enzyme |
| PSMB8 | proteasome subunit beta 8 | 0.025 | 0.626 | 5.866 | Up | Cytoplasm | Peptidase |
| STAT1 | signal transducer and activator of transcription 1 | 0.00282 | 1.837 | 6.286 | Up | Nucleus | transcription regulator |
| STAT2 | signal transducer and activator of transcription 2 | 0.00235 | 0.864 | 9.168 | Up | Nucleus | transcription regulator |
| TYK2 | tyrosine kinase 2 | 0.0437 | 0.495 | 8.089 | Up | Plasma Membrane | Kinase |
| BCL2 | BCL2, apoptosis regulator | 0.00181 | −0.837 | 5.825 | Down | Cytoplasm | Transporter |
| PIAS1 | protein inhibitor of activated STAT 1 | 0.0185 | −0.423 | 7.614 | Down | Nucleus | transcription regulator |
| IRF9 | interferon regulatory factor 9 | 0.00162 | 0.827 | 8.155 | | Nucleus | transcription regulator |

Example 5

Differential gene expression in the leucocyte extravasation-signaling pathway between HS and control samples. Using the microarray dataset obtained in Example 2, functional pathway analysis was used to identify biological functions and pathways associated with HS. Those with P<0.05 (Fisher exact test) were considered to be statistically significant. The IPA observed differences in gene expression between the HS and normal skin samples. The Z score was used as a statistical measure of the match between the expected relationship direction and the observed gene expression. A Z score of >2 or <−2 was considered significant.

The leucocyte extravasation-signaling pathway was also predicted to be activated, with differential expression found for 57 of 211 molecules in this pathway (Z score 2.10, P<0.001) (Table 7). The observed expression change in HS samples was compared to normal controls with log ratio and p-value. Numerous molecules involved in leucocyte capture and tethering via endothelial cells were upregulated in the HS compared with HC samples.

TABLE 7

Differential expression of specific molecules in the leucocyte extravasation-signaling pathway. Molecules are ranked by expression intensity.

| Symbol | Entrez Gene Name | Expr p-value | Expr Log Ratio | Expr Intensity/ RPKM/FPKM Counts | Expected | Molecule Location | Type of molecule |
|---|---|---|---|---|---|---|---|
| ACTB | actin beta | 0.0448 | 0.496 | 11.916 | Up | Cytoplasm | Other |
| MYL6 | myosin light chain 6 | 0.0192 | 0.364 | 11.744 | Up | Cytoplasm | Enzyme |
| EZR | Ezrin | 0.0492 | −0.581 | 10.851 | Up | Plasma Membrane | Other |
| ITGB2 | integrin subunit beta 2 | 0.00414 | 1.653 | 9.135 | Up | Plasma Membrane | transmembrane receptor |
| MSN | moesin | 0.0111 | 0.603 | 8.705 | Up | Plasma Membrane | Other |
| CTNNA1 | catenin alpha 1 | 0.022 | −0.366 | 8.503 | Up | Plasma Membrane | other |
| GNAI2 | G protein subunit alpha i2 | 0.0289 | 0.715 | 8.239 | Up | Plasma Membrane | enzyme |
| ACTN4 | actinin alpha 4 | 0.035 | −0.449 | 8.181 | Up | Cytoplasm | transcription regulator |
| ACTN1 | actinin alpha 1 | 0.0192 | 0.927 | 8.154 | Up | Cytoplasm | transcription regulator |
| CYBA | cytochrome b-245 alpha chain | 0.00305 | 2.304 | 8.081 | Up | Cytoplasm | enzyme |
| WASL | Wiskott-Aldrich syndrome like | 0.0438 | −0.431 | 8.028 | Up | Cytoplasm | other |
| RAC2 | Rac family small GTPase 2 | 0.000914 | 2.165 | 7.902 | Up | Cytoplasm | enzyme |
| THY1 | Thy-1 cell surface antigen | 0.00182 | 2.314 | 7.729 | Up | Plasma Membrane | other |
| PIK3R1 | phosphoinositide-3-kinase regulatory subunit 1 | 0.0331 | −0.477 | 7.642 | Up | Cytoplasm | kinase |
| VCAM1 | vascular cell adhesion molecule 1 | 0.00781 | 1.744 | 7.546 | Up | Plasma Membrane | transmembrane receptor |
| PECAM1 | platelet and endothelial cell adhesion molecule 1 | 0.00554 | 1.504 | 7.441 | Up | Plasma Membrane | other |
| PLCG2 | phospholipase C gamma 2 | 0.00817 | 1.493 | 7.069 | Up | Cytoplasm | enzyme |
| ICAM3 | intercellular adhesion molecule 3 | 0.0063 | 1.68 | 7.031 | Up | Plasma Membrane | transmembrane receptor |
| WAS | Wiskott-Aldrich syndrome | 0.00128 | 1.83 | 6.759 | Up | Cytoplasm | other |
| MAP2K4 | mitogen-activated protein kinase kinase 4 | 0.0365 | −0.397 | 6.725 | Up | Cytoplasm | kinase |
| IRS2 | insulin receptor substrate 2 | 0.0259 | −0.842 | 6.633 | Up | Cytoplasm | enzyme |
| MMP28 | matrix metallopeptidase 28 | 0.0041 | −1.501 | 6.578 | Up | Extracellular Space | peptidase |
| MMP9 | matrix metallopeptidase 9 | 0.00317 | 2.712 | 6.484 | Up | Extracellular Space | peptidase |
| CXCL12 | C-X-C motif chemokine ligand 12 | 0.0179 | 1.377 | 6.481 | Up | Extracellular Space | cytokine |
| GRB2 | growth factor receptor bound protein 2 | 0.00853 | 0.831 | 6.473 | Up | Cytoplasm | kinase |
| BTK | Bruton tyrosine kinase | 0.00267 | 1.226 | 5.986 | Up | Cytoplasm | kinase |
| PIK3CG | phosphatidylinositol-4,5-bisphosphate 3-kinase catalytic subunit gamma | 0.0455 | 0.839 | 5.671 | Up | Cytoplasm | kinase |
| MMP3 | matrix metallopeptidase 3 | 0.0177 | 3.119 | 5.607 | Up | Extracellular Space | peptidase |
| RAPGEF4 | Rap guanine nucleotide exchange factor 4 | 2.88E−05 | −0.981 | 5.472 | Up | Cytoplasm | other |

TABLE 7-continued

Differential expression of specific molecules in the leucocyte extravasation-signaling pathway. Molecules are ranked by expression intensity.

| Symbol | Entrez Gene Name | Expr p-value | Expr Log Ratio | Expr Intensity/ RPKM/FPKM Counts | Expected | Molecule Location | Type of molecule |
|---|---|---|---|---|---|---|---|
| WIPF1 | WAS/WASL interacting protein family member 1 | 0.00913 | 0.933 | 5.463 | Up | Cytoplasm | other |
| GNAI1 | G protein subunit alpha i1 | 0.00375 | −0.673 | 5.406 | Up | Plasma Membrane | enzyme |
| PIK3C2G | phosphatidylinositol-4-phosphate 3-kinase catalytic subunit type 2 gamma | 0.00383 | −0.894 | 5.259 | Up | Cytoplasm | kinase |
| ITK | IL2 inducible T-cell kinase | 0.0095 | 0.963 | 5.227 | Up | Cytoplasm | kinase |
| CXCR4 | C-X-C motif chemokine receptor 4 | 0.00457 | 1.455 | 5.136 | Up | Plasma Membrane | G-protein coupled receptor |
| NCF4 | neutrophil cytosolic factor 4 | 0.00933 | 0.973 | 5.055 | Up | Cytoplasm | enzyme |
| PIK3CD | phosphatidylinositol-4,5-bisphosphate 3-kinase catalytic subunit delta | 0.0318 | 0.571 | 5.016 | Up | Cytoplasm | kinase |
| MMP27 | matrix metallopeptidase 27 | 0.0131 | −0.715 | 4.963 | Up | Cytoplasm | peptidase |
| CTNND1 | catenin delta 1 | 0.0132 | −0.428 | 4.954 | Up | Nucleus | other |
| NCF1 | neutrophil cytosolic factor 1 | 0.0127 | 1.042 | 4.891 | Up | Cytoplasm | enzyme |
| PRKCQ | protein kinase C theta | 0.00855 | 0.568 | 4.848 | Up | Cytoplasm | kinase |
| VAV1 | vav guanine nucleotide exchange factor 1 | 0.0388 | 0.482 | 4.794 | Up | Nucleus | transcription regulator |
| ITGA4 | integrin subunit alpha 4 | 0.0363 | 0.369 | 4.701 | Up | Plasma Membrane | transmembrane receptor |
| MMP23B | matrix metallopeptidase 23B | 0.0155 | 0.506 | 4.697 | Up | Extracellular Space | peptidase |
| TLR9 | toll like receptor 9 | 0.0449 | 0.401 | 4.563 | Up | Plasma Membrane | transmembrane receptor |
| TIMP1 | TIMP metallopeptidase inhibitor 1 | 0.0241 | 1.295 | 10.08 | Down | Extracellular Space | cytokine |
| ARHGAP1 | Rho GTPase activating protein 1 | 0.0275 | 0.413 | 7.973 | Down | Cytoplasm | other |
| SIPA1 | signal-induced proliferation-associated 1 | 0.00734 | 0.763 | 6.626 | Down | Cytoplasm | other |
| ARHGAP12 | Rho GTPase activating protein 12 | 0.00352 | −0.65 | 6.12 | Down | Cytoplasm | other |
| ARHGAP4 | Rho GTPase activating protein 4 | 0.00862 | 1.061 | 5.991 | Down | Cytoplasm | other |
| ARHGAP9 | Rho GTPase activating protein 9 | 0.00419 | 1.247 | 5.929 | Down | Cytoplasm | other |
| RAP1GAP | RAP1 GTPase activating protein | 0.018 | −0.685 | 5.21 | Down | Cytoplasm | other |
| CLDN1 | claudin 1 | 0.0217 | −2.957 | 8.934 | | Plasma Membrane | other |
| CLDN23 | claudin 23 | 2.04E−06 | −1.851 | 7.431 | | Plasma Membrane | other |
| CLDN11 | claudin 11 | 0.0234 | −1.68 | 6.68 | | Plasma Membrane | other |
| CLDN8 | claudin 8 | 0.000028 | −2.197 | 5.969 | | Plasma Membrane | other |

TABLE 7-continued

Differential expression of specific molecules in the leucocyte extravasation-signaling pathway. Molecules are ranked by expression intensity.

| Symbol | Entrez Gene Name | Expr p-value | Expr Log Ratio | Expr Intensity/ RPKM/FPKM Counts | Expected | Molecule Location | Type of molecule |
|---|---|---|---|---|---|---|---|
| CYBB | cytochrome b-245 beta chain | 0.0142 | 1.324 | 5.665 | | Cytoplasm | enzyme |
| CLDN14 | claudin 14 | 0.0326 | 0.278 | 4.607 | | Plasma Membrane | other |

Example 6

Differential gene expression in T helper 1 and T helper 2 pathways between HS and control samples. Using the microarray dataset obtained in Example 2, functional pathway analysis was used to identify biological functions and pathways associated with HS. Those with P<0.05 (Fisher exact test) were considered to be statistically significant. The IPA observed differences in gene expression between the HS and normal skin samples. The Z score was used as a statistical measure of the match between the expected relationship direction and the observed gene expression. A Z score of >2 or <−2 was considered significant.

Transcriptome data also predicted that the T helper (Th)1 pathway is activated in HS, with differential expression of 39 of 135 molecules in this pathway (Z score 3.77, P<0.001) (Table 8). The observed expression change in HS samples was compared to normal controls with log ratio and p-value.

TABLE 8

Differential expression of specific molecules in the T helper (Th)1 pathway. Molecules are ranked by expression intensity with known drug targets listed.

| Symbol | Entrez Gene Name | Expr p-value | Expr Log Ratio | Expr Intensity/ RPKM/FPKM Counts | Expected | Molecule Location | Type of molecule |
|---|---|---|---|---|---|---|---|
| APH1B | aph-1 homolog B, gamma-secretase subunit | 0.0199 | 0.78 | 5.439 | Up | Other | peptidase |
| CD4 | CD4 molecule | 0.0224 | 0.677 | 5.056 | Up | Plasma Membrane | transmembrane receptor |
| CD86 | CD86 molecule | 0.014 | 1.194 | 6.342 | Up | Plasma Membrane | transmembrane receptor |
| CD247 | CD247 molecule | 0.000974 | 1.766 | 5.88 | Up | Plasma Membrane | transmembrane receptor |
| CD3D | CD3d molecule | 0.00183 | 1.773 | 6.147 | Up | Plasma Membrane | transmembrane receptor |
| CD8A | CD8a molecule | 0.0203 | 1.076 | 5.452 | | Plasma Membrane | other |
| GATA3 | GATA binding protein 3 | 0.00391 | −1.801 | 6.59 | Down | Nucleus | transcription regulator |
| GRB2 | growth factor receptor bound protein 2 | 0.00853 | 0.831 | 6.473 | Up | Cytoplasm | kinase |
| HLA-DMA | major histocompatibility complex, class II, DM alpha | 0.00463 | 1.328 | 9.087 | Up | Plasma Membrane | transmembrane receptor |
| HLA-DMB | major histocompatibility complex, class II, DM beta | 0.00596 | 1.248 | 9.113 | Up | Plasma Membrane | transmembrane receptor |
| HLA-DOB | major histocompatibility complex, class II, DO beta | 0.0407 | 0.862 | 5.203 | Up | Plasma Membrane | transmembrane receptor |
| HLA-DPB1 | major histocompatibility complex, class II, DP beta 1 | 0.0198 | 1.213 | 6.006 | | Plasma Membrane | transmembrane receptor |

TABLE 8-continued

Differential expression of specific molecules in the T helper (Th)1 pathway.
Molecules are ranked by expression intensity with known drug targets listed.

| Symbol | Entrez Gene Name | Expr p-value | Expr Log Ratio | Expr Intensity/ RPKM/FPKM Counts | Expected | Molecule Location | Type of molecule |
|---|---|---|---|---|---|---|---|
| HLA-DQA1 | major histocompatibility complex, class II, DQ alpha 1 | 0.0457 | 1.127 | 8.178 | Up | Plasma Membrane | transmembrane receptor |
| HLA-DQB2 | major histocompatibility complex, class II, DQ beta 2 | 0.00781 | −2.126 | 7.606 | | Plasma Membrane | transmembrane receptor |
| HLA-DRA | major histocompatibility complex, class II, DR alpha | 0.0198 | 1.069 | 10.236 | Up | Plasma Membrane | transmembrane receptor |
| ICOS | inducible T-cell costimulator | 0.0315 | 0.684 | 4.826 | Up | Plasma Membrane | transmembrane receptor |
| IFNAR1 | interferon alpha and beta receptor subunit 1 | 0.0042 | 0.776 | 6.223 | Up | Plasma Membrane | transmembrane receptor |
| IL6 | interleukin 6 | 0.0203 | 1.813 | 5.394 | Up | Extracellular Space | cytokine |
| IL10RA | interleukin 10 receptor subunit alpha | 0.00743 | 1.151 | 5.47 | | Plasma Membrane | transmembrane receptor |
| IL10RB | interleukin 10 receptor subunit beta | 0.0403 | 0.403 | 8.37 | | Plasma Membrane | transmembrane receptor |
| IRF1 | interferon regulatory factor 1 | 0.000854 | 1.818 | 7.198 | Down | Nucleus | transcription regulator |
| IRS2 | insulin receptor substrate 2 | 0.0259 | −0.842 | 6.633 | Up | Cytoplasm | enzyme |
| ITGB2 | integrin subunit beta 2 | 0.00414 | 1.653 | 9.135 | | Plasma Membrane | transmembrane receptor |
| LGALS9 | galectin 9 | 0.0132 | 0.767 | 4.84 | | Plasma Membrane | other |
| mir-21 | microRNA 21 | 0.00426 | 0.487 | 4.787 | Up | Cytoplasm | microRNA |
| NCSTN | nicastrin | 0.0396 | 0.331 | 8.523 | Up | Plasma Membrane | peptidase |
| NFATC3 | nuclear factor of activated T-cells 3 | 0.0459 | −0.354 | 5.6 | | Nucleus | transcription regulator |
| PIK3C2G | phosphatidylinositol-4-phosphate 3-kinase catalytic subunit type 2 gamma | 0.00383 | −0.894 | 5.259 | Up | Cytoplasm | kinase |
| PIK3CD | phosphatidylinositol-4,5-bisphosphate 3-kinase catalytic subunit delta | 0.0318 | 0.571 | 5.016 | Up | Cytoplasm | kinase |
| PIK3CG | phosphatidylinositol-4,5-bisphosphate 3-kinase catalytic subunit gamma | 0.0455 | 0.839 | 5.671 | Up | Cytoplasm | kinase |
| PIK3R1 | phosphoinositide-3-kinase regulatory subunit 1 | 0.0331 | −0.477 | 7.642 | Up | Cytoplasm | kinase |
| PRKCQ | protein kinase C theta | 0.00855 | 0.568 | 4.848 | Up | Cytoplasm | kinase |
| SOCS3 | suppressor of cytokine signaling 3 | 0.0141 | 1.117 | 5.233 | Down | Cytoplasm | phosphatase |
| STAT1 | signal transducer and activator of transcription 1 | 0.00282 | 1.837 | 6.286 | Up | Nucleus | transcription regulator |

TABLE 8-continued

Differential expression of specific molecules in the T helper (Th)1 pathway.
Molecules are ranked by expression intensity with known drug targets listed.

| Symbol | Entrez Gene Name | Expr p-value | Expr Log Ratio | Expr Intensity/ RPKM/FPKM Counts | Expected | Molecule Location | Type of molecule |
|---|---|---|---|---|---|---|---|
| STAT3 | signal transducer and activator of transcription 3 | 0.00732 | 0.502 | 6.112 | Up | Nucleus | transcription regulator |
| STAT4 | signal transducer and activator of transcription 4 | 0.00571 | 1.134 | 5.478 | Up | Nucleus | transcription regulator |
| TLR9 | toll like receptor 9 | 0.0449 | 0.401 | 4.563 | Up | Plasma Membrane | transmembrane receptor |
| TYK2 | tyrosine kinase 2 | 0.0437 | 0.495 | 8.089 | Up | Plasma Membrane | kinase |
| VAV1 | vav guanine nucleotide exchange factor 1 | 0.0388 | 0.482 | 4.794 | Up | Nucleus | transcription regulator |

Several molecules, including CD4, CD86, CD3d, IL-6, IFN-α and IFN-β receptor subunit 1, Toll-like receptor 9 and tyrosine kinase 2 were upregulated in the HS samples. In the Th2 pathway 30 molecules demonstrated upregulated transcription and 9 demonstrated downregulated transcription (Z score 2.65, P<0.001) (Table 9). The observed expression change in HS samples was compared to normal controls with log ratio and p-value.

TABLE 9

Differential expression of specific molecules in the T helper (Th)2 pathway.
Molecules are ranked by expression intensity with known drug targets listed.

| Symbol | Entrez Gene Name | Expr p-value | Expr Log Ratio | Expr Intensity/ RPKM/FPKM/ Counts | Expected | Molecule Location | Type of molecule |
|---|---|---|---|---|---|---|---|
| ACVR1B | activin A receptor type 1B | 0.00389 | −1.015 | 7.456 | Down | Plasma Membrane | kinase |
| ACVR2A | activin A receptor type 2A | 0.00592 | −0.668 | 5.288 | Down | Plasma Membrane | kinase |
| APH1B | aph-1 homolog B, gamma-secretase subunit | 0.0199 | 0.78 | 5.439 | Up | Other | peptidase |
| CD4 | CD4 molecule | 0.0224 | 0.677 | 5.056 | | Plasma Membrane | transmembrane receptor |
| CD86 | CD86 molecule | 0.014 | 1.194 | 6.342 | Up | Plasma Membrane | transmembrane receptor |
| CD247 | CD247 molecule | 0.000974 | 1.766 | 5.88 | Up | Plasma Membrane | transmembrane receptor |
| CD3D | CD3d molecule | 0.00183 | 1.773 | 6.147 | Up | Plasma Membrane | transmembrane receptor |
| CXCR4 | C-X-C motif chemokine receptor 4 | 0.00457 | 1.455 | 5.136 | Up | Plasma Membrane | G-protein coupled receptor |
| GATA3 | GATA binding protein 3 | 0.00391 | −1.801 | 6.59 | Up | Nucleus | transcription regulator |
| GRB2 | growth factor receptor bound protein 2 | 0.00853 | 0.831 | 6.473 | Up | Cytoplasm | kinase |
| HLA-DMA | major histocompatibility complex, class II, DM alpha | 0.00463 | 1.328 | 9.087 | | Plasma Membrane | transmembrane receptor |
| HLA-DMB | major histocompatibility complex, class II, DM beta | 0.00596 | 1.248 | 9.113 | | Plasma Membrane | transmembrane receptor |
| HLA-DOB | major histocompatibility complex, class II, DO beta | 0.0407 | 0.862 | 5.203 | | Plasma Membrane | transmembrane receptor |

TABLE 9-continued

Differential expression of specific molecules in the T helper (Th)2 pathway.
Molecules are ranked by expression intensity with known drug targets listed.

| Symbol | Entrez Gene Name | Expr p-value | Expr Log Ratio | Expr Intensity/ RPKM/FPKM/ Counts | Expected | Molecule Location | Type of molecule |
|---|---|---|---|---|---|---|---|
| HLA-DPB1 | major histocompatibility complex, class II, DP beta 1 | 0.0198 | 1.213 | 6.006 | | Plasma Membrane | transmembrane receptor |
| HLA-DQA1 | major histocompatibility complex, class II, DQ alpha 1 | 0.0457 | 1.127 | 8.178 | | Plasma Membrane | transmembrane receptor |
| HLA-DQB2 | major histocompatibility complex, class II, DQ beta 2 | 0.00781 | −2.126 | 7.606 | | Plasma Membrane | transmembrane receptor |
| HLA-DRA | major histocompatibility complex, class II, DR alpha | 0.0198 | 1.069 | 10.236 | | Plasma Membrane | transmembrane receptor |
| ICOS | inducible T-cell costimulator | 0.0315 | 0.684 | 4.826 | Up | Plasma Membrane | transmembrane receptor |
| IL24 | interleukin 24 | 0.0339 | 0.5 | 4.885 | Up | Extracellular Space | cytokine |
| IL1RL1 | interleukin 1 receptor like 1 | 0.0154 | 0.426 | 4.32 | | Plasma Membrane | transmembrane receptor |
| IL4R | interleukin 4 receptor | 0.000109 | 1.371 | 6.406 | Up | Plasma Membrane | transmembrane receptor |
| IRS2 | insulin receptor substrate 2 | 0.0259 | −0.842 | 6.633 | Up | Cytoplasm | enzyme |
| ITGB2 | integrin subunit beta 2 | 0.00414 | 1.653 | 9.135 | | Plasma Membrane | transmembrane receptor |
| JAG2 | jagged 2 | 0.0134 | −0.781 | 5.929 | Up | Extracellular Space | growth factor |
| mir-21 | microRNA 21 | 0.00426 | 0.487 | 4.787 | | Cytoplasm | microRNA |
| NCSTN | Nicastrin | 0.0396 | 0.331 | 8.523 | Up | Plasma Membrane | peptidase |
| PIK3C2G | phosphatidylinositol-4-phosphate 3-kinase catalytic subunit type 2 gamma | 0.00383 | −0.894 | 5.259 | Up | Cytoplasm | kinase |
| PIK3CD | phosphatidylinositol-4,5-bisphosphate 3-kinase catalytic subunit delta | 0.0318 | 0.571 | 5.016 | Up | Cytoplasm | kinase |
| PIK3CG | phosphatidylinositol-4,5-bisphosphate 3-kinase catalytic subunit gamma | 0.0455 | 0.839 | 5.671 | Up | Cytoplasm | kinase |
| PIK3R1 | phosphoinositide-3-kinase regulatory subunit 1 | 0.0331 | −0.477 | 7.642 | Up | Cytoplasm | kinase |
| PRKCQ | protein kinase C theta | 0.00855 | 0.568 | 4.848 | Up | Cytoplasm | kinase |
| S1PR1 | sphingosine-1-phosphate receptor 1 | 0.0245 | 0.596 | 5.457 | Down | Plasma Membrane | G-protein coupled receptor |
| SOCS3 | suppressor of cytokine signaling 3 | 0.0141 | 1.117 | 5.233 | Up | Cytoplasm | phosphatase |
| STAT4 | signal transducer and activator of transcription 4 | 0.00571 | 1.134 | 5.478 | Down | Nucleus | transcription regulator |
| TGFBR3 | transforming growth factor beta receptor 3 | 0.012 | −1.101 | 8.653 | Down | Plasma Membrane | kinase |
| TLR9 | toll like receptor 9 | 0.0449 | 0.401 | 4.563 | Up | Plasma Membrane | transmembrane receptor |
| TNFRSF4 | TNF receptor superfamily member 4 | 0.0262 | 0.63 | 5.13 | Up | Plasma Membrane | transmembrane receptor |
| TYK2 | tyrosine kinase 2 | 0.0437 | 0.495 | 8.089 | Up | Plasma Membrane | kinase |

TABLE 9-continued

Differential expression of specific molecules in the T helper (Th)2 pathway.
Molecules are ranked by expression intensity with known drug targets listed.

| Symbol | Entrez Gene Name | Expr p-value | Expr Log Ratio | Expr Intensity/ RPKM/FPKM/ Counts | Expected | Molecule Location | Type of molecule |
|---|---|---|---|---|---|---|---|
| VAV1 | vav guanine nucleotide exchange factor 1 | 0.0388 | 0.482 | 4.794 | Up | Nucleus | transcription regulator |

Example 7

Differential gene expression in nuclear factor of activated T cells pathway between HS and control samples. Using the microarray dataset obtained in Example 2, functional pathway analysis was used to identify biological functions and pathways associated with HS. Those with P<0.05 (Fisher exact test) were considered to be statistically significant. The IPA observed differences in gene expression between the HS and normal skin samples. The Z score was used as a statistical measure of the match between the expected relationship direction and the observed gene expression. A Z score of >2 or <−2 was considered significant.

Nuclear factor of activated T cells (NFAT) is a group of transcription factors involved in the immune response. Molecules in the NFAT pathway were significantly differentially expressed with 11 downregulated and 33 upregulated (Z score 3.68, P<0.001) (Table 10) in the HS samples.

TABLE 10

Differential expression of specific molecules in the NFAT pathway. Molecules are ranked by expression intensity.

| Symbol | Entrez Gene Name | Expr p-value | Expr Log Ratio | Expr Intensity/ RPKM/FPKM/ Counts | Expected | Molecule Location | Type of molecule |
|---|---|---|---|---|---|---|---|
| BTK | Bruton tyrosine kinase | 0.00267 | 1.226 | 5.986 | Up | Cytoplasm | kinase |
| CD4 | CD4 molecule | 0.0224 | 0.677 | 5.056 | Up | Plasma Membrane | transmembrane receptor |
| CD86 | CD86 molecule | 0.014 | 1.194 | 6.342 | Up | Plasma Membrane | transmembrane receptor |
| CD247 | CD247 molecule | 0.000974 | 1.766 | 5.88 | Up | Plasma Membrane | transmembrane receptor |
| CD3D | CD3d molecule | 0.00183 | 1.773 | 6.147 | Up | Plasma Membrane | transmembrane receptor |
| CD79A | CD79a molecule | 0.0129 | 3.12 | 6.41 | Up | Plasma Membrane | transmembrane receptor |
| CD79B | CD79b molecule | 0.0162 | 1.43 | 6.546 | Up | Plasma Membrane | transmembrane receptor |
| CSNK1D | casein kinase 1 delta | 0.00421 | 0.771 | 6.501 | | Cytoplasm | kinase |
| FCER1A | Fc fragment of IgE receptor Ia | 0.0226 | −1.678 | 8.098 | Up | Plasma Membrane | transmembrane receptor |
| FCER1G | Fc fragment of IgE receptor Ig | 0.0384 | 1.479 | 7.265 | Up | Plasma Membrane | transmembrane receptor |
| FCGR1A | Fc fragment of IgG receptor Ia | 0.0328 | 0.962 | 4.977 | Up | Plasma Membrane | transmembrane receptor |
| FCGR1B | Fc fragment of IgG receptor Ib | 0.0179 | 1.216 | 4.982 | Up | Plasma Membrane | transmembrane receptor |
| FCGR2A | Fc fragment of IgG receptor IIa | 0.0118 | 1.44 | 6.107 | Up | Plasma Membrane | transmembrane receptor |
| FCGR3A/ FCGR3B | Fc fragment of IgG receptor IIIa | 0.0326 | 1.056 | 5.097 | Up | Plasma Membrane | transmembrane receptor |
| GNA11 | G protein subunit alpha 11 | 0.0108 | −0.626 | 6.891 | Up | Plasma Membrane | enzyme |
| GNA12 | G protein subunit alpha 12 | 0.0149 | 0.637 | 5.668 | Up | Plasma Membrane | enzyme |
| GNAI1 | G protein subunit alpha i1 | 0.00375 | −0.673 | 5.406 | Up | Plasma Membrane | enzyme |
| GNAI2 | G protein subunit alpha i2 | 0.0289 | 0.715 | 8.239 | Up | Plasma Membrane | enzyme |
| GNG12 | G protein subunit gamma 12 | 0.0346 | −0.77 | 6.046 | | Plasma Membrane | enzyme |
| GRB2 | growth factor receptor bound protein 2 | 0.00853 | 0.831 | 6.473 | Up | Cytoplasm | kinase |

TABLE 10-continued

Differential expression of specific molecules in the NFAT
pathway. Molecules are ranked by expression intensity.

| Symbol | Entrez Gene Name | Expr p-value | Expr Log Ratio | Expr Intensity/ RPKM/FPKM/ Counts | Expected | Molecule Location | Type of molecule |
|---|---|---|---|---|---|---|---|
| HLA-DMA | major histocompatibility complex, class II, DM alpha | 0.00463 | 1.328 | 9.087 | Up | Plasma Membrane | transmembrane receptor |
| HLA-DMB | major histocompatibility complex, class II, DM beta | 0.00596 | 1.248 | 9.113 | Up | Plasma Membrane | transmembrane receptor |
| HLA-DOB | major histocompatibility complex, class II, DO beta | 0.0407 | 0.862 | 5.203 | Up | Plasma Membrane | transmembrane receptor |
| HLA-DQA1 | major histocompatibility complex, class II, DQ alpha 1 | 0.0457 | 1.127 | 8.178 | Up | Plasma Membrane | transmembrane receptor |
| HLA-DRA | major histocompatibility complex, class II, DR alpha | 0.0198 | 1.069 | 10.236 | Up | Plasma Membrane | transmembrane receptor |
| IRS2 | insulin receptor substrate 2 | 0.0259 | −0.842 | 6.633 | Up | Cytoplasm | enzyme |
| ITK | IL2 inducible T-cell kinase | 0.0095 | 0.963 | 5.227 | Up | Cytoplasm | kinase |
| ITPR2 | inositol 1,4,5-trisphosphate receptor type 2 | 0.00165 | −0.968 | 6.197 | | Cytoplasm | ion channel |
| ITPR3 | inositol 1,4,5-trisphosphate receptor type 3 | 0.00174 | −0.981 | 9.276 | | Cytoplasm | ion channel |
| LYN | LYN proto-oncogene, Src family tyrosine kinase | 0.00407 | 1.479 | 7.598 | Up | Cytoplasm | kinase |
| MAP2K1 | mitogen-activated protein kinase kinase 1 | 0.0435 | 0.403 | 7.14 | Up | Cytoplasm | kinase |
| NFATC3 | nuclear factor of activated T-cells 3 | 0.0459 | −0.354 | 5.6 | Up | Nucleus | transcription regulator |
| ORAI1 | ORAI calcium release-activated calcium modulator 1 | 0.000614 | −0.965 | 6.109 | | Plasma Membrane | ion channel |
| PIK3C2G | phosphatidylinositol-4-phosphate 3-kinase catalytic subunit type 2 gamma | 0.00383 | −0.894 | 5.259 | Up | Cytoplasm | kinase |
| PIK3CD | phosphatidylinositol-4,5-bisphosphate 3-kinase catalytic subunit delta | 0.0318 | 0.571 | 5.016 | Up | Cytoplasm | kinase |
| PIK3CG | phosphatidylinositol-4,5-bisphosphate 3-kinase catalytic subunit gamma | 0.0455 | 0.839 | 5.671 | Up | Cytoplasm | kinase |
| PIK3R1 | phosphoinositide-3-kinase regulatory subunit 1 | 0.0331 | −0.477 | 7.642 | Up | Cytoplasm | kinase |
| PLCB2 | phospholipase C beta 2 | 0.0139 | 0.726 | 4.921 | Up | Cytoplasm | enzyme |
| PLCG2 | phospholipase C gamma 2 | 0.00817 | 1.493 | 7.069 | Up | Cytoplasm | enzyme |
| PRKCQ | protein kinase C theta | 0.00855 | 0.568 | 4.848 | Up | Cytoplasm | kinase |
| RCAN1 | regulator of calcineurin 1 | 0.0254 | 0.972 | 5.221 | Down | Nucleus | transcription regulator |
| RRAS2 | RAS related 2 | 0.0482 | 0.357 | 4.973 | Up | Plasma Membrane | enzyme |

TABLE 10-continued

Differential expression of specific molecules in the NFAT pathway. Molecules are ranked by expression intensity.

| Symbol | Entrez Gene Name | Expr p-value | Expr Log Ratio | Expr Intensity/ RPKM/FPKM/ Counts | Expected | Molecule Location | Type of molecule |
|---|---|---|---|---|---|---|---|
| SYK | spleen associated tyrosine kinase | 0.00619 | 0.841 | 7.024 | Up | Cytoplasm | kinase |
| TLR9 | toll like receptor 9 | 0.0449 | 0.401 | 4.563 | Up | Plasma Membrane | transmembrane receptor |

Example 8

Upstream regulator analysis to identify molecular drivers of differential gene expression in HS and control samples. Upstream regulator analysis was performed to identify molecular drivers of the observed gene expression changes in the HS compared with HC skin samples. Expected relationships in this analysis were derived from the literature and compiled using an Ingenuity Knowledge Base. The analysis predicts regulator activity by examining targets and comparing the actual direction of change of the target with expectations derived from the literature (Table 11).

TABLE 11

Upstream regulators of differential gene expression in HS and control samples.

| Upstream Regulator | Predicted Activation State | Activation z-score | p-value of overlap | Target molecules in dataset | Mechanistic Network |
|---|---|---|---|---|---|
| Interferon alpha | Activated | 8.489 | 1.26E−26 | ACP2, ADA2, ADAM19, AIM2, APOBEC3F, APOBEC3G, APOL1, AUTS2, BCL2, BCL2L1, BCL2L13, BCL3, BMP4, BST2, C19orf66, CASP1, CASP3, CCL2, CCL5, CCND1, CCND2, CCR7, CD38, CD69, CD86, CD8A, CGAS, CH25H, CTH, CXCL10, CXCL8, CXCL9, CYP2E1, DAG1, DUSP6, DYNLT1, EGFR, EIF1, ENPP2, EPSTI1, FCER1A, FCGR1A, GATA3, GBP1, GBP2, GIMAP4, GVINP1, GZMB, GZMH, HELZ2, IDO1, IFI16, IFI27, IFI35, IFI44, IFI6, IFIH1, IFIT2, IFIT3, IFITM1, IFITM2, IFITM3, IFNAR1, IFNAR2, IGFBP4, IGLL1/IGLL5, IL10RA, IL18RAP, IL1B, IL32, IL4R, IL6, IL7, IRF1, IRF4, IRF7, IRF8, IRF9, ISG20, ITGA4, KLRG1, LAIR2, LAP3P2, LGALS9, MCL1, mir-21, MMP28, MMP3, MNDA, MRPL17, MX1, MYD88, NABP1, NKG7, NPM3, OAS1, OAS2, PARP10, PARP14, PARP9, PARVG, PIM2, PLAT, PLSCR1, PNPT1, PSMB8, PSMB9, PTHLH, PYHIN1, RARRES3, RB1, RBX1, S100A9, SAT1, SEPT4, SERPINB1, SLC1A5, SLC2A3, SOCS3, SP100, SP110, STAP1, STAT1, STAT2, STAT3, STAT4, TAP2, TAPBP, TBC1D10A, TLR7, TLR8, TMEM140, TNFSF10, TNFSF13B, TRANK1, TRIB2, TYMP, UBE2L6, VCAM1, WARS, WDFY1, ZC3HAV1, ZNRF3 | 495 (15) |
| IFNG | Activated | 9.593 | 1.08E−20 | A2M, ABCA6, ABCD3, ACTB, ADA2, ADM, ADORA2B, AIF1, AIF1L, AIM2, ALDH1A3, ALKAL2, ALPL, ANGPTL4, APOBEC3G, APOL1, APP, ARAP2, AUTS2, AZGP1, BAX, BBC3, BCAN, BCL2, BCL2L1, BCL2L2, BCL3, BID, BIRC2, BMF, BST2, BTN3A1, BTN3A2, C1QA, C1QB, C1QC, C1R, C2, CALCOCO2, CALHM6, CASP1, CASP3, CASP4, CAT, CCL2, CCL3L3, CCL5, CCL8, CCNA2, CCND1, CCND2, CCNO, CCR2, CCRL2, CD14, CD163, CD163L1, CD2, CD36, CD38, CD4, CD55, CD68, CD72, CD74, CD86, CDH13, CEBPA, CERS6, CFB, CGAS, CH25H, CHI3L2, CIRBP, CLEC2D, CLIC4, COL5A2, CORO1A, CRLF1, CSK, CTSB, CTSC, CTSZ, CXCL10, CXCL12, CXCL8, CXCL9, CXCR4, CYB5A, CYBA, CYBB, CYLD, CYP11A1, CYP2E1, DEGS1, DLG4, E2F5, EDNRA, EFNB2, EGR3, ENO1, ERBB2, FCER1G, FCGR1A, FCGR1B, FCGR2A, FCGR3A/FCGR3B, FCN1, FTL, FZD2, GAD1, GART, GATA3, GBP1, GBP2, GBP4, GBP5, GCHFR, GLA, GLDN, GNAI2, GSDMD, GZMB, HIF1A, | 843 (15) |

TABLE 11-continued

Upstream regulators of differential gene expression in HS and control samples.

| Upstream Regulator | Predicted Activation State | Activation z-score | p-value of overlap | Target molecules in dataset | Mechanistic Network |
|---|---|---|---|---|---|
| | | | | HLA-DMA, HLA-DMB, HLA-DOB, HLA-DQA1, HLA-DRA, HLA-E, IDO1, IFI16, IFI27, IFI30, IFI35, IFI44, IFI6, IFIH1, IFIT2, IFIT3, IFITM1, IFITM2, IFITM3, IGFBP4, IL10RA, IL17D, IL18BP, IL18RAP, IL19, IL1B, IL1RL1, IL22RA1, IL23A, IL32, IL4R, IL6, IL7, IL7R, IRF1, IRF4, IRF7, IRF8, IRF9, IRS2, ISG20, ITGA4, ITGAX, ITGB2, KLF10, KLF4, KLF6, KYNU, LAMC2, LAT2, LGALS3, LGALS3BP, LGALS9, LTB, LY96, LYN, MAP2K1, MARCKSL1, MERTK, MFSD2A, MITF, MMP3, MMP9, MNDA, MST1R, MT1F, MTMR3, MUC1, MX1, MYD88, MYH9, NAMPT, NDRG4, NTF4, NTRK2, NUPR1, OAS1, OAS2, OPTN, P2RY14, PARP9, PARVG, PCDH17, PCTP, PECAM1, PIM2, PLA2G7, PLAU, PLAUR, PLEK, PPARGC1A, PPIA, PPP1R1B, PRDM1, PRKCQ, PSMB10, PSMB8, PSMB9, PSME1, PSME2, PTHLH, PTPN6, RAB27A, RAC2, RARRES3, RB1, RFX5, RORC, S100A7, S100A8, S100A9, SBNO2, SELE, SELL, SELP, SEMA4A, SEPT3, SEPT4, SERPINA1, SERPINE1, SERPINH1, SLAMF1, SLC12A2, SLC15A3, SLC16A3, SLC1A3, SLC29A1, SLC6A1, SLC7A5, SOCS3, SOD2, SP100, SP110, STAT1, STAT2, STAT3, STAT4, SYNM, TAC1, TAP2, TAPBP, TAPBPL, TBC1D10A, TBXAS1, TCIRG1, TGFBR3, THY1, TIMP1, TLR7, TLR8, TLR9, TMEM50B, TNFAIP6, TNFRSF10B, TNFRSF14, TNFRSF1B, TNFRSF9, TNFSF10, TNFSF13B, TPI1, TRIB2, TYMP, TYROBP, UBD, UBE2L6, VCAM1, VIPR1, WARS, WNT5A, ZNF638, ZYX | |
| lipopolysaccharide | Activated | 9.683 | 2.63E-20 | ABCC1, ABCC5, ABCF2, ACP5, ACTN4, ACVR2A, ADA, ADM, ADORA2B, AK4, ALCAM, ALDH2, ALOX12, ALOX5, ANGPT2, ANGPTL4, APLNR, APOBEC3F, APOBEC3G, APP, ARHGAP1, ARHGEF3, ARPC1B, AZGP1, BATF, BAX, BCL2, BCL2L1, BCL3, BID, BIRC2, BMP2, BMP4, BTK, CALR, CASP1, CASP3, CASP4, CCL2, CCL21, CCL3L3, CCL5, CCL8, CCNB2, CCND1, CCND2, CCR2, CCR7, CCRL2, CD14, CD163, CD163L1, CD36, CD37, CD38, CD4, CD48, CD53, CD55, CD69, CD74, CD86, CD8A, CD9, CDC42EP4, CDH11, CEBPA, CEMIP, CFB, CFD, CGAS, CH25H, CLDN1, CLIC4, COL4A1, COL4A2, COL5A1, COL5A2, CORO1A, CRTAP, CRYAB, CSF2RA, CSF3R, CTH, CTSB, CTSC, CTSL, CUX2, CXCL10, CXCL12, CXCL13, CXCL14, CXCL8, CXCL9, CXCR4, CYB5A, CYBA, CYBB, CYP2E1, CYTIP, DAG1, DHCR24, DLG4, DNAJB11, DNMT1, DRAM1, EFNB2, EGR3, ELANE, ELK3, ENO1, ENPP2, EPHX2, ERCC1, ERP44, ETV3, FCER1G, FES, FLI1, FLOT2, FPR1, FSCN1, GBP1, GBP2, GBP4, GBP5, GCA, GCHFR, GEM, GEMIN4, GLRB, GMFG, GNPAT, GNRH1, GPR183, GSN, GUCY1A3, GZMA, GZMB, GZMH, HES5, HIF1A, HIVEP1, HLA-DMA, HLA-DOB, HLA-DQA1, HMGCS2, HSP90B1, HYOU1, ICAM2, IDO1, IFI16, IFI27, IFI35, IFI44, IFI6, IFIH1, IFIT2, IFIT3, IFITM1, IFITM2, IGFBP4, IGSF6, IL10RA, IL10RB, IL13RA1, IL18RAP, IL19, IL1B, IL23A, IL24, IL32, IL36A, IL4R, IL6, IL7, IL7R, IRF1, IRF4, IRF7, IRF8, IRF9, ISG20, ITGA4, ITGAX, ITGB2, JCHAIN, KANK1, KCNJ15, KCNK5, KIAA1551, KLF10, KLF4, KLF6, KYNU, LAMB1, LASP1, LGALS3, LGALS3BP, LGALS9, LIPA, LIPG, LPIN2, LRBA, LY96, LYN, LYZ, M6PR, MAPT, MARCKS, MARCKSL1, MCL1, MCM5, MCTS1, mir-154, mir-21, MME, MMP23B, MMP3, MMP9, MSC, MSN, MST1R, MT2A, MX1, MYD88, MYH14, MYH9, | 934 (14) |

TABLE 11-continued

Upstream regulators of differential gene expression in HS and control samples.

| Upstream Regulator | Predicted Activation State | Activation z-score | p-value of overlap | Target molecules in dataset | Mechanistic Network |
|---|---|---|---|---|---|
| | | | | NAMPT, NCF1, NCOA1, NFIX, NNMT, NOCT, NPTX1, NRIH3, NR3C1, NSFL1C, NUPR1, OAS1, OAS2, 0RAI1, OSMR, OXCT1, PCOLCE2, PDE4B, PDIA4, PECAM1, PI3, PIK3CG, PIK3R1, PIM2, PLA2G7, PLAT, PLAU, PLAUR, PLEK, PLEKHA1, PLSCR1, PNPLA1, POU2AF1, PPARGC1A, PPIA, PPP1CB, PPP1R16B, PRDM1, PSMB10, PSMB8, PSMB9, PSME1, PSME2, PTHLH, PTPN7, PTPRCAP, RAB3B, RALGDS, RARRES3, RB1, RCAN1, RFC1, RGS1, RNASE2, RXRA, S100A12, S100A8, S100A9, S1PR1, SAMSN1, SAP18, SAT1, SELE, SELL, SELP, SEPT4, SERPINA1, SERPINB1, SERPINB2, SERPINE1, SERPINH1, SERPINI1, SIGIRR, SLAMF1, SLAMF7, SLC15A3, SLC16A3, SLC1A5, SLC29A1, SLC39A8, SLC3A2, SNX5, SOCS3, SOD2, ST6GAL1, STAP1, STAT1, STAT2, STAT3, STAT4, STIM1, STX4, TAC1, TACC3, TAPBP, TDO2, TGM2, THY1, TIMP1, TIPARP, TLR7, TLR8, TLR9, TMSB10/TMSB4X, TNC, TNFAIP6, TNFRSF1B, TNFRSF4, TNFRSF9, TNFSF10, TNFSF13B, TNIP1, TNNC1, TNNT2, TOLLIP, TPI1, TYMP, TYROBP, UCP2, VAV1, VCAM1, VNN3, VWF, WARS, WEE1, XAF1, XBP1, ZC3H12A, ZNF281, ZYX | |
| TNF | Activated | 7.927 | 1.52E-19 | A2M, AATK, ABCC1, ABTB2, ACP5, ACTB, ADGRG6, ADM, ADORA2B, AKAP12, ALCAM, ALDH1A3, ALDH2, ALOX5, ANGPT2, ANGPTL4, ANK3, APBA3, APOL1, APP, ARF4, ARHGAP23, ARHGDIB, ATP2B4, AXIN2, B4GALT1, BAX, BBC3, BBOX1, BCL2, BCL2L1, BCL2L13, BCL2L2, BCL3, BID, BIRC2, BLVRA, BMP2, BMP4, BMPR1A, BST2, BTBD3, BTN3A3, C1QTNF1, CALR, CARD16, CASP1, CASP3, CASP4, CAT, CCDC15, CCL2, CCL27, CCL3L3, CCL5, CCND1, CCND2, CCR2, CCR7, CD14, CD163, CD163L1, CD247, CD36, CD38, CD4, CD5, CD55, CD69, CD86, CDC42EP4, CDH11, CDH13, CEBPA, CEBPG, CERS6, CFB, CFD, CH25H, CHI3L2, CLDN11, CLIC4, COL15A1, CRISPLD2, CRLF1, CRY1, CRYAB, CST7, CTDSPL, CTLA4, CTSB, CTSC, CTSZ, CXCL10, CXCL12, CXCL13, CXCL8, CXCL9, CXCR4, CYBA, CYBB, CYLD, CYP11A1, CYP26B1, CYP2E1, CYTH3, CYTIP, DAG1, DCD, DENND4A, DMD, DNMT1, DUSP6, DVL1, EDAR, EFHD2, EFNA1, EFNB2, EGFR, EGR3, ELK3, ENG, ENPP2, ERBB2, ERCC1, ETS1, EXOSC7, FAM198B, FCER1G, FMO1, FPR1, FRMD6, FSCN1, GBP1, GBP2, GEM, GNAI1, GNAI2, GOSR2, GPX1, GRN, HCN3, HDAC1, HIF1A, HIPK2, HIVEP1, HLA-DRA, HLAE, HSD11B1, ICAM2, ICOS, IDH2, IDO1, IFI16, IFI27, IFI6, IFIH1, IFIT3, IFITM1, IFNAR2, IGFBP4, IGFBP6, IL10RA, IL17D, IL18BP, IL19, IL1B, IL1F10, IL1RL1, IL1RL2, IL23A, IL24, IL32, IL36A, IL37, IL4R, IL6, IL7, IL7R, IRF1, IRF4, IRF7, IRF8, IRS2, ITGA4, ITGAX, ITGB2, ITPR2, JAG2, KLF10, KLF4, KLF6, KLK3, KLRB1, KRT23, KYNU, L3MBTL3, LAMC2, LFNG, LGALS3, LGALS8, LGALS9, LSS, LTB, LY96, LYN, MAGI1, MAP2K4, MAP3K7, MARCKSL1, MCL1, MECOM, MEOX1, MFSD2A, mir21, MMP28, MMP3, MMP9, MPC1, MSC, MST1, MST1R, MSX2, MT2A, MUC1, MVP, MX1, MYD88, MYH9, MYL6, NAMPT, NCF1, NCK1, NCOA1, NFE2L2, NNMT, NOCT, NPM3, NR1H3, NR3C1, NRARP, NRROS, OAS1, OAS2, OLFML2B, OPTN, OSMR, PAK2, PARP14, PCP4, PDE4B, PDIA4, PDK3, PDPN, PDZD2, PECAM1, PI3, PIK3CD, PIK3CG, PIM2, PLA2G4A, PLAT, PLAU, PLAUR, PLP1, PLSCR1, PLVAP, PNPLA1, POU2AF1, | 649 (12) |

TABLE 11-continued

Upstream regulators of differential gene expression in HS and control samples.

| Upstream Regulator | Predicted Activation State | Activation z-score | p-value of overlap | Target molecules in dataset | Mechanistic Network |
|---|---|---|---|---|---|
| | | | | PPARGC1A, PRDM1, PSMB10, PSMB8, PSMB9, PSME1, PSME2, PTHLH, PTPRC, RARRES2, RARRES3, RB1, RCAN1, RFTN1, RFX2, RFX5, RGS1, RNASE2, RNASE4, RRM2, RXRA, S100A7, S100A8, S100A9, SAT1, SCO2, SEC22B, SELE, SELL, SELP, SERPINB1, SERPINB2, SERPINB8, SERPINE1, SGK1, SLC1A3, SLC27A5, SLC43A2, SLCO2B1, SMPDL3A, SNCG, SNRK, SOCS3, SOD2, SORBS1, ST3GAL6, ST6GAL1, ST8SIA4, STAT1, STAT4, SYVN1, TAC1, TAPBP, TBC1D8, TBXAS1, TCFL5, TFAP2A, TGM2, THY1, TIMP1, TLR7, TLR8, TMEM176B, TMEM40, TNC, TNFAIP6, TNFRSF10B, TNFRSF18, TNFRSF1B, TNFRSF21, TNFRSF4, TNFRSF6B, TNFRSF9, TNFSF10, TNFSF13B, TNIP1, TNNC1, TP53I3, TP53INP1, TYK2, TYMP, UBD, UCP2, VASH1, VCAM1, VIPR1, VMP1, WLS, WNT3A, WNT5A, ZC3H12A, ZYX | |
| OSM | Activated | 7.511 | 6.33E−18 | A2M, ABCC1, ABCC5, ACSL5, ADGRG6, AKR1C3, ANGPT2, ARHGEF12, ARHGEF2, ARL4A, ATP2B4, BAIAP2, BBOX1, BCL2, BTC, C1R, C1S, CADM4, CASP4, CAT, CCL2, CCL5, CCND1, CCND2, CDC42EP4, CEBPA, CH25H, CHI3L2, CLIP1, CRLF1, CRY1, CST6, CTSL, CXCL10, CXCL12, CXCL13, CXCL8, DEGS1, DHCR24, DNAJC3, DNM1L, EPCAM, EPHB6, ERBB3, EXOSC10, FOXN3, GART, GAS7, GBP1, GBP2, GCA, GFPT1, GNS, GPNMB, HIF1A, HSD11B1, HSPA2, HSPB3, IFI35, IGFBP6, IL13RA1, IL1B, IL32, IL4R, IL6, IL7, IRF1, IRF7, IRF9, ISG20, KLF10, KLK1, KRT2, LCE2B, LY6G6C, MAP2, MARCKS, MGLL, MMP3, MMP9, MOAP1, MPDU1, MSC, MT2A, MX1, MYD88, NAMPT, NMT2, OAS1, OSMR, P2RY10, PAK2, PDPN, PGGT1B, PI3, PKIG, PLA2G4A, PLAU, PLLP, PRDM1, PRR4, PSMB8, PSMB9, PTP4A1, PTPN21, PTPRZ1, PYGL, RAB31, RAB4A, RNASE4, RORA, RUNX1, S100A12, S100A7, S100A8, S100A9, SEL1L, SELE, SELP, SEPT9, SERPINA1, SERPINB1, SERPINB8, SERPINE1, SLC16A3, SMAD5, SOCS3, SON, STAT1, STAT3, TAP2, TAPBP, TDO2, TIMP1, TNC, TNNC1, TYMP, TYRO3, UBE2L6, USP46, USP9X, VCAM1, WNT5A, ZC3HAV1 | 765 (16) |

IFN-α, a cytokine that activates Th1 responses, was predicted to be activated in the HS samples (activation Z score 8.49, P<0.001 for overlap) Similarly, IFN-γ, one of the type II interferons that is involved in triggering cellular responses to microbial and viral infection, was predicted to be activated in HS compared with HC skin (activation Z score 9.59, P<0.001 for overlap). Lipopolysaccharide, an immunomodulatory molecule expressed in severe inflammatory conditions such as sepsis, was also predicted to be activated (activation Z score 9.68, P<0.001 for overlap), as was the gene encoding TNF (activation Z score 7.93, P<0.001 for overlap), consistent with existing knowledge that TNF inhibitors are effective as therapies for HS. Oncostatin M, a member of the IL-6 family of proinflammatory cytokines, was predicted to be activated in HS (activation Z score 7.51, P<0.001 for overlap). Oncostatin M regulates the production of IL-6, granulocyte-colony stimulating factor and granulocyte-macrophage colony stimulating factor from endothelial cells and probably exerts effects via the activation of the Janus kinase (JAK) system. The relationship between Oncostatin M activation and HS disease activity has not yet been investigated, but these findings suggest that this pathway merits further investigation in HS.

Discussion of Examples 1-8. This study investigated the gene expression profile in HS lesional skin compared with healthy control (HC) skin, using a comprehensive microarray platform to assess mRNA expression. Differential expression in the HS samples demonstrated prominent inflammatory profiles and two subset subject populations. Notably, IL-37, a molecule that functions to downregulate innate immune responses, was demonstrated to have reduced expression in the HS compared with the HC samples. Additionally, dermcidin, an antimicrobial peptide naturally found in human sweat, was also downregulated in the HS samples. These findings indicate that regulators of the innate immune response and particularly antimicrobial peptide production may play a role in HS pathogenesis.

The interferon-signaling pathway, leucocyte extravasation pathway, Th1/Th2 pathways and NFAT were the top five upregulated pathways in the HS samples. Interferons, in particular IFN-γ, play a critical role in immune activation in response to infections and malignancy. Produced by activated T cells, IFN-γ signals via transmembrane receptors to activate the JAK—signal transducer and activator of T cells (JAK-STAT) and other downstream pathways. IFN-γ is crucial for Th1 differentiation and activation, and also activates macrophages resulting in granuloma formation. The current study demonstrates upregulation of multiple molecules in IFN pathways in HS, providing data to support these pathways as critical drivers in HS pathogenesis, and as potential therapeutic targets and HS disease diagnostics.

The data presented also demonstrate upregulation of genes in both the Th1 and Th2 pathways, which are critical in orchestrating adaptive immune responses. In the current study, T-bet (TBX21), a regulator of immune cell development and function, was upregulated with an activation Z score of 2.01.

In conclusion, the data indicated that multiple biological pathways are disrupted in HS, suggesting that inflammatory pathways, particularly the interferon pathway, pathways of leucocyte activation and signaling and innate immune responses are potential drivers of HS pathogenesis. The data also show differential gene expression between two clusters of HS subjects, indicating that gene expression can be a way to designate what type of treatment for HS should be administered to a specific subset (such as clinical state) of the HS subject population.

What is claimed is:

1. A method of treating a subject with moderate to severe hidradenitis suppurativa (HS), the method comprising:
    a) determining a gene expression level of S100A8, S100A9, NFATC3, dermcidin, and IL-37 in a biological sample of a human subject;
    b) characterizing HS severity by comparing the subject's gene expression levels of S100A8, S100A9, NFATC3, dermcidin, and IL-37 to a sample that does not have HS, wherein HS severity is characterized as moderate to severe when the expression level of at least S100A8, S100A9, and NFATC3, is increased in the subject compared to the sample that does not have HS, and
    the expression level of dermcidin or IL-37 is decreased in the subject compared to the sample that does not have HS; and
    c) administering an antibiotic, a retinoid, a steroid hormone, an anti-inflammatory, or a combination thereof to a subject characterized as having moderate to severe HS.

2. The method of claim 1, wherein the method of characterizing HS severity further comprises characterizing as moderate to severe when the expression level of at least three genes selected from the group consisting of S100A8, S100A9, NFATC3, BTK, CD247, HLA-DMA, or HLS-DMB, is increased in the subject compared to the sample that does not have HS, and
    the expression level of dermcidin and IL-37 is decreased in the subject compared to the sample that does not have HS.

3. The method of claim 1, the subject characterized as having moderate to severe HS is administered an anti-inflammatory.

4. The method of claim 3, wherein the anti-inflammatory is a tumor necrosis factor inhibitor, an interleukin-1 inhibitor, a Janus kinase (JAK) inhibitor, an interleukin-17 inhibitor, an interleukin-23 inhibitor, a Complement component 5a (C5a) inhibitor, or a combination thereof.

5. The method of claim 1, wherein at least one symptom of moderate to severe HS is ameliorated after administering an antibiotic, a retinoid, a steroid hormone, an anti-inflammatory, or a combination thereof the subject characterized with moderate to severe HS.

6. The method of claim 1, wherein the Dermatology Quality of Life Index (DQLI) score is decreased after administering an antibiotic, a retinoid, a steroid hormone, an anti-inflammatory, or a combination thereof the subject characterized with moderate to severe HS.

7. The method of claim 1, wherein abscess and inflammatory nodule count (AN count) is decreased after administering an antibiotic, a retinoid, a steroid hormone, an anti-inflammatory, or a combination thereof the subject characterized with moderate to severe HS.

8. The method of claim 1, wherein the severity of HS does not progress after administering an antibiotic, a retinoid, a steroid hormone, an anti-inflammatory, or a combination thereof the subject characterized with moderate to severe HS.

9. The method of claim 1, wherein the method characterizing HS severity comprises:
    a) obtaining a biological sample of a human subject;
    b) determining the gene expression level of S100A8, S100A9, NFATC3, dermcidin, and IL-37 in the biological sample by contacting the biological sample with a bead,
    wherein the bead comprises at least one oligonucleotide sequence complementary to S100A8, S100A9, NFATC3, dermcidin, and IL-37;
    c) detecting binding between S100A8, S100A9, NFATC3, dermcidin, and IL-37 in the biological sample to the bead comprising at least one oligonucleotide sequence complementary to S100A8, S100A9, NFATC3, dermcidin, and IL-37, wherein detection of a bound oligonucleotide is measured using a fluorescent label; and
    d) characterizing HS severity as moderate to severe when the expression level of at least S100A8, S100A9, and NFATC3 is increased in the subject compared to the sample that does not have HS.

10. A method of treating a subject with moderate to severe hidradenitis suppurativa (HS), the method comprising:
    a) determining gene expression level of S100A8, S100A9, NFATC3, dermcidin, and IL-37 in a biological sample of a human subject;
    b) characterizing HS severity by comparing the subject's gene expression levels of S100A8, S100A9, NFATC3, dermcidin, and IL-37 to a sample that does not have HS,
    wherein HS severity is characterized as moderate to severe when the expression level of NFATC3 is increased at least 1.5-fold, the expression level of S100A8 is increased at least 2-fold and the expression level of S100A9 is increased at least 2-fold in the subject compared to the sample that does not have HS, and the expression level of dermcidin is decreased at least 3-fold and the expression level of IL-37 is decreased at least 2-fold in the subject compared to the sample that does not have HS; and
    c) administering an antibiotic, a retinoid, a steroid hormone, an anti-inflammatory, or a combination thereof to a subject characterized as having moderate to severe HS.

11. The method of claim 10, the subject characterized as having moderate to severe HS is administered an anti-inflammatory.

12. The method of claim 11, wherein the anti-inflammatory is a tumor necrosis factor inhibitor, an interleukin-1 inhibitor, a Janus kinase (JAK) inhibitor, an interleukin-17 inhibitor, an interleukin-23 inhibitor, a Complement component 5a (C5a) inhibitor, or a combination thereof.

13. The method of claim 10, wherein at least one symptom of moderate to severe HS is ameliorated after administering an antibiotic, a retinoid, a steroid hormone, an anti-inflammatory, or a combination thereof the subject characterized with moderate to severe HS.

14. The method of claim 10, wherein the Dermatology Quality of Life Index (DQLI) score is decreased after administering an antibiotic, a retinoid, a steroid hormone, an anti-inflammatory, or a combination thereof the subject characterized with moderate to severe HS.

15. The method of claim 10, wherein abscess and inflammatory nodule count (AN count) is decreased after administering an antibiotic, a retinoid, a steroid hormone, an anti-inflammatory, or a combination thereof the subject characterized with moderate to severe HS.

16. The method of claim 10, wherein the severity of HS does not progress after administering an antibiotic, a retinoid, a steroid hormone, an anti-inflammatory, or a combination thereof the subject characterized with moderate to severe HS.

17. The method of claim 10, wherein the method of characterizing HS severity comprises:

a) obtaining a biological sample of a human subject;
b) determining the gene expression level of S100A8, S100A9, NFATC3, dermcidin, and IL-37 in the biological sample by contacting the biological sample with a bead,
wherein the bead comprises at least one oligonucleotide sequence complementary to S100A8, S100A9, NFATC3, dermcidin, and IL-37;
c) detecting binding between S100A8, S100A9, NFATC3, dermcidin, and IL-37 in the biological sample to the bead comprising at least one oligonucleotide sequence complementary to S100A8, S100A9, NFATC3, dermcidin, and IL-37, wherein detection of a bound oligonucleotide is measured using a fluorescent label; and
d) characterizing HS severity as moderate to severe when the expression level of S100A8, S100A9, and NFATC3 is increased in the subject compared to the sample that does not have HS.

18. The method of claim 17, wherein the method of characterizing HS severity further comprises characterizing HS severity as moderate to severe when the expression level of BTK, CD247, HLA-DMA, or HLS-DMB, is increased in the subject compared to the sample that does not have HS.

* * * * *